United States Patent
Mo et al.

(10) Patent No.: US 12,162,947 B2
(45) Date of Patent: Dec. 10, 2024

(54) FUSION PROTEIN AND ITS APPLICATON IN PREPARING MEDICINE FOR TREATING TUMOR AND/OR VIRAL INFECTION

(71) Applicant: NANJING UMAB-BIOPHARMA CO., LTD., Nanjing (CN)

(72) Inventors: Shifu Mo, Nanjing (CN); Yong Zhao, Nanjing (CN); Wei Xu, Nanjing (CN); Zhichao Wang, Nanjing (CN); Jie Yang, Nanjing (CN); Liyun Gu, Nanjing (CN); Dong Ding, Nanjing (CN)

(73) Assignee: NANJING UMAB-BIOPHARMA CO., LTD., Nanjing (CN)

( * ) Notice: Subject to any disclaimer, the term of this patent is extended or adjusted under 35 U.S.C. 154(b) by 941 days.

(21) Appl. No.: 17/192,399

(22) Filed: Mar. 4, 2021

(65) Prior Publication Data
US 2021/0198375 A1 Jul. 1, 2021

Related U.S. Application Data

(63) Continuation-in-part of application No. PCT/CN2019/104217, filed on Sep. 3, 2019.

(30) Foreign Application Priority Data

Sep. 4, 2018 (CN) .......................... 201811024783.1
Dec. 15, 2020 (CN) .......................... 202011478161.3

(51) Int. Cl.
*C07K 16/28* (2006.01)
*C07K 14/56* (2006.01)
*A61K 39/00* (2006.01)

(52) U.S. Cl.
CPC .......... *C07K 16/2878* (2013.01); *C07K 14/56* (2013.01); *A61K 2039/505* (2013.01); *C07K 2317/565* (2013.01); *C07K 2317/73* (2013.01); *C07K 2317/76* (2013.01); *C07K 2319/30* (2013.01)

(58) Field of Classification Search
None
See application file for complete search history.

(56) References Cited

U.S. PATENT DOCUMENTS 9,783,589 B2 * 10/2017 Grewal ................. C07K 14/57
2021/0198375 A1 7/2021 Mo et al.
2021/0269539 A1 9/2021 Mo et al.

FOREIGN PATENT DOCUMENTS

| CN | 107106656 A | 8/2017 | |
|---|---|---|---|
| CN | 108218990 A | 6/2018 | |
| WO | WO-2013059885 A2 * | 5/2013 | ........... A61K 47/642 |
| WO | 2014/028502 A1 | 2/2014 | |
| WO | WO-2017134301 A1 * | 8/2017 | ............. A61K 38/00 |

OTHER PUBLICATIONS

Hemmerle et al., Cancer Immunol Res; 2(6); 559-67. 2014. (Year: 2014).*
Aspeslagh et al. (European Journal of Cancer 52 (2016) 50-66). (Year: 2016).*
International Written Opinion mailed Dec. 2, 2019, issued in International Application No. PCT/CN2019/104217, filed Sep. 3, 2019, 9 pages.
Extended European Search Report mailed Jun. 6, 2022, issued in EP 19857108.5, filed Sep. 3, 2019, 7 pages.
Notice of Reasons for Refusal mailed May 16, 2023, issued in related JP Application No. 2021-510232, filed Sep. 3, 2019, 14 pages.
International Search Report mailed Dec. 2, 2019, issued in International Application No. PCT/CN2019/104217, filed Sep. 3, 2019, 10 pages.

* cited by examiner

*Primary Examiner* — Zachary S Skelding
(74) *Attorney, Agent, or Firm* — Christensen O'Connor Johnson Kindness, PLLC

(57) ABSTRACT

The present disclosure provides a fusion protein and methods thereof for preparing a pharmaceutical composition comprising the fusion protein and for methods for treating tumors and/or viral infections using said fusion proteins and compositions, wherein the fusion protein comprises an antibody or antigen-binding fragment thereof that specifically binds to human OX40 and a human interferon.

16 Claims, 18 Drawing Sheets

Specification includes a Sequence Listing.

SEQUENCE LISTING

```
<160> NUMBER OF SEQ ID NOS: 34

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Tyr Thr Phe Thr Ser Tyr Val Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Tyr Ile Asn Pro Tyr Asn Asp Gly Thr Lys Tyr Asn Glu Lys Phe Lys
1               5                   10                  15
```

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

```
Ala Asn Tyr Tyr Gly Ser Lys Phe Ala Met Asp Tyr
1               5                   10
```

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

```
Arg Ala Ser Gln Asp Ile Ser Asn Tyr Leu Ser
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

```
Tyr Thr Ser Arg Leu His Ser
1               5
```

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

```
Gln Gln Gly Ile Thr Leu Pro Trp Thr
1               5
```

<210> SEQ ID NO 7
<211> LENGTH: 119
<212> TYPE: PRT
<213> ORGANISM: Artificial Sequence
<220> FEATURE:
<223> OTHER INFORMATION: Synthetic

<400> SEQUENCE: 7

```
Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Ser Tyr
            20                  25                  30

Val Met His Trp Leu Arg Gln Met Pro Gly Lys Gly Leu Glu Trp Met
        35                  40                  45

Gly Tyr Ile Asn Pro Tyr Asn Asp Gly Thr Tyr Asn Glu Lys Phe
    50                  55                  60

Lys Gly Gln Val Thr Ile Ser Ser Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Asn Tyr Tyr Gly Ser Lys Phe Ala Met Asp Tyr Trp Gly Gln Gly
            100                 105                 110

Thr Met Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Synthetic

<400> SEQUENCE: 8

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys
            100                 105

<210> SEQ ID NO 9
<211> LENGTH: 165
<212> TYPE: PRT
<213> ORGANISM: Homo sapiens

<400> SEQUENCE: 9

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160
```

Leu Arg Ser Lys Glu
            165

<210> SEQ ID NO 10
<211> LENGTH: 629
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Gln Ser Gly Ala Glu Val Lys Pro Gly Glu
1               5                   10                  15

Ser Leu Lys Ile Ser Cys Lys Ala Ser Gly Tyr Thr Phe Thr Ser Tyr
                20                  25                  30

Val Met His Trp Leu Arg Gln Met Pro Gly Lys Gly Leu Glu Trp Met
            35                  40                  45

Gly Tyr Ile Asn Pro Tyr Asn Asp Gly Thr Lys Tyr Asn Glu Lys Phe
50                  55                  60

Lys Gly Gln Val Thr Ile Ser Ser Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Asn Tyr Tyr Gly Ser Lys Phe Ala Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Gly Gly Gly Ser Gly Gly Gly Gly Ser Gly Gly Gly Gly Ser
    450                 455                 460
Cys Asp Leu Pro Gln Thr His Ser Leu Gly Ser Arg Arg Thr Leu Met
465                 470                 475                 480
Leu Leu Ala Gln Met Arg Arg Ile Ser Leu Phe Ser Cys Leu Lys Asp
                485                 490                 495
Arg His Asp Phe Gly Phe Pro Gln Glu Glu Phe Gly Asn Gln Phe Gln
            500                 505                 510
Lys Ala Glu Thr Ile Pro Val Leu His Glu Met Ile Gln Gln Ile Phe
        515                 520                 525
Asn Leu Phe Ser Thr Lys Asp Ser Ser Ala Ala Trp Asp Glu Thr Leu
    530                 535                 540
Leu Asp Lys Phe Tyr Thr Glu Leu Tyr Gln Gln Leu Asn Asp Leu Glu
545                 550                 555                 560
Ala Cys Val Ile Gln Gly Val Gly Val Thr Glu Thr Pro Leu Met Lys
                565                 570                 575
Glu Asp Ser Ile Leu Ala Val Arg Lys Tyr Phe Gln Arg Ile Thr Leu
            580                 585                 590
Tyr Leu Lys Glu Lys Lys Tyr Ser Pro Cys Ala Trp Glu Val Val Arg
        595                 600                 605
Ala Glu Ile Met Arg Ser Phe Ser Leu Ser Thr Asn Leu Gln Glu Ser
    610                 615                 620
Leu Arg Ser Lys Glu
625

<210> SEQ ID NO 11
<211> LENGTH: 214
<212> TYPE: PRT
<213> ORGANISM: Artificial Sequence
<220> FEATURE:
<223> OTHER INFORMATION: Synthetic

<400> SEQUENCE: 11

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Asp Ile Ser Asn Tyr
            20                  25                  30
Leu Ser Trp Tyr Gln Gln Lys Pro Gly Gly Ala Val Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
```

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 445
<212> TYPE: PRT
<213> ORGANISM: Artificial Sequence
<220> FEATURE:
<223> OTHER INFORMATION: Synthetic

<400> SEQUENCE: 12

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Ser Tyr
            20                  25                  30

Val Met His Trp Leu Arg Gln Met Pro Gly Lys Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Gln Val Thr Ile Ser Ser Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Asn Tyr Tyr Gly Ser Lys Phe Ala Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

```
Cys Pro Pro Cys Pro Ala Pro Pro Val Ala Gly Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 13
<211> LENGTH: 394
<212> TYPE: PRT
<213> ORGANISM: Artificial Sequence
<220> FEATURE:
<223> OTHER INFORMATION: Synthetic

<400> SEQUENCE: 13

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Cys Asp Leu Pro Gln Thr His Ser Leu Gly Ser
225                 230                 235                 240

Arg Arg Thr Leu Met Leu Leu Ala Gln Met Arg Arg Ile Ser Leu Phe
                245                 250                 255

Ser Cys Leu Lys Asp Arg His Asp Phe Gly Phe Pro Gln Glu Glu Phe
            260                 265                 270

Gly Asn Gln Phe Gln Lys Ala Glu Thr Ile Pro Val Leu His Glu Met
        275                 280                 285

Ile Gln Gln Ile Phe Asn Leu Phe Ser Thr Lys Asp Ser Ser Ala Ala
290                 295                 300

Trp Asp Glu Thr Leu Leu Asp Lys Phe Tyr Thr Glu Leu Tyr Gln Gln
305                 310                 315                 320

Leu Asn Asp Leu Glu Ala Cys Val Ile Gln Gly Val Gly Val Thr Glu
                325                 330                 335

Thr Pro Leu Met Lys Glu Asp Ser Ile Leu Ala Val Arg Lys Tyr Phe
            340                 345                 350

Gln Arg Ile Thr Leu Tyr Leu Lys Glu Lys Lys Tyr Ser Pro Cys Ala
        355                 360                 365

Trp Glu Val Val Arg Ala Glu Ile Met Arg Ser Phe Ser Leu Ser Thr
370                 375                 380

Asn Leu Gln Glu Ser Leu Arg Ser Lys Glu
385                 390

<210> SEQ ID NO 14
<211> LENGTH: 449
<212> TYPE: PRT
<213> ORGANISM: Artificial Sequence
<220> FEATURE:
<223> OTHER INFORMATION: Synthetic

<400> SEQUENCE: 14

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Ser Tyr
                20                  25                  30

Val Met His Trp Leu Arg Gln Met Pro Gly Lys Gly Leu Glu Trp Met
            35                  40                  45

Gly Tyr Ile Asn Pro Tyr Asn Asp Gly Thr Lys Tyr Asn Glu Lys Phe
        50                  55                  60

Lys Gly Gln Val Thr Ile Ser Ser Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Asn Tyr Tyr Gly Ser Lys Phe Ala Met Asp Tyr Trp Gly Gln Gly
            100                 105                 110
```

```
Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 15
<211> LENGTH: 446
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Ser Tyr
```

```
            20                  25                  30
Val Met His Trp Leu Arg Gln Met Pro Gly Lys Gly Leu Glu Trp Met
            35                  40                  45
Gly Tyr Ile Asn Pro Tyr Asn Asp Gly Thr Lys Tyr Asn Glu Lys Phe
            50                  55                  60
Lys Gly Gln Val Thr Ile Ser Ser Asp Lys Ser Ile Ser Thr Ala Tyr
 65                  70                  75                  80
Leu Gln Trp Ser Ser Leu Lys Ala Ser Asp Thr Ala Met Tyr Tyr Cys
                85                  90                  95
Ala Asn Tyr Tyr Gly Ser Lys Phe Ala Met Asp Tyr Trp Gly Gln Gly
            100                 105                 110
Thr Met Val Thr Val Ser Ser Ala Ser Thr Lys Gly Pro Ser Val Phe
            115                 120                 125
Pro Leu Ala Pro Cys Ser Arg Ser Thr Ser Glu Ser Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
            195                 200                 205
Ser Asn Thr Lys Val Asp Lys Arg Val Glu Ser Lys Tyr Gly Pro Pro
            210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
            435                 440                 445
```

<210> SEQ ID NO 16
<211> LENGTH: 384
<212> TYPE: PRT
<213> ORGANISM: Artificial Sequence
<220> FEATURE:
<223> OTHER INFORMATION: Synthetic

<400> SEQUENCE: 16

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Cys Asp Leu Pro Gln
210                 215                 220

Thr His Ser Leu Gly Ser Arg Arg Thr Leu Met Leu Leu Ala Gln Met
225                 230                 235                 240

Arg Lys Ile Ser Leu Phe Ser Cys Leu Lys Asp Arg His Asp Phe Gly
                245                 250                 255

Phe Pro Gln Glu Glu Phe Gly Asn Gln Phe Gln Lys Ala Glu Thr Ile
            260                 265                 270

Pro Val Leu His Glu Met Ile Gln Gln Ile Phe Asn Leu Phe Ser Thr
        275                 280                 285

Lys Asp Ser Ser Ala Ala Trp Asp Glu Thr Leu Leu Asp Lys Phe Tyr
290                 295                 300

Thr Glu Leu Tyr Gln Gln Leu Asn Asp Leu Glu Ala Cys Val Ile Gln
305                 310                 315                 320

Gly Val Gly Val Thr Glu Thr Pro Leu Met Lys Glu Asp Ser Ile Leu
                325                 330                 335

Ala Val Arg Lys Tyr Phe Gln Arg Ile Thr Leu Tyr Leu Lys Glu Lys
            340                 345                 350

Lys Tyr Ser Pro Cys Ala Trp Glu Val Val Arg Ala Glu Ile Met Arg
        355                 360                 365
```

Ser Phe Ser Leu Ser Thr Asn Leu Gln Glu Ser Leu Arg Ser Lys Glu
        370                 375                 380

<210> SEQ ID NO 17
<211> LENGTH: 385
<212> TYPE: PRT
<213> ORGANISM: Artificial Sequence
<220> FEATURE:
<223> OTHER INFORMATION: Synthetic

<400> SEQUENCE: 17

Asp Ile Gln Met Thr Gln Ser Pro Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Met Ser Tyr Asn Leu
210                 215                 220

Leu Gly Phe Leu Gln Arg Ser Ser Asn Phe Gln Cys Gln Lys Leu Leu
225                 230                 235                 240

Trp Gln Leu Asn Gly Arg Leu Glu Tyr Cys Leu Lys Asp Arg Met Asn
                245                 250                 255

Phe Asp Ile Pro Glu Glu Ile Lys Gln Leu Gln Gln Phe Gln Lys Glu
            260                 265                 270

Asp Ala Ala Leu Thr Ile Tyr Glu Met Leu Gln Asn Ile Phe Ala Ile
        275                 280                 285

Phe Arg Gln Asp Ser Ser Ser Thr Gly Trp Asn Glu Thr Ile Val Glu
290                 295                 300

Asn Leu Leu Ala Asn Val Tyr His Gln Ile Asn His Leu Lys Thr Val
305                 310                 315                 320

Leu Glu Glu Lys Leu Glu Lys Glu Asp Phe Thr Arg Gly Lys Leu Met
                325                 330                 335

Ser Ser Leu His Leu Lys Arg Tyr Tyr Gly Arg Ile Leu His Tyr Leu
            340                 345                 350

```
Lys Ala Lys Glu Tyr Ser His Cys Ala Trp Thr Ile Val Arg Val Glu
            355                 360                 365

Ile Leu Arg Asn Phe Tyr Phe Ile Asn Arg Leu Thr Gly Tyr Leu Arg
    370                 375                 380

Asn
385

<210> SEQ ID NO 18
<211> LENGTH: 362
<212> TYPE: PRT
<213> ORGANISM: Artificial Sequence
<220> FEATURE:
<223> OTHER INFORMATION: Synthetic

<400> SEQUENCE: 18

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys Gly Gly Gly Ser Gln Asp Pro Tyr Val
    210                 215                 220

Lys Glu Ala Glu Asn Leu Lys Lys Tyr Phe Asn Ala Gly His Ser Asp
225                 230                 235                 240

Val Ala Asp Asn Gly Thr Leu Phe Leu Gly Ile Leu Lys Asn Trp Lys
            245                 250                 255

Glu Glu Ser Asp Arg Lys Ile Met Gln Ser Gln Ile Val Ser Phe Tyr
        260                 265                 270

Phe Lys Leu Phe Lys Asn Phe Lys Asp Asp Gln Ser Ile Gln Lys Ser
    275                 280                 285

Val Glu Thr Ile Lys Glu Asp Met Asn Val Lys Phe Phe Asn Ser Asn
    290                 295                 300

Lys Lys Lys Arg Asp Asp Phe Glu Lys Leu Thr Asn Tyr Ser Val Thr
305                 310                 315                 320
```

```
Asp Leu Asn Val Gln Arg Lys Ala Ile His Glu Leu Ile Gln Val Met
                325                 330                 335

Ala Glu Leu Ser Pro Ala Ala Lys Thr Gly Lys Arg Lys Ser Gln
            340                 345                 350

Met Leu Phe Arg Gly Arg Arg Ala Ser Gln
        355                 360

<210> SEQ ID NO 19
<211> LENGTH: 394
<212> TYPE: PRT
<213> ORGANISM: Artificial Sequence
<220> FEATURE:
<223> OTHER INFORMATION: Synthetic

<400> SEQUENCE: 19

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Val Pro Val Ala Arg
    210                 215                 220

Leu Arg Gly Ala Leu Pro Asp Ala Arg Gly Cys His Ile Ala Gln Phe
225                 230                 235                 240

Lys Ser Leu Ser Pro Gln Glu Leu Gln Ala Phe Lys Arg Ala Lys Asp
                245                 250                 255

Ala Leu Glu Glu Ser Leu Leu Leu Lys Asp Cys Lys Cys Arg Ser Arg
            260                 265                 270

Leu Phe Pro Arg Thr Trp Asp Leu Arg Gln Leu Gln Val Arg Glu Arg
        275                 280                 285

Pro Val Ala Leu Glu Ala Glu Leu Ala Leu Thr Leu Lys Val Leu Glu
    290                 295                 300

Ala Thr Ala Asp Thr Asp Pro Ala Leu Gly Asp Val Leu Asp Gln Pro
305                 310                 315                 320
```

```
Leu His Thr Leu His His Ile Leu Ser Gln Leu Arg Ala Cys Ile Gln
                325                 330                 335

Pro Gln Pro Thr Ala Gly Pro Arg Thr Arg Gly Arg Leu His His Trp
            340                 345                 350

Leu His Arg Leu Gln Glu Ala Pro Lys Lys Glu Ser Pro Gly Cys Leu
        355                 360                 365

Glu Ala Ser Val Thr Phe Asn Leu Phe Arg Leu Leu Thr Arg Asp Leu
370                 375                 380

Asn Cys Val Ala Ser Gly Asp Leu Cys Val
385                 390

<210> SEQ ID NO 20
<211> LENGTH: 165
<212> TYPE: PRT
<213> ORGANISM: Artificial Sequence
<220> FEATURE:
<223> OTHER INFORMATION: Synthetic

<400> SEQUENCE: 20

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 21
<211> LENGTH: 446
<212> TYPE: PRT
<213> ORGANISM: Artificial Sequence
<220> FEATURE:
<223> OTHER INFORMATION: Synthetic

<400> SEQUENCE: 21

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Ser Tyr
            20                  25                  30

Val Met His Trp Leu Arg Gln Met Pro Gly Lys Gly Leu Glu Trp Met
        35                  40                  45

Gly Tyr Ile Asn Pro Tyr Asn Asp Gly Thr Lys Tyr Asn Glu Lys Phe
```

```
                50                  55                  60
Lys Gly Gln Val Thr Ile Ser Ser Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Asn Tyr Tyr Gly Ser Lys Phe Ala Met Asp Tyr Trp Gly Gln Gly
                100                 105                 110

Thr Met Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 22
<211> LENGTH: 384
<212> TYPE: PRT
<213> ORGANISM: Artificial Sequence
```

<220> FEATURE:
<223> OTHER INFORMATION: Synthetic

<400> SEQUENCE: 22

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Cys Asp Leu Pro Gln
210                 215                 220

Thr His Ser Leu Gly Ser Arg Arg Thr Leu Met Leu Leu Ala Gln Met
225                 230                 235                 240

Arg Lys Ile Ser Leu Phe Ser Cys Leu Lys Asp Arg His Asp Phe Gly
                245                 250                 255

Phe Pro Gln Glu Glu Phe Gly Asn Gln Phe Gln Lys Ala Glu Thr Ile
            260                 265                 270

Pro Val Leu His Glu Met Ile Gln Gln Ile Phe Asn Leu Phe Ser Thr
        275                 280                 285

Lys Asp Ser Ser Ala Ala Trp Asp Glu Thr Leu Leu Asp Lys Phe Tyr
290                 295                 300

Thr Glu Leu Tyr Gln Gln Leu Asn Asp Leu Glu Ala Cys Val Ile Gln
305                 310                 315                 320

Gly Val Gly Val Thr Glu Thr Pro Leu Met Lys Glu Asp Ser Ile Leu
                325                 330                 335

Ala Val Arg Lys Tyr Phe Gln Arg Ile Thr Leu Tyr Leu Lys Glu Lys
            340                 345                 350

Lys Tyr Ser Pro Cys Ala Trp Glu Val Val Arg Ala Glu Ile Met Arg
        355                 360                 365

Ser Phe Ser Leu Ser Thr Asn Leu Gln Glu Ser Leu Arg Ser Lys Glu
370                 375                 380
```

<210> SEQ ID NO 23

<211> LENGTH: 389
<212> TYPE: PRT
<213> ORGANISM: Artificial Sequence
<220> FEATURE:
<223> OTHER INFORMATION: Synthetic

<400> SEQUENCE: 23

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Cys Asp Leu Pro Gln Thr His Ser Leu Gly Ser Arg Arg Thr Leu Met
225                 230                 235                 240

Leu Leu Ala Gln Met Arg Lys Ile Ser Leu Phe Ser Cys Leu Lys Asp
                245                 250                 255

Arg His Asp Phe Gly Phe Pro Gln Glu Glu Phe Gly Asn Gln Phe Gln
            260                 265                 270

Lys Ala Glu Thr Ile Pro Val Leu His Glu Met Ile Gln Gln Ile Phe
        275                 280                 285

Asn Leu Phe Ser Thr Lys Asp Ser Ser Ala Ala Trp Asp Glu Thr Leu
    290                 295                 300

Leu Asp Lys Phe Tyr Thr Glu Leu Tyr Gln Gln Leu Asn Asp Leu Glu
305                 310                 315                 320

Ala Cys Val Ile Gln Gly Val Gly Val Thr Glu Thr Pro Leu Met Lys
                325                 330                 335

Glu Asp Ser Ile Leu Ala Val Arg Lys Tyr Phe Gln Arg Ile Thr Leu
            340                 345                 350

Tyr Leu Lys Glu Lys Lys Tyr Ser Pro Cys Ala Trp Glu Val Val Arg
        355                 360                 365

Ala Glu Ile Met Arg Ser Phe Ser Leu Ser Thr Asn Leu Gln Glu Ser
    370                 375                 380
```

Leu Arg Ser Lys Glu
385

<210> SEQ ID NO 24
<211> LENGTH: 165
<212> TYPE: PRT
<213> ORGANISM: Artificial Sequence
<220> FEATURE:
<223> OTHER INFORMATION: Synthetic

<400> SEQUENCE: 24

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Ala Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 25
<211> LENGTH: 389
<212> TYPE: PRT
<213> ORGANISM: Artificial Sequence
<220> FEATURE:
<223> OTHER INFORMATION: Synthetic

<400> SEQUENCE: 25

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly

```
                115                 120                 125
Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
210                 215                 220

Cys Asp Leu Pro Gln Thr His Ser Leu Gly Ser Arg Arg Thr Leu Met
225                 230                 235                 240

Leu Leu Ala Gln Met Arg Lys Ile Ser Leu Phe Ser Cys Leu Lys Asp
                245                 250                 255

Arg His Asp Phe Gly Phe Pro Gln Glu Glu Phe Gly Asn Gln Phe Gln
                260                 265                 270

Lys Ala Glu Thr Ile Pro Val Leu His Glu Met Ile Gln Gln Ile Phe
            275                 280                 285

Asn Leu Phe Ser Thr Lys Asp Ser Ser Ala Ala Trp Asp Glu Thr Leu
290                 295                 300

Leu Asp Lys Phe Tyr Thr Glu Leu Tyr Gln Gln Leu Asn Asp Leu Glu
305                 310                 315                 320

Ala Cys Val Ile Gln Gly Val Gly Val Ala Glu Thr Pro Leu Met Lys
                325                 330                 335

Glu Asp Ser Ile Ala Ala Val Arg Lys Tyr Phe Gln Arg Ile Thr Leu
                340                 345                 350

Tyr Leu Lys Glu Lys Lys Tyr Ser Pro Cys Ala Trp Glu Val Val Arg
            355                 360                 365

Ala Glu Ile Met Arg Ser Phe Ser Leu Ser Thr Asn Leu Gln Glu Ser
370                 375                 380

Leu Arg Ser Lys Glu
385

<210> SEQ ID NO 26
<211> LENGTH: 165
<212> TYPE: PRT
<213> ORGANISM: Artificial Sequence
<220> FEATURE:
<223> OTHER INFORMATION: Synthetic

<400> SEQUENCE: 26

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
                35                  40                  45

Lys Ala Glu Thr Ile Pro Val Leu His Glu Met Ile Gln Gln Ile Phe
            50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
```

```
                         85                  90                  95
Ala Cys Val Ile Gln Gly Val Gly Val Ala Glu Thr Pro Leu Met Lys
                100                 105                 110

Glu Asp Ser Ile Ala Ala Val Arg Lys Tyr Phe Gln Arg Ile Thr Leu
                115                 120                 125

Tyr Leu Lys Glu Lys Lys Tyr Ser Pro Cys Ala Trp Glu Val Val Arg
            130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 27
<211> LENGTH: 389
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
                20                  25                  30

Leu Ser Trp Tyr Gln Gln Lys Pro Gly Gly Ala Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Ser
        210                 215                 220

Cys Asp Leu Pro Gln Thr His Ser Leu Gly Ser Arg Arg Thr Leu Met
225                 230                 235                 240

Leu Leu Ala Gln Met Arg Arg Ile Ser Leu Phe Ser Cys Leu Lys Asp
                245                 250                 255

Arg His Asp Phe Gly Phe Pro Gln Glu Glu Phe Gly Asn Gln Phe Gln
            260                 265                 270

Lys Ala Glu Thr Ile Pro Val Leu His Glu Met Ile Gln Gln Ile Phe
```

```
                275                 280                 285
Asn Leu Phe Ser Thr Lys Asp Ser Ser Ala Ala Trp Asp Glu Thr Leu
    290                 295                 300

Leu Asp Lys Phe Tyr Thr Glu Leu Tyr Gln Gln Leu Asn Asp Leu Glu
305                 310                 315                 320

Ala Cys Val Ile Gln Gly Val Gly Val Ala Glu Thr Pro Leu Met Lys
                325                 330                 335

Glu Asp Ser Ile Ala Ala Val Arg Lys Tyr Phe Gln Arg Ile Thr Leu
            340                 345                 350

Tyr Leu Lys Glu Lys Lys Tyr Ser Pro Cys Ala Trp Glu Val Val Arg
        355                 360                 365

Ala Glu Ile Met Arg Ser Phe Ser Leu Ser Thr Asn Leu Gln Glu Ser
    370                 375                 380

Leu Arg Ser Lys Glu
385

<210> SEQ ID NO 28
<211> LENGTH: 165
<212> TYPE: PRT
<213> ORGANISM: Artificial Sequence
<220> FEATURE:
<223> OTHER INFORMATION: Synthetic

<400> SEQUENCE: 28

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Ala Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 29
<211> LENGTH: 389
<212> TYPE: PRT
<213> ORGANISM: Artificial Sequence
<220> FEATURE:
<223> OTHER INFORMATION: Synthetic

<400> SEQUENCE: 29

Asp Ile Gln Met Thr Gln Ser Pro Ser Ser Val Ser Ala Ser Val Gly
1               5                   10                  15
```

-continued

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Cys Asp Leu Pro Gln Thr His Ser Leu Gly Ser Arg Arg Thr Leu Met
225                 230                 235                 240

Leu Leu Ala Gln Met Arg Arg Ile Ser Leu Phe Ser Cys Leu Lys Asp
                245                 250                 255

Arg His Asp Phe Gly Phe Pro Gln Glu Glu Phe Gly Asn Gln Phe Gln
            260                 265                 270

Lys Ala Glu Thr Ile Pro Val Leu His Glu Met Ile Gln Gln Ile Phe
        275                 280                 285

Asn Leu Phe Ser Thr Lys Asp Ser Ser Ala Ala Trp Asp Glu Thr Leu
    290                 295                 300

Leu Asp Lys Phe Tyr Thr Glu Leu Tyr Gln Gln Leu Asn Asp Leu Glu
305                 310                 315                 320

Ala Cys Val Ile Gln Gly Val Gly Val Thr Glu Thr Pro Leu Met Lys
                325                 330                 335

Glu Asp Ser Ile Ala Ala Val Arg Lys Tyr Phe Gln Arg Ile Thr Leu
            340                 345                 350

Tyr Leu Lys Glu Lys Lys Tyr Ser Pro Cys Ala Trp Glu Val Val Arg
        355                 360                 365

Ala Glu Ile Met Arg Ser Phe Ser Leu Ser Thr Asn Leu Gln Glu Ser
    370                 375                 380

Leu Arg Ser Lys Glu
385

<210> SEQ ID NO 30
<211> LENGTH: 18
<212> TYPE: PRT
<213> ORGANISM: Artificial sequence
<220> FEATURE:
<223> OTHER INFORMATION: Synthetic

```
<400> SEQUENCE: 30

Lys Glu Ser Gly Ser Val Ser Ser Glu Gln Leu Ala Gln Phe Arg Ser
1               5                   10                  15

Leu Asp

<210> SEQ ID NO 31
<211> LENGTH: 14
<212> TYPE: PRT
<213> ORGANISM: Artificial sequence
<220> FEATURE:
<223> OTHER INFORMATION: Synthetic

<400> SEQUENCE: 31

Glu Gly Lys Ser Ser Gly Ser Gly Ser Glu Ser Lys Ser Thr
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic

<400> SEQUENCE: 32

Gly Ser Ala Gly Ser Ala Ala Gly Ser Gly Glu Phe
1               5                   10

<210> SEQ ID NO 33
<211> LENGTH: 5
<212> TYPE: PRT
<213> ORGANISM: Artificial sequence
<220> FEATURE:
<223> OTHER INFORMATION: Synthetic

<400> SEQUENCE: 33

Gly Gly Gly Gly Ser
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic

<400> SEQUENCE: 34

Gly Gly Ser Gly Gly
1               5
```

FUSION PROTEIN AND ITS APPLICATON IN PREPARING MEDICINE FOR TREATING TUMOR AND/OR VIRAL INFECTION

CROSS-REFERENCE TO RELATED APPLICATIONS

This application is a continuation-in-part of PCT/CN2019/104217, filed Sep. 3, 2019, which claims priority to Chinese Application No. 2018110247831, filed Sep. 4, 2018. This application also claims priority to Chinese Application No. 2020114781613, filed Dec. 15, 2020. The disclosures of each application are hereby incorporated by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is PAWE173940_Seq_List_final_20210304_ST25.txt. The text file is 68 KB; was created on Mar. 4, 2021; and is being submitted via EFS-Web with the filing of the specification.

TECHNICAL FIELD

The present invention belongs to the field of biomedicine. Specifically, the present invention relates to a fusion protein and use thereof. More specifically, the present invention relates to a fusion protein comprising an anti-OX40 antibody and a human interferon, and use thereof in preparing a medicament for treating tumors and/or viral infections.

BACKGROUND ART

Human OX40 is mainly expressed on activated T cells, including CD4, CD8, Th, Treg cells, and etc. [1] The expression level of OX40 on naïve T cells is low, but is up-regulated after antigen-induced stimulation and peaks within 12 h to 5-6 days. Similarly, the expression level of OX40L is also affected by the state of cell activation [1]. The expression of OX40L may be detected in APC cells 1-3 days after antigen stimulation. Interestingly, in addition to immune cells, muscle cells also express OX40L under the stimulation of inflammatory factors [2, 3], suggesting that OX40L-OX40 signaling pathway may play a wide role in the inflammatory response of the body.

The antigen-dependent activation of OX40L/OX40 costimulatory molecules is coupled to multiple signaling pathways in T cells. Crystal structure studies have shown that the binding of OX40L to OX40 may induce the trimerization of OX40-OX40L complex [4], thus forming a binding site for receptor-associated factor (TRAF) in the cell. The latter (TRAF2, 5) could then activate NF-κB signaling pathway and inhibit T cell apoptosis [2, 5, 6]. Studies have found that the activation of OX40 may result in the high expression of Bcl-2 and Bcl-xL [7], suggesting that OX40 may induce the expression of anti-apoptotic protein through NF-κB signaling pathway to achieve its function of inhibiting T cell apoptosis.

PKB/PI3K is another important signaling pathway located downstream of OX40. Studies have found that, on the one hand, the costimulatory signal of OX40 on T cells is necessary to maintain PKB activation, and on the other hand, constitutively activated PKB could antagonize the down-regulation of anti-apoptotic protein in T cells caused by OX40 deficiency. OX40 costimulatory signal can maintain the expression of Survivin through PKB/PI3K signaling pathway [8].

Finally, the activation of TCR and OX40 on T cells may also synergistically cause calcium flux and the activation of NFAT signaling pathway, regulating the expression of cytokines including IL-2, IL-4, IL-5, and IFN-γ [9].

In summary, the above studies indicate that activation of OX40 may regulate T cell proliferation and apoptosis, and cytokine secretion activity through NF-κB signaling pathway, PKB/PI3K signaling pathway and NFAT signaling pathway, thereby achieving the effect of enhancing immune system activity.

Based on the above findings, OX40 has become an important target for immunotherapy, and numerous preclinical and clinical studies suggest that OX40 may be an important target for tumor immunotherapy. Interestingly, recent studies have also found the role of OX40 signaling pathway in inhibiting hepatitis B virus infection [10], suggesting that OX40 agonists may be used as a potential means for antiviral infections, such as the treatment of hepatitis B patients.

Interferons is a class of multifunctional glycoproteins with a high activity. On the one hand, interferon can exert a potent anti-tumor effect by regulating tumor cell proliferation, inhibiting tumor metastasis and angiogenesis, and activating anti-tumor immune response; on the other hand, by regulating the human immune system, interferon has an important clinical application value in antiviral application, for example, interferon has become one of important means for clinical treatment of hepatitis B virus infection.

Human interferon IFNα-2a and human interferon IFNα-2b are two types of human interferon. The amino acid at position 23 of human interferon IFNα-2a is lysine (Lys), and unlike IFNα-2a, the amino acid at position 23 of IFNα-2b is arginine (Arg). Further, recombinant human INFα-2b exists as a crystal of noncovalent dimer with a zinc ion-mediated dimer surface interaction. Of all INFα subtypes, only two subtypes INFα-2b and INFα-14c are glycosylated. INFα-2b is the only INFα subtype with a threonine residue at position 106, and also the only 0-glycosylated human INFα protein. The above structural differences may affect the immunogenicity and immunotoxicity of different IFNα-2 subtypes. The existing art shows that there is a certain immunogenic difference between IFNα-2a and INFα-2b, but no difference in immunotoxicity.

Both OX40 agonist and interferon have an important application value or potential in anti-tumor and anti-viral applications, but the existing evidence suggests that they have deficiencies in patient responsiveness and efficacy. Therefore, there is a demand for an OX40 agonist and an interferon showing better therapeutic effects.

Contents of the Disclosure

It is an objective of the present disclosure is to provide a fusion protein comprising an antibody or antigen-binding fragment thereof that specifically binds to human OX40 and a human interferon. The present disclosure also provides use of the fusion protein for treating tumors and/or viral infections.

To achieve the above objectives, the present disclosure adopts the following technical solutions.

In one aspect, the present disclosure provides a fusion protein comprising:
  a) an antibody or antigen-binding fragment thereof that specifically binds to human OX40; and
  b) a human interferon;

wherein the human interferon is linked to the carboxyl- or amino-terminus of the light or heavy chain of the antibody directly or via a peptide linker.

In the fusion protein according to the present disclosure, the antibody or antigen-binding fragment thereof that specifically binds to human OX40 comprises:
an antibody heavy chain variable region comprising VH CDR1 having the amino acid sequence of SEQ ID NO:1, VH CDR2 having the amino acid sequence of SEQ ID NO:2, and VH CDR3 having the amino acid sequence of SEQ ID NO:3; and
an antibody light chain variable region comprising VL CDR1 having the amino acid sequence of SEQ ID NO: 4, VL CDR2 having the amino acid sequence of SEQ ID NO: 5, and VL CDR3 having the amino acid sequence of SEQ ID NO: 6.

In the fusion protein according to the present disclosure, the heavy chain variable region comprises the amino acid sequence as shown in SEQ ID NO:7, and the light chain variable region comprises the amino acid sequence as shown in SEQ ID NO:8.

In another aspect, the present disclosure provides a fusion protein comprising:
a) an antibody or antigen-binding fragment thereof that specifically binds to human OX40; and
b) human interferon IFNα-2a or a mutant thereof;
wherein the human interferon IFNα-2a or mutant thereof is linked to the carboxyl- or amino-terminus of the light or heavy chain of the antibody or antigen-binding fragment thereof that specifically binds to human OX40 directly, or via a peptide linker.

In the fusion protein according to this aspect of the disclosure, the antibody or antigen-binding fragment thereof that specifically binds to human OX40 comprises:
a heavy chain variable region comprising three complementarity determining regions (HCDR1, HCDR2 and HCDR3) in the heavy chain variable region (VH) as shown in SEQ ID NO:7, wherein each HCDR is defined as shown in Table 1 in the following description part of the present patent application; and
a light chain variable region comprising three complementarity determining regions (LCDR1, LCDR2 and LCDR3) in the light chain variable region (VL) as shown in SEQ ID NO:8, wherein each LCDR is defined as shown in Table 1 in the following description of the present patent application.

Preferably, the heavy chain variable region comprises or consists of the amino acid sequence as shown in SEQ ID NO:7, and the light chain variable region comprises or consists of the amino acid sequence as shown in SEQ ID NO:8.

In the fusion protein according to the present invention, the antibody or antigen-binding fragment thereof that specifically binds to human OX40 is a camelized single-domain antibody, scFv, a scFv dimer, BsFv, dsFv, dsFv$_2$, dsFv-dsFv', a Fv fragment, Fab, Fab', F(ab')$_2$, a ds diabody, a nanobody, a domain antibody, or a bivalent domain antibody.

In the fusion protein according to the present invention, the antibody further comprises a constant region of immunoglobulin, for example, a constant region of human IgG1, IgG2 or IgG4.

In the fusion protein according to the present invention, the human interferon is selected from the group consisting of human interferon type I, human interferon type II, and human interferon type III; preferably the human interferon is IFNα-2a, IFNβ, IFNγ, IFNλ, or IFNα-2b; more preferably, the human interferon is IFNα-2b having the amino acid sequence as shown in SEQ ID NO:9.

Further preferably, in one embodiment the human interferon is an IFNα-2b mutant, which has one or more mutations selected from the group consisting of: T106A, R149A, A145G, A145D, R120A, and L117A, relative to the amino acid sequence as shown in SEQ ID NO:9; more preferably, the IFNα2b mutant has one or more double mutations selected from the group consisting of: T106A/A145D, T106A/R149A, T106A/A145G, T106A/L117A, and T106A/R120A, relative to the amino acid sequence as shown in SEQ ID NO:9.

In another embodiment the fusion protein according to the present disclosure, the amino acid sequence of human interferon IFNα-2a is as shown in SEQ ID NO:20; further preferably, the amino acid sequence of human interferon IFNα-2a mutant has one or more mutations selected from the group consisting of: T106A, R149A, A145G, A145D, R120A, and L117A relative to the amino acid sequence as shown in SEQ ID NO:20; further more preferably, the amino acid sequence of human interferon IFNα-2a mutant has one or more double mutations selected from the group consisting of: T106A/A145D, T106A/R149A, T106A/A145G, T106A/R120A, and T106A/L117A relative to the amino acid sequence as shown in SEQ ID NO:20.

In the fusion protein according to the present invention, the peptide linker is selected from the group consising of (G)$_n$, KESGSVSSEQLAQFRSLD (SEQ ID NO:30), EGKSSGSGSESKST (SEQ ID NO:31), GSAGSAAGSGEF (SEQ ID NO:32), (GGGGS)$_n$ (SEQ ID NO:33), and (GGSGG)$_n$ (SEQ ID NO:34); preferably, the peptide linker is (GGGGS)$_n$; wherein n is an integer between 0 and 5; preferably, n is an integer between 1 and 3.

In the fusion protein according to the present disclosure, the fusion protein is selected from the group consisting of:
UMY02-L1, comprising the amino acid sequences as shown in SEQ ID NO:10 and SEQ ID NO:11, wherein the amino acid sequence as shown in SEQ ID NO:10 represents the heavy chain of the antibody of OX40, the peptide linker and the human interferon, and the amino acid sequence as shown in SEQ ID NO:11 represents the light chain of the antibody of OX40;
UMY02-L2, comprising the amino acid sequences as shown in SEQ ID NO:12 and SEQ ID NO:13, wherein the amino acid sequence as shown in SEQ ID NO:12 represents the heavy chain of the antibody of OX40, and the amino acid sequence as shown in SEQ ID NO:13 represents the light chain of the antibody of OX40, the peptide linker and the human interferon;
UMY02-L3, comprising the amino acid sequences as shown in SEQ ID NO:14 and SEQ ID NO:13, wherein the amino acid sequence as shown in SEQ ID NO:14 represents the heavy chain of the antibody of OX40, and the amino acid sequence as shown in SEQ ID NO:13 represents the light chain of the antibody of OX40, the peptide linker and the human interferon;
UMY02-L4, in which the heavy chain is as shown in SEQ ID NO:14, and the light chain and the human interferon are as shown in SEQ ID NO:13, without a peptide linker;
UMY02-L5, in which the heavy chain is as shown in SEQ ID NO:14, and the light chain and the human interferon are as shown in SEQ ID NO:13, with the peptide linker of GGGGS as shown in SEQ ID NO:33;

UMY02-L6, in which the heavy chain is as shown in SEQ ID NO:14, and the light chain and the human interferon are as shown in SEQ ID NO:13, with the peptide linker of (GGGGS)$_2$;

UMY02-L7, in which the heavy chain is as shown in SEQ ID NO:15, and the light chain and the human interferon are as shown in SEQ ID NO:13, with the peptide linker of GGGGS as shown in SEQ ID NO:33;

UMY02-L8, in which the heavy chain is as shown in SEQ ID NO:15, and the light chain and the human interferon are as shown in SEQ ID NO:13, with the peptide linker of (GGGGS)$_2$;

UMY02-L13, in which the heavy chain is as shown in SEQ ID NO:15, and the light chain and the human interferon are as shown in SEQ ID NO:13, with the peptide linker of (GGGGS)$_2$, and the interferon has the mutation of T106A/A145D relative to SEQ ID NO:9;

UMY02-L14, in which the heavy chain is as shown in SEQ ID NO:15, and the light chain and the human interferon are as shown in SEQ ID NO:13, with the peptide linker of (GGGGS)$_2$, and the interferon has the mutation of T106A/R149A relative to SEQ ID NO:9;

UMY02-L15, in which the heavy chain is as shown in SEQ ID NO:15, and the light chain and the human interferon are as shown in SEQ ID NO:13, with the peptide linker of (GGGGS)$_2$, and the interferon has the mutation of T106A/R120A relative to SEQ ID NO:9;

UMY02-L16, in which the heavy chain is as shown in SEQ ID NO:15, and the light chain and the human interferon are as shown in SEQ ID NO:13, with the peptide linker of (GGGGS)$_2$, and the interferon has the mutation of T106A/A145G relative to SEQ ID NO:9;

UMY02-L17, in which the heavy chain is as shown in SEQ ID NO:15, and the light chain and the human interferon are as shown in SEQ ID NO:13, with the peptide linker of (GGGGS)$_3$, and the interferon has the mutation of T106A/R149A relative to SEQ ID NO:9;

UMY02-L18, in which the heavy chain is as shown in SEQ ID NO:15, and the light chain and human interferon are as shown in SEQ ID NO:13, with the peptide linker of (GGGGS)$_2$, and the interferon has the mutation of T106A/L117A relative to SEQ ID NO:9; and The fusion proteins OX40 IFN-α2a, OX40-IFNβ, OX40-IFNγ, and OX40-IFNλ3, in which the heavy chains of OX40 IFN-α2a, OX40-IFNβ, OX40-IFNγ, and OX40-IFNλ3 are as shown in SEQ ID NO:15; the light chain, the peptide linker and the interferon of OX40 IFN-α2a are as shown in SEQ ID NO:16; the light chain, the peptide linker and the interferon of OX40 IFN-β are as shown in SEQ ID NO:17; the light chain, the peptide linker and the interferon of OX40 IFN-γ are as shown in SEQ ID NO:18; and the light chain, the peptide linker and the interferon of OX40 IFN-λ3 are as shown in SEQ ID NO:19.

The fusion protein according to the present disclosure can also be selected from the group consisting of:

UM06-L9, consisting of an antibody that specifically binds to human OX40 comprising the heavy chain as shown in SEQ ID NO:21 and the light chain as shown in SEQ ID NO:22, a peptide linker, and the human interferon IFNα-2a as shown in SEQ ID NO.20, wherein the human interferon IFNα-2a is linked to the carboxyl-terminus of the light chain of the antibody that specifically binds to human OX40 via a peptide linker GGGGS as shown in SEQ ID NO:33;

UM06-L9.1, consisting of an antibody that specifically binds to human OX40 comprising the heavy chain as shown in SEQ ID NO:21 and the light chain as shown in SEQ ID NO:7a, a peptide linker, and the human interferon IFNα-2a as shown in SEQ ID NO:20, wherein the human interferon IFNα-2a is linked to the carboxyl-terminus of the light chain of the antibody that specifically binds to human OX40 via a peptide linker (GGGGS)$_2$;

UM06-L21, consisting of an antibody that specifically binds to human OX40 comprising the heavy chain as shown in SEQ ID NO:21 and the light chain as shown in SEQ ID NO:25, a peptide linker, and the human interferon IFNα-2a mutant (T106A/L117A) as shown in SEQ ID NO:24, wherein the human interferon IFNα-2a mutant is linked to the carboxyl-terminus of the light chain of the antibody that specifically binds to human OX40 via a peptide linker (GGGGS)$_2$.

In another aspect, the present disclosure provides an isolated polynucleotide encoding the fusion protein.

In yet another aspect, the present disclosure provides a vector comprising the isolated polynucleotide.

In yet another aspect, the present disclosure provides a host cell comprising the vector.

The present disclosure also provides a method of expressing the fusion protein comprising culturing the host cell under conditions capable of expressing the isolated polynucleotide.

The present disclosure also provides a kit containing the fusion protein.

The present disclosure also provides a pharmaceutical composition comprising the fusion protein and a pharmaceutically acceptable carrier.

The present disclosure also provides use of the fusion protein in preparing a medicament for treating a condition benefiting from enhancing an immune response and/or exposure to an interferon.

Preferably, the condition is cancer or viral infection, such as hepatitis B virus infection.

The present disclosure provides a method of treating a condition benefiting from enhancing an immune response and/or exposure to an interferon, comprising administering to a subject in need thereof a therapeutically effective amount of the fusion protein; preferably, the condition is cancer or viral infection, such as hepatitis B virus infection.

The present disclosure provides a fusion protein for treating a condition benefiting from enhancing an immune response and/or exposure to an interferon; preferably, the condition is cancer or viral infection, such as hepatitis B virus infection.

The present disclosure provides a fusion protein of an OX40 agonistic antibody and an interferon, which combines their different action mechanisms simultaneously and produces a synergistic enhancement effect: on the one hand, when the interferon moiety in the fusion protein binds to the surface of a cell that highly expresses interferon receptors (e.g., tumor or virus-infected cell), it is possible to enhance the activity of OX40 activating antibody in a receptor-mediated manner, thereby better enhancing the activity of immune system; on the other hand, compared with an interferon molecule, the half-life of the fusion protein of the present invention is greatly prolonged, so that the fusion protein can be administered clinically at a lower frequency, and has great advantages compared with the current interferons which need to be injected clinically every day.

In summary, the fusion protein of the present disclosure is promising to show unique efficacy and compliance advantages in antitumor and antiviral therapy.

BRIEF DESCRIPTION OF THE DRAWINGS

The embodiments of the present disclosure will be described below in conjunction with the accompanying drawings, wherein:

FIG. 7B shows the pharmacokinetic profile of MT01-C1 on mice;

SPECIFIC EMBODIMENTS

Figure 1:
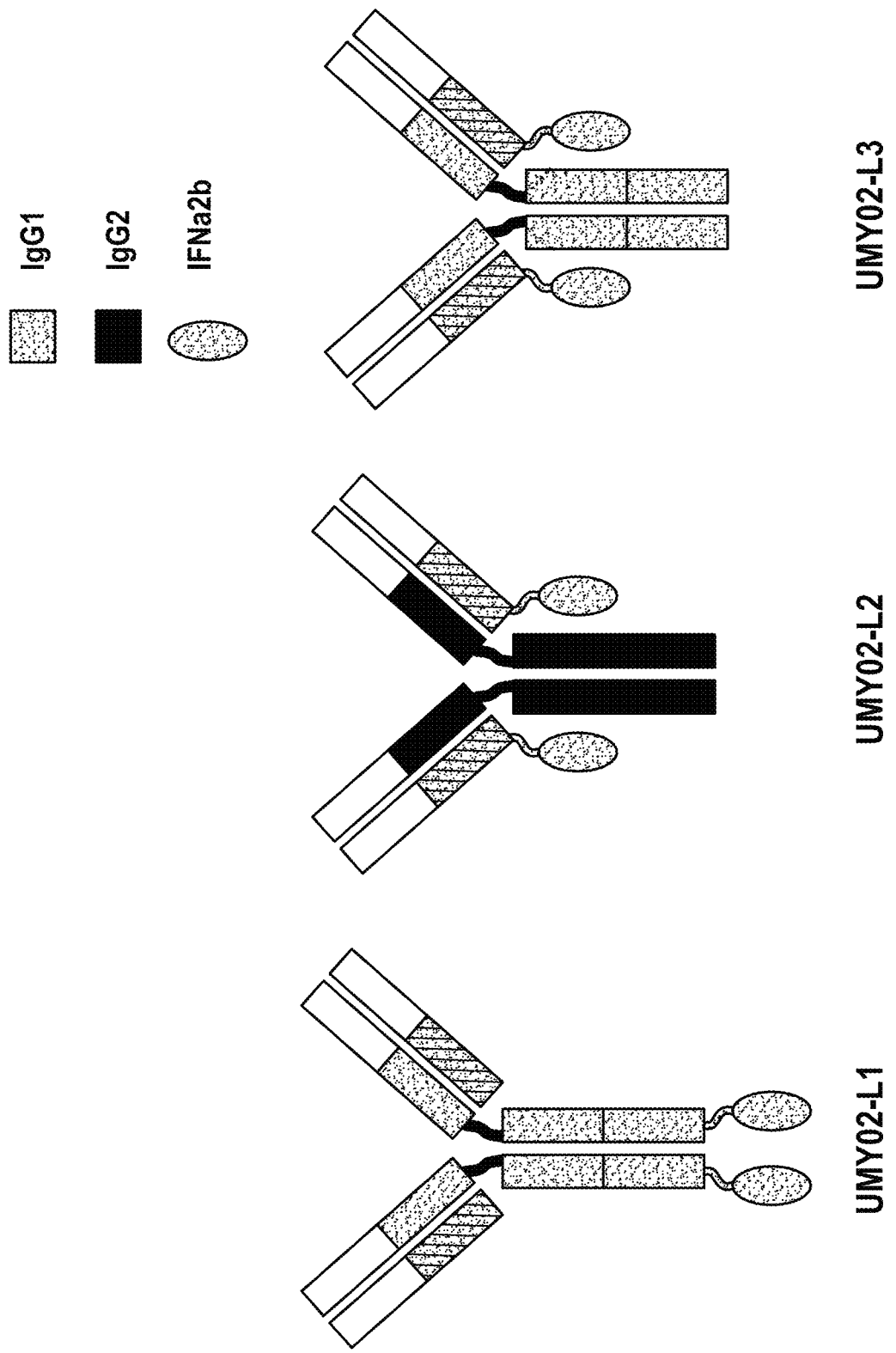
FIG. 1 shows the schematic diagram of structures of the fusion proteins according to the present invention.

The following description of the present application is merely illustrative of various embodiments of the present application. Therefore, the specific embodiments discussed herein should not be construed as limiting the scope of the present application. Numerous equivalents, changes and modifications will readily occur to those skilled in the art without departing from the scope of the present application, and it is to be understood that such equivalents are encompassed within the scope of the present invention. All documents, including publications, patents, and patent applications, cited in this application are hereby incorporated by reference in their entirety.

Definitions

The term "antibody" in the present invention encompasses any immunoglobulin, monoclonal antibody, polyclonal antibody, multispecific antibody, or bispecific (bivalent) antibody that can bind to a specific antigen. A native intact antibody comprises two heavy chains and two light chains. Each heavy chain consists of a variable region, a first constant region, a second constant region and a third constant region, and each light chain consists of a variable region and a constant region. Mammalian heavy chains can be classified as α, δ, ε, γ, and μ, and mammalian light chains can be classified as λ or κ. An antibody is of "Y" type, and the neck of the Y-type structure consists of a second and a third constant regions of the two heavy chains, which are bound by disulfide bonds. Each arm of the "Y" structure comprises a variable region and a first constant region of one of the heavy chains, which bind to a variable region and a constant region of one of the light chains. The variable regions of the light and heavy chains determine antigen binding. The variable region of each chain comprises three hypervariable regions, termed complementarity determining regions (CDRs). The CDRs of the light chain (L) include LCDR1, LCDR2, and LCDR3, and the CDRs of the heavy chain (H) include HCDR1, HCDR2, and HCDR3.

"CDR" is a region in antibody variable domain that is highly variable in sequence and forms a structurally defined loop ("hypervariable loop") and/or comprises antigen-contacting residues ("antigen-contacting points"). The CDR is primarily responsible for the binding to antigenic epitope. The CDRs of the heavy and light chains are commonly referred to as CDR1, CDR2 and CDR3, numbered sequentially from the N-terminus. The CDRs located within the variable domain of heavy chain of an antibody are referred to as HCDR1, HCDR2 and HCDR3, while the CDRs located within the variable domain of light chain of an antibody are referred to as LCDR1, LCDR2 and LCDR3. In a given light chain variable region or heavy chain variable region amino acid sequence, the exact amino acid sequence boundaries of each CDR may be determined using any one or a combination of a number of well-known antibody CDR designation systems, including, for example: Chothia based on the three-dimensional structure of antibody and the topology of CDR loop (Chothia et al., Nature 342:877-883 (1989); A1-Lazikani et al., "Standard Conformations for the Canonical Structures of Immunoglobulins", J. Mol. Biol. 273:927-948 (1997)); Kabat based on antibody sequence variability (Kabat et al., Sequences of Proteins of Immunological Interest, 4th ed., U.S. Department of Health and Human Services, National Institutes of Health (1987), AbM (University of Bath), Contact (University College London), International ImmunoGeneTics database (IMGT) (on the World Wide Web); and North CDR definition based on affinity propagation clustering using a large number of crystal structures.

For example, according to different CDR determination schemes, the residues of each CDR of antibody in the fusion protein of the present invention are defined as follows (Table 1).

TABLE 1

Definitions of antibody CDRs

| CDR | Numbering system | Kabat Scheme | AbM Scheme | Chothia Scheme | Contact Scheme |
|---|---|---|---|---|---|
| LCDR1 | Kabat | L24-L34 | L24-L34 | L26-L32 | L30-L36 |
| LCDR2 | | L50-L56 | L50-L56 | L50-L52 | L46-L55 |
| LCDR3 | | L89-L97 | L89-L97 | L91-L96 | L89-L96 |
| HCDR1 | Kabat | H31-H35B | H26-H35B | H26-H32 | H30-H35B |
| | Chothia | H31-H35 | H26-H35 | H26-H32 | H30-H35 |
| HCDR2 | Kabat | H50-H65 | H50-H58 | H53-H55 | H47-H58 |
| HCDR3 | | H95-H102 | H95-H102 | H96-H101 | H93-H101 |

Unless otherwise indicated, the term "CDR" or "CDR sequence" used herein encompasses combinations of CDR sequences determined in any of the ways described above.

Antibodies with different specificities (i.e., different binding sites for different antigens) have different CDRs. However, although CDRs vary from antibody to antibody, only a limited number of amino acid positions within the CDRs are directly involved in antigen binding. Using at least two of the Kabat, Chothia, AbM, and Contact methods, the minimum overlap region can be determined to provide a "minimum binding unit" for antigen binding. The minimum binding unit may be a subsection of CDRs. As will be apparent to those skilled in the art, the residues of the remainder of CDR sequence can be determined by the structure and protein folding of the antibody. Thus, the present disclosure also contemplates any variants of CDR set forth herein. For example, in a variant of CDR, the amino acid residues of the minimum binding unit may remain unchanged, while the remaining CDR residues defined according to Kabat or Chothia may be replaced by conserved amino acid residues.

The three CDRs are separated by contiguous flanking regions called framework regions (FR), which are more highly conserved than the CDRs and form a scaffold to support the hypervariable loop. The constant regions of the heavy and light chains are independent of antigen binding, but have multiple effector functions. Antibodies can be divided into several classes depending on the amino acid sequence of the constant region of heavy chain. Antibodies can be divided into five major classes or isomers depending on whether they comprise α, δ, ε, γ, and μ heavy chains, respectively: IgA, IgD, IgE, IgG and IgM. Several major antibody classes can further be divided into subclasses, such as IgG1 (γ1 heavy chain), IgG2 (γ2 heavy chain), IgG3 (γ3 heavy chain), IgG4 (γ4 heavy chain), IgA1 (α1 heavy chain), IgA2 (α2 heavy chain), and the like.

The term "antigen-binding fragment" as used herein refers to an antibody fragment formed from an antibody portion comprising one or more CDRs, or any other antibody fragment that binds to an antigen but does not have an intact antibody structure. Examples of antigen-binding fragments include, but are not limited to, a diabody, Fab, Fab', F(ab')$_2$, a Fv fragment, a disulfide-stabilized Fv fragment (dsFv), (dsFv)$_2$, bispecific dsFv (dsFv-dsFv'), a disulfide-stabilized diabody (ds diabody), a single chain antibody molecule (scFv), a scFv dimer (a bivalent diabody), a bivalent single-chain antibody (BsFv), a multispecific antibody, a camelized single domain antibody, a nanobody, a domain antibody, and a bivalent domain antibody. The antigen-binding fragment can bind to the same antigen as the parent antibody. In some embodiments, the antigen-binding fragment may comprise one or more CDRs from a particular human antibody grafted to a framework region from one or more different human antibodies.

An "Fab" fragment of an antibody refers to a portion of antibody molecule consisting of one light chain (comprising the variable and constant regions), and one heavy chain variable and partial constant regions, which are bound together by disulfide bonds.

An "Fab"' fragment refers to a Fab fragment comprising a portion of hinge region.

"F(ab')$_2$" refers to a dimer of Fab.

An Fc fragment of antibody is responsible for a variety of different effector functions, such as ADCC and CDC, but is not involved in antigen binding.

An "Fv" fragment of antibody refers to a minimum antibody fragment that comprises the entire antigen binding site. An Fv fragment consists of a light chain variable region and a heavy chain variable region.

"Fusion protein" refers to a recombinant protein that genetically links a cDNA encoding a protein of interest to a cDNA encoding an antibody or antibody fragment, and is expressed in a eukaryotic or prokaryotic expression system.

"Linker" refers to a peptide chain consisting of 1-50 amino acids forming a peptide bond, or a derivative thereof, the N- and C-termini of which form a covalent bond with either the anti-OX40 antibody or the interferon, respectively, thereby binding the anti-OX40 antibody to the interferon. The anti-OX40 antibody and the interferon may be integrated by binding to the N-terminus or C-terminus of the interferon, respectively, at the C-terminus or N-terminus side of the heavy or light chain of the anti-OX40 antibody via a linker sequence or directly using a peptide bond. As a preferred embodiment of the fusion protein of interferon with anti-OX40 antibody, the following may be listed: a fusion protein obtained by binding the C-terminus of the heavy chain or light chain of the anti-OX40 antibody to the N-terminus of the interferon via a linker sequence; alternatively, a fusion protein obtained by binding the N-terminus of the heavy or light chain of the anti-OX40 antibody to the C-terminus of the interferon via a linker sequence.

"Single chain Fv antibody" or "scFv" refers to an engineered antibody formed by binding a light chain variable region to a heavy chain variable region directly or via a peptide chain (Huston et al., Proc. Natl. Acad. Sci. USA, 85:5879 (1988)).

"Single chain antibody Fv-Fc" or "scFv-Fc" refers to an engineered antibody consisting of scFv bound to an Fc fragment of antibody.

"Camelized single domain antibody", "heavy chain antibody" or "HCAb (Heavy-chain-only antibody)" all refers to an antibody comprising two VH domains and no light chain (Riechmann L. and Muyldermans S., J. Immunol. Methods 231(1-2):25-38 (1999); Muyldermans S., J. Biotechnol. 74(4):277-302 (2001); WO94/04678; WO94/25591; U.S. Pat. No. 6,005,079). Heavy chain antibodies were originally derived from the family Camelidae (camels, dromedaries and llamas). Despite the absence of light chain, camelized antibodies have a confirmed antigen binding repertoire (Hamers Casterman C. et al., Nature 363(6428):446-448 (1993); Nguyen V K. et al., "Heavy-Chain Antibodies in Camelidae: a Case of Evolutionary Innovation," Immunogenetics 54(1): 39-47 (2002); Nguyen V K. et al., Immunology 109(1):93-101 (2003)). The variable region (VH domain) of heavy chain antibody is the known minimum antigen binding unit produced by acquired immune (Koch-Nolte F. et al., FASEB J. 21(13):3490-3498. Epub (2007)).

"Nanobody" refers to an antibody fragment consisting of a VH domain and two constant regions CH2 and CH3 from an heavy chain antibody.

A "diabody" comprises a small antibody fragment with two antigen binding sites, wherein the fragment comprises a VH domain linked to a VL domain on the same polypeptide chain (see Holliger P. et al., *Proc. Natl. Acad. Sci. USA* 90(14):6444-6448 (1993); EP404097; WO93/11161). By using a linker that is too short to allow pairing between the two domains on the same chain, the two domains are forced to pair with the complementary domains of another chain and create two antigen-binding sites. The two antibody binding sites may targetedly bind to the same or different antigens (or antigenic epitopes).

"Domain antibody" refers to an antibody fragment that comprisres only one heavy chain variable region or one light chain variable region. In some cases, two or more VH domains are covalently bound by a polypeptide linker to form a bivalent domain antibody. The two VH domains of bivalent domain antibody may target the same or different antigens.

In some embodiments, "(dsFv)$_2$" comprises three peptide chains: two VH groups linked by a polypeptide linker and linked to two VL groups by disulfide bonds.

In some embodiments, a "bispecific ds diabody" comprises VL1-VH2 (linked by two polypeptide linkers) and VH1-VL2 (also linked by two polypeptide linkers), both of which are linked by disulfide bonds between VH1 and VL1.

A "bispecific dsFv" or "dsFv-dsFv" comprises three polypeptide chains: VH1-VH2 groups, the heavy chains of which are linked via a polypeptide linker (e.g., a long elastic linker) and are linked to the VL1 and VL2 groups via disulfide bonds, respectively; and each pair of heavy and light chains paired by disulfide bonds has a different antigen specificity.

In some embodiments, a "scFv dimer" is a bivalent diabody or a bivalent single-chain antibody (BsFv) comprising two dimerized VH-VL (linked by a polypeptide linker) groups, wherein the VH of the two groups cooperate with the VL of the other group to form two binding sites that can targetedly bind to the same antigen (or antigenic epitope) or to different antigens (or antigenic epitopes). In other embodiments, a "scFv dimer" is a bispecific diabody comprising interconnected VL1-VH2 (linked by a polypeptide linker) and VH1-VL2 (linked by a polypeptide linker), wherein VH1 cooperates with VL1, VH2 cooperates with VL2, and each cooperating pair has a different antigen specificity.

The term "fully human" as used herein, when used in reference to an antibody or antigen-binding fragment, refers to the antibody or antigen-binding fragment having or consisting of an amino acid sequence corresponding to the amino acid sequence of an antibody produced by a human or human immune cell, or derived from a non-human source such as a transgenic non-human animal utilizing a human antibody repertoire, or other sequences encoding human antibodies. In some embodiments, a fully human antibody does not comprise amino acid residues (particularly antigen-binding residues) derived from a non-human antibody.

The term "humanized" as used herein, when used in reference to an antibody or antigen-binding fragment, refers to an antibody or antigen-binding fragment that comprises CDRs derived from a non-human animal, FR regions derived from a human, and constant regions derived from a human (where applicable). Since a humanized antibody or antigen-binding fragment has a reduced immunogenicity, it can be used as a therapeutic agent for human in some embodiments. In some embodiments, the non-human animal is a mammal, such as mouse, rat, rabbit, goat, sheep, guinea pig, or hamster. In some embodiments, the humanized antibody or antigen-binding fragment consists essentially of human sequences, except that the CDR sequences are of non-human origin. In some embodiments, the human-derived FR regions may comprise the same amino acid sequence as the human antibody from which they are derived, or they may comprise some amino acid alterations, for example, no more than 10, 9, 8, 7, 6, 5, 4, 3, 2, or 1 amino acid alteration. In some embodiments, the amino acid alteration may be present only in the heavy chain FR region, only in the light chain FR region, or in both chains. In some preferred embodiments, the humanized antibody comprises human FR1-3 and human JH and JK.

As used herein, the term "chimeric" refers to an antibody or antigen-binding fragment having a portion of heavy and/or light chain derived from one species and the remainder of heavy and/or light chain derived from different species. In one illustrative example, the chimeric antibody may comprise a constant region derived from a human and a variable region derived from a non-human animal, such as mouse.

The term "OX40" refers to the receptor which binds to OX40L. It is a type I membrane protein belonging to the TNF receptor family, also named ACT-4, OX40L receptor, CD134 antigen, ACT35 antigen, or TNFRSF4. It has a molecular weight of 50 kDa and is registered in SwissProt with an accession number P43489.

As used herein, "human interferon" refers to a class of highly active, multifunctional secretory glycoproteins with antiviral, immunomodulatory, antitumor effects, and the like. It can be divided into type I, type II and type III IFNs according to the gene sequence, receptor specificity, and the like. The human type I IFN consists of 13 subtypes of IFNα, and IFNβ, IFNε, IFNκ and IFNω. Type I IFN has common cell surface receptor IFNAR composed of two subunits, namely IFNAR1 and IFNAR2. There is only one type II interferon, namely IFNγ. IFNγ has cell surface receptor IFNGR composed of two subunits, namely IFNGR1 and IFNGR2. Type III IFN consists of IFNλ1, IFNλ2, IFNλ3 and IFNλ4. The interferon in the fusion protein of the present application also includes interferon variants known in the art.

As used herein, "specific binding" refers to a non-random binding reaction between two molecules, such as the reaction between an antibody and an antigen. In some embodiments, the antibody or antigen-binding fragment thereof of the present application specifically binds to human and/or monkey OX40 with a binding affinity $(K_D) \leq 10^{-6}$ M. $K_D$ in this application refers to a ratio of the dissociation rate to the binding rate $(k_{off}/k_{on})$, which can be determined by surface plasmon resonance, for example using an instrument such as Biacore.

As used herein, "UMY02-L1" refers to a fusion protein having the heavy chain, the peptide linker and the human interferon as shown in SEQ ID NO:10, and the light chain as shown in SEQ ID NO:11, wherein the human interferon IFNα-2b as shown in SEQ ID NO:9 is linked to the carboxyl-terminus of the heavy chain via the peptide linker.

As used herein, "UMY02-L2" refers to a fusion protein having the heavy chain as shown in SEQ ID NO:12, and the light chain, the peptide linker and the human interferon as shown in SEQ ID NO:13, wherein the human interferon IFNα-2b as shown in SEQ ID NO:9 is linked to the carboxyl-terminus of the light chain via the peptide linker.

As used herein, "UMY02-L3" refers to a fusion protein having the heavy chain as shown in SEQ ID NO:14, and the light chain, the peptide linker and the human interferon as shown in SEQ ID NO: 13, wherein the human interferon IFNα-2b as shown in SEQ ID NO:9 is linked to the carboxyl-terminus of the light chain via the peptide linker.

As used herein, "MT01-C1" refers to a monoclonal antibody, which has the same VH (SEQ ID NO:7) and VL (SEQ ID NO:8) sequences as UMY02-L1, UMY02-L2 and UMY02-L3, and the heavy and light chain constant regions being human IgG1 and κ chain, respectively.

As used herein, "MT01-C1(G2)" refers to a monoclonal antibody, which has the same VH (SEQ ID NO:7) and VL (SEQ ID NO:8) sequences as UMY02-L1, UMY02-L2 and UMY02-L3, and the heavy and light chain constant regions being human IgG2 and κ chain, respectively.

As used herein, "MT01-L1" refers to a human-mouse chimeric antibody, which has the same heavy and light chain CDR sequences (SEQ ID NOs:1-6) as UMY02-L1, UMY02-L2 and UMY02-L3.

"MT01-C1", "MT01-C1 (G2)", and "MT01-L1" are from the Chinese Patent No. 201711476160.3, and their specific sequences are as shown in Table 2 and the Sequence Listing, all of which are incorporated herein by reference in their entirety.

The fusion protein UM06-L9 described in the present application consists of an antibody that specifically binds to human OX40 comprising the heavy chain as shown in SEQ ID NO:21 and the light chain as shown in SEQ ID NO:22, a peptide linker, and the human interferon IFNα-2a as shown in SEQ ID NO:20, wherein the human interferon IFNα-2a is linked to the carboxyl-terminus of the light chain of the antibody that specifically binds to human OX40 via a peptide linker GGGGS.

The fusion protein UM06-L9.1 described in the present application consists of an antibody that specifically binds to human OX40 comprising the heavy chain as shown in SEQ ID NO:21 and the light chain as shown in SEQ ID NO:23, a peptide linker, and the human interferon IFNα-2a as shown in SEQ ID NO:20, wherein the human interferon IFNα-2a is linked to the carboxyl-terminus of the light chain of the antibody that specifically binds to human OX40 via a peptide linker (GGGGS)$_2$.

The fusion protein UM 06-L18 described in the present application consists of an antibody that specifically binds to human OX40 comprising the heavy chain as shown in SEQ ID NO:21 and the light chain as shown in SEQ ID NO:27, a peptide linker, and the human interferon IFNα-2b mutant (T106A/L117A) as shown in SEQ ID NO:26, wherein the human interferon IFNα-2b mutant is linked to the carboxyl-terminus of the light chain of the antibody that specifically binds to human OX40 via a peptide linker (GGGGS)$_2$, and the amino acid sequence of the human interferon IFNα-2b is as shown in SEQ ID NO:9.

The fusion protein UM06-L20 as described in the present application consists of an antibody that specifically binds to human OX40 comprising the heavy chain as shown in SEQ ID NO:21 and the light chain as shown in SEQ ID NO:29, a peptide linker, and the human interferon IFNα-2b mutant (L117A) as shown in SEQ ID NO:28, wherein the human interferon IFNα-2b mutant is linked to the carboxyl-terminus of the light chain of the antibody that specifically binds to human OX40 via a peptide linker (GGGGS)$_2$.

The fusion protein UM06-L21 described in the present application consists of an antibody that specifically binds to human OX40 comprising the heavy chain as shown in SEQ ID NO:21 and the light chain as shown in SEQ ID NO:25, a peptide linker, and the human interferon IFNα-2a mutant (T106A/L117A) as shown in SEQ ID NO:24, wherein the human interferon IFNα-2a mutant is linked to the carboxyl-terminus of the light chain of the antibody that specifically binds to human OX40 via a peptide linker (GGGGS)$_2$.

As used herein, when applied to an amino acid sequence, "conservative substitution" refers to the substitution of one amino acid residue with another amino acid residue having a side chain with similar physical and chemical properties. For example, conservative substitution may be conducted among amino acid residues having a hydrophobic side chain (e.g., Met, Ala, VaL, Leu, and Ile), amino acid residues having a neutral hydrophilic side chain (e.g., Cys, Ser, Thr, Asn, and Gln), amino acid residues having an acidic side chain (e.g., Asp and Glu), amino acid residues having a basic side chain (e.g., His, Lys, and Arg), or amino acid residues having an aromatic side chain (e.g., Trp, Tyr and Phe). It is known in the art that a conservative substitution generally does not cause a significant change in the conformational structure of a protein, and thus is capable of retaining the biological activity of the protein.

When applied to an amino acid sequence (or a nucleic acid sequence), "percent sequence identity" refers to a percentage of amino acid (or nucleic acid) residues in a candidate sequence that are identical to those of a reference sequence, relative to the amino acid (or nucleic acid) residues in the candidate sequence during sequence alignment, and if necessary, after introducing gaps to maximize the number of identical amino acids (or nucleic acids). A conservative substitution of amino acid residue may or may not be considered as an identical residue. Percent sequence identity of amino acid (or nucleic acid) sequences can be determined by aligning sequences through tools disclosed in the art. A person skilled in the art may use the default parameters of the tools or adjust the parameters appropriately according to the needs of the alignment, for example by choosing an appropriate algorithm.

As used herein, "T cells" include CD4$^+$ T cells, CD8$^+$ T cells, T helper 1 cells, T helper 2 cells, T helper type 17 T cells, and suppressor T cells.

As used herein, "effector function" refers to a biological activity of Fc region of an antibody in binding to its effectors, e.g., C1 complex and Fc receptors. Exemplary effector functions include complement-dependent cytotoxicity (CDC) induced by the interaction between an antibody and Clq on a Cl complex, antibody-dependent cell-mediated cytotoxicity (ADCC) induced by the binding of Fc region of an antibody to the Fc receptors on effector cells, and phagocytosis.

As used herein, "cancer" or "cancerous condition" refers to any medical condition mediated by the growth, proliferation or metastasis of tumors or malignant cells and eliciting solid and non-solid tumors such as leukemia. A "tumor" in the present invention refers to a solid substance of tumor and/or malignant cells.

As used herein, "viral infection" refers to a pathogenic process in which viruses invade a human body through various pathways and proliferate in human cells, resulting in damage to the body, including chronic viral infections, such as viral infection of hepatitis B virus, hepatitis C virus, herpes virus, Epstein-Barr virus, HIV, cytomegalovirus, herpes simplex virus type I, herpes simplex virus type 2, human papilloma virus, or adenovirus, Kaposi's sarcoma-associated herpesvirus epidemics, and infection of Torquetenovirus, JC virus, or BK virus.

"Treatment" or "therapy" of a condition includes preventing or reducing the condition, reducing the rate of rise or development of the condition, reducing the risk of developing the condition, preventing or delaying the development of symptoms associated with the condition, reducing or terminating symptoms associated with the condition, causing a complete or partial reversal of the condition, curing the condition, or a combination thereof. For cancers, "treatment" or "therapy" may refer to inhibiting or slowing growth, proliferation or metastasis of tumors or malignant cells, or some combination thereof. For tumors, "treatment" or "therapy" includes clearing all or a portion of tumors, inhibiting or slowing growth and metastasis of tumors, preventing or slowing the development of tumors, or some combination thereof.

An "isolated" material has been artificially altered from its natural state. If an "isolated" substance or component occurs in nature, it has been altered or removed from its original state, or both. For example, a polynucleotide or polypeptide naturally occurring in a living animal is not isolated, but may be considered "isolated" if the polynucleotide or polypeptide is sufficiently isolated from the materials with which it coexists in its native state and exists in a sufficiently pure state. In some embodiments, the antibody and antigen-binding fragment are at least 90%, 93%, 95%, 96%, 97%, 98%, 99% pure as determined by electrophoresis (e.g., SDS-PAGE, isoelectric focusing, capillary electrophoresis), or chromatography (e.g., ion exchange chromatography or reverse phase HPLC).

A "vector" in the present invention refers to a vehicle into which a polynucleotide encoding a protein can be operably inserted for enabling the protein to be expressed. The vector can be used to transform, transduce or transfect a host cell, such that the genetic elements carried by the vector are expressed in the host cell. For example, the vectors include: plasmids, phagemids, cosmids, artificial chromosomes such as yeast artificial chromosome (YAC), bacterial artificial chromosome (BAC) or P1-derived artificial chromosome (PAC), bacteriophages such as k bacteriophage or M13 bacteriophage, animal viruses, and the like. Animal viral species used as vectors include retroviruses (including lentiviruses, adenoviruses, adeno-associated viruses, herpes viruses (e.g., herpes simplex viruses), poxviruses, baculoviruses, papillomaviruses, papovaviruses (e.g., SV40)). The vector may comprise a variety of elements that control expression, including a promoter sequence, a transcription initiation sequence, an enhancer sequence, a selection element, and a reporter gene. Further, the vector may also comprise an origin of replication. The vector may also comprise a component that facilitates the vetor to enter into cells, including, but not limited to, viral particle, liposome, or protein shell.

A "host cell" in the present invention refers to a cell into which an exogenous polynucleotide and/or a vector are introduced.

A "therapeutically effective amount" or an "effective dose" in the present invention refers to a dose or a concentration of a drug effective to treat a disease. For example, for the use of the antibody or antigen-binding fragment thereof disclosed herein, a therapeutically effective amount means that at that dose or concentration, the antibody or antigen-binding fragment can clear all or a portion of tumors, inhibit or slow the growth of tumors, inhibit metastasis of tumor cells, alleviate any symptoms or markers associated with tumors or cancerous conditions, prevent or delay the development of tumors or cancerous conditions, inhibit or eliminate viruses or virus infected cells, or some combination thereof.

"Pharmaceutically acceptable" means that the carrier, solvent, diluent, adjuvant, and/or salt referred to is generally chemically and/or physically compatible with the other ingredients in the formulation and physiologically compatible with the recipient.

Regarding the fusion protein of the present disclosure:

In some embodiments, exemplary fusion proteins comprise UMY02-L1, UMY02-L2, and UMY02-L3 are provided herein. In additional embodiments, exemplary fusion proteins comprise UM06-L9, UM06-L9.1, and UM06-L21. All the recited fusion proteins are specifically provided herein.

It will be appreciated by those skilled in the art that the foregoing CDR sequences may be modified to comprise one or more amino acid substitutions, thereby resulting in increased biological activities, e.g., an increased binding affinity to human OX40. For example, a library of antibody variants (e.g., Fab or FcFv variants) can be produced and expressed using phage display technique, followed by screening for the antibodies having affinity to human OX40. In another example, computer software can be used to simulate the binding of the antibody to human OX40 and identify the amino acid residues on the antibody that form a binding interface. Substitutions of these residues may be avoided to prevent a decrease in binding affinity, or these residues may be targeted for substitution to form a stronger binding. In some embodiments, at least one (or all) substitution in a CDR sequence is a conservative substitution.

In some embodiments, the fusion protein and antigen-binding fragment comprise one or more CDR sequences having at least 80% (e.g., at least 85%, 88%, 90%, 91%, 92%, 93%, 94%, 95%, 96%, 97%, 98%, or 99%) sequence identity with the sequences set forth for the exemplary fusion proteins UMY02-L1, UMY02-L2, UMY02-L3, UM06-L9, UM06-L9.1, UM06-L18, UM06-L20, and/or UM06-L21 provided herein, while retaining the binding affinity to human OX40 similar to or even higher than that of its parent antibody. The parent antibody has substantially the same sequence, but its corresponding CDR sequences have 100% sequence identity to the sequences listed.

In some embodiments, the fusion protein described herein is capable of specifically binding to human OX40 with a binding affinity ($K_D$) of $\leq 10^{-7}$ M, as measured by surface plasmon resonance. The binding affinity value can be expressed as a $K_D$ value, which is calculated as the ratio of the dissociation rate to the association rate ($k_{off}/k_{on}$) when the binding of an antigen to an antigen-binding molecule reaches an equilibrium. The antigen binding affinity (e.g., $K_D$) may be appropriately determined by any suitable methods known in the art, including, for example, a plasma resonance binding method using an instrument such as Biacore.

In some embodiments, the fusion protein described herein binds to human OX40 with an $EC_{50}$ (i.e., half binding concentration) of 10 ng/mL to 10 μg/mL. The binding of the antibody or the fusion protein to human OX40 can be determined by the methods known in the art, for example, sandwich methods such as ELISA, Western blot, FACS or other binding assays. In an illustrative example, an antibody to be tested (i.e., a primary antibody) is bound to immobilized human OX40 or cells expressing human OX40, followed by washing away unbound antibody and introducing a labeled secondary antibody that is capable of binding to the primary antibody, thus capable of detecting the bound secondary antibody. The detection can be performed on a microplate reader when immobilized OX40 is used, or can be performed using FACS assay when the cells expressing human OX40 are used.

In some embodiments, the fusion protein described herein binds to human OX40 with an $EC_{50}$ (i.e., 50% effective concentration) of 0.1 µg/mL to 10 µg/mL (determined using FACS assay).

In some embodiments, the fusion protein described herein may activate human OX40 signaling pathway by either FcR-mediated or interferon receptor-mediated mode, thus providing the biological activities, including, for example, inducing cytokine production by activated T cells (e.g., $CD4^+$ T cells and $CD8^+$ T cells), inducing proliferation of activated T cells (e.g., $CD4^+$ T cells and $CD8^+$ T cells), and reversing the inhibitory function of regulatory Treg.

The fusion protein is specific to human OX40. In some embodiments, the fusion protein does not bind to murine OX40, but binds to monkey OX40 with a binding affinity similar to that of human OX40. For example, the binding of the monoclonal antibody MT01-L1 with the same CDR sequences as the fusion protein of the present invention to mouse OX40 cannot be detected by conventional binding assay methods, such as FACS assay, while FACS detects that MT01-L1 binds to both monkey OX40 and human OX40.

In some embodiments, the fusion protein has a constant region of IgG2 isotype with reduced or eliminated effector functions. Effector functions such as ADCC and CDC can cause cytotoxicity to cells expressing OX40. Some normal cells are capable of expressing OX40. To avoid potentially undesirable toxicity to these normal cells, some embodiments of the of the present disclosure have reduced or even eliminated effector functions. A number of assays are known for assessing ADCC or CDC activity, such as Fc receptor binding assay, complement Clq binding assay, and cell lysis assay, which can be readily selected by those skilled in the art. Without wishing to be bound by theory, it is believed that the antibody having reduced or eliminated effector functions such as ADCC and CDC does not cause or minimize cytotoxicity to cells expressing OX40 (e.g., those normal cells), thus avoiding undesirable side effects.

In some embodiments, the fusion protein described herein has an extended duration of action in an organism than an interferon molecule. This is because the fusion protein has a longer half-life and drug retention time in animals. This property is beneficial to reducing the number of medications by patients and improving the efficacy of drugs.

In some embodiments, the fusion protein described herein has reduced side effects. For example, the anti-OX40 antibody and antigen-binding fragment thereof may have a fully human IgG sequence and therefore be less immunogenic than a humanized antibody. As another example, the fusion protein and antigen-binding fragment thereof may have the form of IgG2 or IgG4 to eliminate ADCC and CDC.

In some embodiments, the fusion protein described herein is advantageous in that it can be used in combination with immunogenic substances, such as tumor cells, purified tumor antigens, and the cells transfected with the encoded immunostimulatory factors, and tumor vaccines. In addition, the anti-OX40 antibody and antigen-binding fragment thereof may be included in combination therapies, including standard chemotherapy and radiation therapy, target-based small molecule therapy, and other emerging immune checkpoint modulator therapy. In some embodiments, the antibody and antigen-binding fragment thereof can be used as a basic molecule for an antibody-drug conjugate, and a bispecific or multivalent antibody.

In some embodiments, the fusion protein or antigen-binding fragment thereof described herein is a camelized single chain domain antibody, a diabody, a scFv, a scFv dimer, BsFv, dsFv, $(dsFv)_2$, dsFv-dsFv', a Fv fragment, Fab, Fab', $F(ab')_2$, a ds diabody, a nanobody, a domain antibody, or a bivalent domain antibody.

In some embodiments, the fusion protein described herein comprises an immunoglobulin constant region. In some embodiments, the immunoglobulin constant region comprises a heavy chain and/or a light chain constant region. The heavy chain constant region comprises a CH1, CH1-CH2 or CH1-CH3 region. In some embodiments, the immunoglobulin constant region may further comprise one or more modifications to achieve the desired properties. For example, the constant region may be modified to reduce or eliminate one or more effector functions to enhance FcRn receptor binding or to introduce one or more cysteine residues.

In some embodiments, the antibody and antigen-binding fragment thereof further include conjugates. It is contemplated that the antibody or antigen-binding fragment thereof of the present invention may be linked to a variety of conjugates (see, e.g., "Conjugate Vaccines", Contributions to Microbiology and Immunology, J. M. Cruse and R. E. Lewis. Jr. (eds.), Carger Press, New York (1989)). These conjugates may be linked to the antibody or antigen conjugate by covalent binding, affinity binding, intercalation, coordinate binding, complexation, binding, mixing, addition, or other means. In some embodiments, the antibody and antigen-binding fragment disclosed herein can be engineered to contain specific sites other than epitope-binding moieties that can be used to bind one or more conjugates. For example, such sites may comprise one or more reactive amino acid residues, such as cysteine residues and histidine residues, to facilitate covalent attachment to the conjugate. In some embodiments, the antibody may be linked to the conjugate indirectly, or via another conjugate. For example, the antibody or antigen-binding fragment thereof can bind to biotin and then indirectly bind to a second conjugate, which is linked to avidin. The conjugate may be a detectable label, a pharmacokinetically modified moiety, a purified moiety, or a cytotoxic moiety. Examples of detectable labels may include fluorescent labels (e.g., fluorescein, rhodamine, dansyl, phycoerythrin or Texas red), enzyme substrate labels (e.g., horseradish peroxidase, alkaline phosphatase, luciferase, glucoamylase, lysozyme, glucose oxidase or R-D galactosidase), stable or radioactive isotopes, chromophore moieties, digoxin, biotin/avidin, DNA molecules or gold for detection. In some embodiments, the conjugate may be a pharmacokinetically modified moiety, such as PEG, which helps to extend the half-life of the antibody. Other suitable polymers include, for example, carboxymethylcellulose, dextran, polyvinyl alcohol, polyvinylpyrrolidone, and ethylene glycol/propylene glycol copolymers, and the like. In some embodiments, the conjugate may be a purified moiety, such as a magnetic bead. A "cytotoxic moiety" can be any agent that is harmful to a cell or that may damage or kill a cell. Examples of cytotoxic moieties include, but are not limited to, paclitaxel, cytochalasin B, gramicidin D, ethidium bromide, emetine, mitomycin, etoposide, teniposide, vincristine, vinblastine, colchicine, doxorubicin, daunorubicin, dihydroxyanthraquinone, mitoxantrone, mithramycin, actinomycin D, 1-dehydrotestosterone, glucocorticoids, procaine, tetracaine, lidocaine, propranolol, puromycin and analogue thereof, antimetabolites (e.g., methotrexate, 6-mercaptopurine, 6-thioguanine, cytarabine, 5-fluorouracil, dacarbazine), alkylating agents (e.g., nitrogen mustard, thiotepa, chlorambucil, melphalan, carmustine (BSNU) and lomustine (CCNU), cyclophosphamide, busulfan, dibromomannitol, streptozotocin, mitomycin C and cis-dichlorodiamine platinum (DDP), cisplatin, anthracycline antibiotics (e.g., daunorubicin (formerly daunomycin) and doxorubicin), antibiotics (e.g., dactinomycin (formerly known as actinomycin), bleomycin, mithramycin, and ampicillin (AMC)), and antimitotic agents (e.g., vincristine and vinblastine).

Polynucleotide and Recombinant Method

Amino acid sequences of the fusion protein of the present application may be converted to corresponding DNA coding sequences using genetic engineering techniques well known in the art. Due to the degeneracy of genetic code, the transformed DNA sequences may not be completely identical, while the encoded protein sequences remain unchanged.

A vector comprising a polynucleotide encoding the fusion protein may be introduced into a host cell for cloning (amplification of DNA) or gene expression using recombinant techniques well known in the art. In another embodiment, the fusion protein can be prepared by homologous recombination methods well known in the art. A variety of vectors are available. The vector components typically include, but is not limited to, two or more selected from the group consisting of: a signal sequence, an origin of replication, one or more marker genes, an enhancer sequence, a promoter (for example: SV40, CMV, EF-1a), and a transcription termination sequence.

In some embodiments, the vector systems include mammalian, bacterial, and yeast systems, and will include plasmids such as, but not limited to, pALTER, pBAD, pcDNA, pCal, pL, pELpGEMEX, pGEX, pCLpCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pProl8, pTD, pRS420, pLexA, pACT2, and other vectors available from the laboratory or commercially available vectors. Suitable vectors may include plasmid or viral vectors (e.g., replication-defective retroviruses, adenoviruses, and adeno-associated viruses).

A vector comprising a polynucleotide encoding the fusion protein may be introduced into a host cell for cloning or gene expression. Host cells suitable for cloning or expressing the DNA in the vectors of the present invention are prokaryotic, yeast or the above-mentioned advanced eukaryotic cells. Prokaryotic cells suitable for use in the present invention include eubacteria, such as gram-negative or gram-positive bacteria, for example, Enterobacteriaceae such as *E. coli*, *Enterobacter*, *Erwinia*, *Klebsiella*, *Proteus*, *Salmonella* such as *Salmonella typhimurium*; *Serratia* such as *Serratia marcescens*, *Shigella*, and *Bacillus* such as *Bacillus subtilis* and *Bacillus licheniformis*, *Pseudomonas* such as *Pseudomonas aeruginosa*, and Streptomycetes.

In addition to prokaryotic cells, eukaryotic microorganisms such as filamentous fungi or yeasts can also be used as host cells for cloning or expressing vectors encoding the fusion protein. *Saccharomyces cerevisiae* or baker's yeast is the most commonly used lower eukaryotic host microorganism. However, many other genera, species and strains are common and suitable for use in the present invention, such as *Schizosaccharomyces pombe*; *Kluyveromyces* hosts, such as *Kluyveromyces lactis*, *Kluyveromyces fragilis* (ATCC 12, 424), *Kluyveromyces bulgaricus* (ATCC 16, 045), *Kluyveromyces wickerhamii* (ATCC 24, 178), *Kluyveromyces waltii* (ATCC 56, 500), *Kluyveromyces drosophila* (ATCC 36, 906), *Kluyveromyces* thermotolerant and *Kluyveromyces marxianus*; *Yarrowia lipolytica* (EP 402, 226); *Pichia pastoris* (EP 183, 070); *Candida*; *Trichoderma reesei* (EP 244, 234); *Neurospora*; *Schwanniomyces occidentalis*, such as *Schwanniomyces occidentalis*; and filamentous fungi, such as *Neurospora*, *Penicillium*, *Curvularia* and *Aspergillus*, such as *Aspergillus nidulans* and *Aspergillus niger*.

The host cells suitable for expressing the glycosylated antibody or antigen-binding fragment thereof provided herein are derived from multicellular organisms. Examples of invertebrate cells include plant and insect cells. A variety of baculoviral strains and variants thereof and corresponding permissive insect host cells have been found, which are derived from hosts, such as *Spodoptera frugiperda* (caterpillar), *Aedes aegypti* (mosquito), *Aedes albopictus* (mosquito), *Drosophila melanogaster* (*drosophila*) and *Bombyx mori*. A variety of viral strains for transfection are publicly available, such as *Autographa californica* nuclear polyhedrosis virus and Bm-5 variants of *Bombyx mori* nuclear polyhedrosis virus, all of which can be used in the present invention, particularly for transfecting *Spodoptera frugiperda* cells. The plant cell cultures of cotton, corn, potato, soybean, *petunia*, tomato and tobacco can also be used as the hosts.

However, the most interesting host cells are vertebrate cells, and the culture of vertebrate cells (tissue culture) has become a routine practice. Examples of available mammalian host cells include monkey kidney CV1 line transformed by SV40 (COS-7, ATCC CRL 1651); human embryonic kidney cell line (293 or 293 cell subclone in suspension culture, Graham et al., *Gen. Virol.* 36:59 (1977)); baby hamster kidney cells (B blood, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); Buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells (Mather et al., *Annals N. Y. Acad. Sci.* 383:44-68 (1982)); MRC5 cells; FS4 cells; and human hepatoma cell line (HepG2). In some preferred embodiments, the host cell is 293F cell.

The host cell is transformed with the above-mentioned expression or cloning vector that can produce the fusion protein, and then cultured in a conventional nutrient medium, which is suitable for inducing promoters, selecting transformed cells, or amplifying genes encoding target sequences after being modified.

The host cells used to produce the fusion protein in the present invention can be cultured in a variety of media known in the art. The media may also comprise any other necessary additives known in the art in a suitable concentration. The conditions of the media, such as temperature, pH and the like are those selected previously for expression of host cell, which are well known to those of ordinary skill.

When recombinant techniques are used, the antibody may be produced in the intracellular and periplasmic space, or directly secreted into the culture medium. If the antibody is produced intracellularly, the particulate debris of host cells or lysed fragments is first removed, for example, by centrifugation or sonication. Carter et al., *Bio/Technology* 10:163-167 (1992) describes a method for isolating an antibody secreted into the *E. coli* periplasmic space. Briefly, cell paste was thawed in the presence of uranyl acetate (pH 3.5), EDTA and phenylmethylsulfonyl fluoride (PMSF) for more than about 30 minutes. The cell debris was removed by centrifugation. If the antibody is secreted into the culture medium, the supernatant of expression system is typically first concentrated using a commercially available protein concentration filter, such as an Amicon or Millipore Pellicon ultrafiltration unit. In any of the foregoing steps, protease inhibitors such as PMSF may be added to inhibit protein degradation, and antibiotics may be added to prevent the growth of incidental contaminants.

Antibodies produced from the cells may be purified using purification methods such as hydroxyapatite chromatography, gel electrophoresis, dialysis, DEAE-cellulose ion exchange chromatography columns, ammonium sulfate precipitation, salting out, and affinity chromatography, wherein affinity chromatography is a preferred purification technique. The types of the antibody and the presence of any immunoglobulin Fc domain in the antibody determine whether protein A is suitable as an affinity ligand. Protein A can be used to purify antibodies based on human γ1, γ2 or γ4 heavy chain (Lindmark et al., *J. Immunol. Meth.* 62:1-13 (1983)). Protein G is suitable for all murine isomers and human γ3 (Guss et al., *EMBO J.* 5:1567-1575 (1986)). Agarose is the most commonly used matrix to which affinity ligands are attached, but other matrix may also be used. Mechanically stable matrix, such as glass with a controlled porosity or poly(styrene)benzene can achieve a faster flow rate and a shorter processing time than agarose. If the antibody comprises a CH3 domain, it can be purified using, for example, Bakerbond ABX. TM resin (J. T. Baker, Phillipsburg, N. J.). Other techniques for protein purification, such as fractionation in ion exchange columns, ethanol precipitation, reverse phase HPLC, silica gel chromatography, heparin agarose gel chromatography based on anion or cation exchange resin (e.g., polyaspartic acid columns), chromatofocusing, SDS-PAGE, and ammonium sulfate precipitation, may also be determined according to the antibody obtained as desired.

After any preliminary purification steps, the mixture containing the antibody of interest and impurities can be processed by a low pH hydrophobic interaction chromatography using an elution buffer with a pH of about 2.5-4.5, preferably at a low salt concentration (for example, from about 0 to 0.25 M salt concentration).

Kit

The application provides a kit containing the fusion protein. In some embodiments, the kit is used to detect the presence or level of OX40 in a biological sample. The biological sample may include cells or tissue.

In some embodiments, the kit contains a fusion protein conjugated to a detectable label. In some embodiments, the kit contains an unlabeled fusion protein, and further contains a labeled secondary antibody that can bind to the unlabeled fusion protein. The kit may further contain instructions for use and a package separating each component in the kit.

In some embodiments, the fusion protein is connected to a substrate or an instrument for a sandwich assay such as ELISA, or immunochromatographic assay.

Suitable substrates or instruments may be, for example, microplates and test papers.

Pharmaceutical Composition and Therapeutic Method

The present application further provides a pharmaceutical composition comprising the fusion protein and one or more pharmaceutically acceptable carriers.

The pharmaceutically acceptable carriers for use in the pharmaceutical composition disclosed herein may include, for example, pharmaceutically acceptable liquids, gels, or solid carriers, aqueous media, non-aqueous media, antimicrobial materials, isotonic materials, buffers, antioxidants, anesthetics, suspending/dispersing agents, integrating agents, diluents, adjuvants, excipients, or nontoxic auxiliary substances, other components known in the art, or various combinations thereof.

Suitable components may include, for example, antioxidants, fillers, binders, disintegrating agents, buffers, preservatives, lubricants, flavoring agents, thickening agents, coloring agents, emulsifying agents, or stabilizing agents such as sugars and cyclodextrins. Suitable antioxidants may include, for example, methionine, ascorbic acid, EDTA, sodium thiosulfate, platinum, catalase, citric acid, cysteine, mercaptoglycerol, thioglycolic acid, mercaptosorbitol, butyl methylanisole, butylated hydroxytoluene, and/or propyl gallate. The inclusion of one or more antioxidants, such as methionine, in a composition comprising the fusion protein disclosed herein will reduce the oxidation of the fusion protein. Decreased oxidation may prevent or reduce the decrease in binding affinity, thereby improving antibody stability and extending shelf life.

Further, pharmaceutically acceptable carriers may include, for example, aqueous media such as sodium chloride injection, Ringer's solution injection, isotonic dextrose injection, sterile aqueous injection, or dextrose and lactated Ringer's solution, non-aqueous media such as plant-derived fixed oil, cottonseed oil, corn oil, sesame oil, or peanut oil, antibacterial substances at a bacteriostatic or fungistatic concentration, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcellulose, hydroxypropylmethylcellulose or polyvinylpyrrolidone, emulsifying agents such as polysorbate 80 (Tween-80), integrating agents such as EDTA (ethylenediaminetetraacetic acid) or EGTA (ethyleneglycol bis(2-aminoethylether)tetraacetic acid), ethanol, polyethylene glycol, propylene glycol, sodium hydroxide, hydrochloric acid, citric acid or lactic acid. Antibacterial agents can be added to a pharmaceutical composition in a multi-dose container, which include phenols or cresol, mercury formulations, benzyl alcohol, chlorobutanol, methyl and propyl para-hydroxybenzoate, merthiolate, benzalkonium chloride, and chlorophenethylamine. Suitable adjuvants may include, for example, water, salt, glucose, glycerol or ethanol. Suitable nontoxic auxiliary substances may include, for example, emulsifying agents, pH buffering agents, stabilizing agents, solubilizing agents, or substances such as sodium acetate, sorbitan laurate, triethanolamine oleate, or cyclodextrins.

The pharmaceutical composition may be a liquid solution, a suspension, an emulsion, a pill, a capsule, a tablet, a sustained release formulation, or a powder. An oral formulation may comprise standard carriers, such as pharmaceutical grade mannitol, lactose, starch, magnesium stearate, polyvinylpyrrolidone, sodium saccharin, cellulose, magnesium carbonate, and and the like.

In some embodiments, the pharmaceutical composition is formulated as an injectable composition. The injectable pharmaceutical composition may be prepared into any conventional form, for example, a liquid solution, a suspension, an emulsion, or a solid form suitable for production of a liquid solution, suspension, or emulsion. The injectable preparations may include a ready-to-use sterile and/or pyrogen-free solution, a sterile and dried soluble which is combined with a solvent immediately prior to use, such as a lyophilized powder, and can also include a subcutaneous tablet, a sterile suspension ready for injection, a sterile and dried insoluble product which is combined with a vehicle immediately prior to use, and a sterile and/or pyrogen-free emulsion. The solvent may be aqueous or non-aqueous.

In some embodiments, a unit dose of injectable preparation is packaged in an ampoule, a tube, or a syringe with a needle. It is known in the art that all formulations for injectable administration should be sterile and pyrogen-free.

In some embodiments, sterile lyophilized powders can be prepared by dissolving the fusion protein disclosed herein in an appropriate solvent. The solvent may comprise at least one other pharmacological component that can increase the stability of the powder or a reconstituted solution prepared from the powder, or that improve the powder or the reconstituted solution. Suitable adjuvants include, but are not limited to, water, glucose, sorbitol, fructose, corn syrup, xylitol, glycerol, glucose, brown sugar, or other suitable substances. The solvent may comprise a buffer, such as citric acid buffer, sodium or potassium phosphate buffer, or other buffers known to those skilled in the art. In one embodiment, the pH of the buffer is neutral. The solution is then filtered and sterilized under standard conditions well known in the art, followed by lyophilization to produce a desired formulation. In one embodiment, the resulting formulation is subpackaged into vials and lyophilized. Each vial may contain a single dose or multiple doses of the fusion protein. The loading in each vial may be slightly higher than that required for each dose or multiple doses (e.g., 10% overdose) to ensure accurate sampling and administration. The lyophilized powder may be stored under suitable conditions, such as in a range of about 4° C. to room temperature.

In one embodiment the lyophilized powder is re-dissolved with water for injection to obtain a formulation for administration by injection. In one embodiment, the lyophilized powder may be re-dissolved by being added into sterile and pyrogen-free water or other suitable liquid carrier. The precise amount is determined by the therapy chosen and may be determined with empirical value.

A method of treatment is also provided, comprising administering to a subject in need thereof a therapeutically effective amount of the fusion protein described herein.

The therapeutically effective dosage of the fusion protein provided herein will depend upon a variety of factors well known in the art, such as body weight, age, past medical history, current therapy, the health of the subject and the potential for cross-infection, allergies, hypersensitivity, and side effects, as well as the route of administration and the extent of tumor development. Those skilled in the art (e.g., a physician or a veterinarian) can proportionally reduce or increase the dosage according to these or other conditions or requirements.

In some embodiments, the fusion protein provided herein may be administered at a therapeutically effective dose of between about 0.01 mg/kg and about 100 mg/kg. In some embodiments, the fusion protein is administered at a dose of about 50 mg/kg or less, and in some embodiments at a dose of 10 mg/kg or less, 5 mg/kg or less, 1 mg/kg or less, 0.5 mg/kg or less, or 0.1 mg/kg or less. A particular dose may be administered at multiple intervals, for example, once a day, twice or more a day, twice or more a month, once a week, once every two weeks, once every three weeks, once a month, or once every two months or more months. In some embodiments, the dosage administered may vary with the course of the treatment. For example, in some embodiments, the initial dose administered may be higher than the subsequent dose administered. In some embodiments, the dosage administered is adjusted over the course of treatment according to the response of the subject being administered.

The dosage regimen may be adjusted to achieve an optimal response (e.g., a therapeutic response). For example, administration may be conducted in a single dose or in multiple divided doses over two periods of time.

The fusion protein disclosed in the present invention may be administered by the administration modes well-known in the art, for example, by injection (e.g., subcutaneous injection, intraperitoneal injection, intravenous injection including intravenous drip, intramuscular injection, or intradermal injection) or non-injection (e.g., oral administration, nasal administration, sublingual administration, rectal administration, or topical administration).

In some embodiments, the fusion protein is used for treating conditions associated with its molecular mechanisms, including tumors and cancers, for example, non-small cell lung cancer, small cell lung cancer, renal cell cancer, colorectal cancer, ovarian cancer, breast cancer, pancreatic cancer, gastric cancer, bladder cancer, esophageal cancer, mesothelioma, melanoma, head and neck cancer, thyroid cancer, sarcoma, prostate cancer, glioblastoma, cervical cancer, thymic carcinoma, leukemia, lymphoma, myeloma, mycoses fungoids, Merkel-cell carcinoma and other hematological malignancies such as classical Hodgkin's lymphoma (CHL), primary mediastinal large B-cell lymphoma, T-cell/histiocyte B-cell-rich lymphoma, EBV positive and negative PTLD and EBV-associated diffuse large B-cell lymphoma (DLBCL), plasmablastic lymphoma, extranodal NK/T-cell lymphoma, nasopharyngeal carcinoma and HHV 8-associated primary exudative lymphoma, Hodgkin's lymphoma, central nervous system (CNS) tumors, such as primary CNS lymphoma, spinal tumors, and brain stem glioma. In some embodiments, the conditions treated by the fusion protein include chronic viral infections, such as viral infection of hepatitis B virus, hepatitis C virus, herpes virus, Epstein-Barr virus, HIV, cytomegalovirus, herpes simplex virus type I, herpes simplex virus type 2, human papilloma virus, or adenovirus, Kaposi's sarcoma-associated herpesvirus epidemics, and infection of Torquetenovirus, JC virus, or BK virus.

Method of Application

The present application further provides a method of using the fusion protein.

In some embodiments, the present application provides a method of treating diseases or conditions associated with the mechanisms of the fusion protein in an individual, comprising administering a therapeutically effective amount of the fusion protein described herein.

The fusion protein disclosed herein may be administered alone or in combination with one or more other therapeutic means or agents. For example, the fusion protein disclosed herein may be used in combination with chemotherapy, radiation therapy, cancer treatment surgery (e.g., tumor resection), an anti-viral drug, one or more anti-emetic agents or other therapies for chemotherapy-induced complications, or any other therapeutic agent for cancers or viruses. In some such embodiments, the fusion protein disclosed herein, when used in combination with one or more therapeutic agents, may be administered simultaneously with the one or more therapeutic agents, and in some such embodiments, the fusion protein may be administered simultaneously as a part of the same pharmaceutical composition. However, the fusion protein "in combination" with other therapeutic agent need not be administered simultaneously or in the same composition comprising the therapeutic agent. The meaning of "in combination" in the present invention also includes that a fusion protein administered before or after another therapeutic agent, which is also considered to be "in combination" with the therapeutic agent, even if the fusion protein and the second agent are administered by different administration modes. Where possible, other therapeutic agent for use in combination with the fusion protein disclosed herein may be administered according to the methods described in the manufacturer's instructions for such other therapeutic agent, or according to Physicians' Desk Reference 2003 (Physicians' Desk Reference, 57th Ed; Medical Economics Company; ISBN: 1563634457; 57th Ed (2002.11)), or according to other methods known in the art.

In some embodiments, the therapeutic agent is capable of inducing or enhancing an immune response to cancers. For example, tumor vaccines may be used to induce an immune response to certain tumors or cancers. Cytokine therapy may be used to enhance the presentation of tumor antigen to the immune system. Examples of cytokine therapy include, but are not limited to, interferons such as interferon α, β and γ, colony stimulating factors such as macrophage CSF, granulocyte macrophage CSF and granulocyte CSF, interleukins such as IL-1, IL-1a, IL-2, IL-3, IL-4, IL-5, IL-6, IL-7, IL-8, IL-9, IL-10, IL-11, and IL-12, tumor necrosis factors such as TNF-α and TNF-β. Agents that inactivate immunosuppressive targets, such as PD-L1/PD-1 antibodies, TGF-β inhibitors, IL-10 inhibitors, and Fas ligand inhibitors, may also be used. Another group of agents include those that activate an immune response against tumor or cancer cells, for example, those that improve T cell activation (e.g., T cell costimulatory molecule agonists such as CTLA-4, ICOS), and those that increase dendritic cell functions and antigen presentation.

The following examples are intended to better illustrate the present invention, and should not be construed as limiting the scope of the present invention. All of the specific compositions, materials, and methods described below, as a whole or a part, are within the scope of the present invention. These specific compositions, materials, and methods are not intended to limit the present invention, but are merely illustrative of the specific embodiments within the scope of the present invention. Equivalent compositions, materials and methods may be developed by those skilled in the art without addition of inventive effort and without departing from the scope of the present invention. It will be appreciated that various modifications made to the method of the present invention may still fall within the scope of the present invention. The inventors intend to include such variations within the scope of the present invention.

Example 1: Preparation of a Fusion Protein Comprising an Anti-OX40 Antibody and Human Interferon α-2b This example illustrates the design and expression of several anti-OX40 antibody-human interferon α-2b fusion proteins, wherein the heavy and light chain sequences of the anti-human OX40 activating antibodies were derived from MT01-C1 or MT01-C1 (G2) in the Chinese Patent No. 201711476160.3, wherein "MT01-C1" refers to a monoclonal antibody having the same VH (SEQ ID NO:7) and VL (SEQ ID NO:8) sequences as UMY02-L1, UMY02-L2 and UMY02-L3, the heavy and light chain constant regions of which are human IgG1 and κ chain, respectively. "MT01-C1(G2)" refers to a monoclonal antibody having the same VH (SEQ ID NO:7) and VL (SEQ ID NO:8) sequences as UMY02-L1, UMY02-L2 and UMY02-L3, the heavy and light chain constant regions of which are human IgG2 and κ chain, respectively.

The interferon IFNα-2b sequence was taken from the human interferon IFNα-2b (NP_000596.2), the amino acid sequence of which is as shown in SEQ ID NO:9.

The structural design of exemplary fusion proteins are as shown in FIG. 1. In FIG. 1, "UMY02-L1" refers to a fusion protein having the heavy chain, the peptide linker and the human interferon as shown in SEQ ID NO:10, and the light chain as shown in SEQ ID NO:11, wherein the human interferon IFNα-2b as shown in SEQ ID NO:9 is linked to the carboxyl-terminus of the heavy chain by the peptide linker; "UMY02-L2" refers to a fusion protein having the heavy chain as shown in SEQ ID NO:12, and the light chain, the peptide linker and the human interferon as shown in SEQ ID NO:13, wherein the human interferon IFNα-2b as shown in SEQ ID NO:9 is linked to the carboxyl-terminus of the light chain by the peptide linker; "UMY02-L3" refers to a fusion protein having the heavy chain as shown in SEQ ID NO:14, and the light chain, the peptide linker and the human interferon as shown in SEQ ID NO:13, wherein the human interferon IFNα-2b as shown in SEQ ID NO:9 is linked to the carboxyl-terminus of the light chain via the peptide linker.

The cDNA sequences encoding the heavy and light chains of the antibodies of the fusion proteins were cloned into the mammalian cell expression vector pcDNA 3.4, respectively. The heavy chain expression plasmids and light chain expression plasmids were transfected into HEK 293 cells with Lipofectamine™ 2000 transfection reagent (Invitrogen) at a molar ratio of 2:1, and cultured for 7 days at 37° C. and 5% carbon dioxide. The supernatants were collected, and the antibodies in the supernatants were purified by Protein A affinity chromatography. The purified antibodies were dialyzed against PBS solution, concentrated by lyophilization and stored at −20° C.

Example 2: ELISA Binding Assay

A 96-well high affinity plate was coated with 1 μg/mL human OX40 protein solution at 100 μL/well and shaken overnight at 4° C. The next day, the plate was first washed 3 times with 300 μL PBST (Tween 20: 0.5% c), then blocked with 5% BSA/PBS at 100 μL/well for 2 h, and shaken at room temperature, followed by washing 3 times with 300 μL PBST. Gradient dilutions of the fusion protein samples were prepared in PBS, and then added to the 96-well plate at 100 μL/well; the plate was shaken for 1 h at room temperature, followed by washing 3 times with 300 μL PBST. A secondary antibody goat-anti-human IgG HRP solution was prepared and added to the 96-well plate at 100 μL/well, and the plate was shaken for 1 h at room temperature, followed by washing 4 times with 300 μL PBST. TMB was added at 100 μL/well to develop color for 20 min. 0.6N $H_2SO_4$ was added at 100 μL/well to stop the color development, and the OD values were determined at 450 nm.

Figure 2:
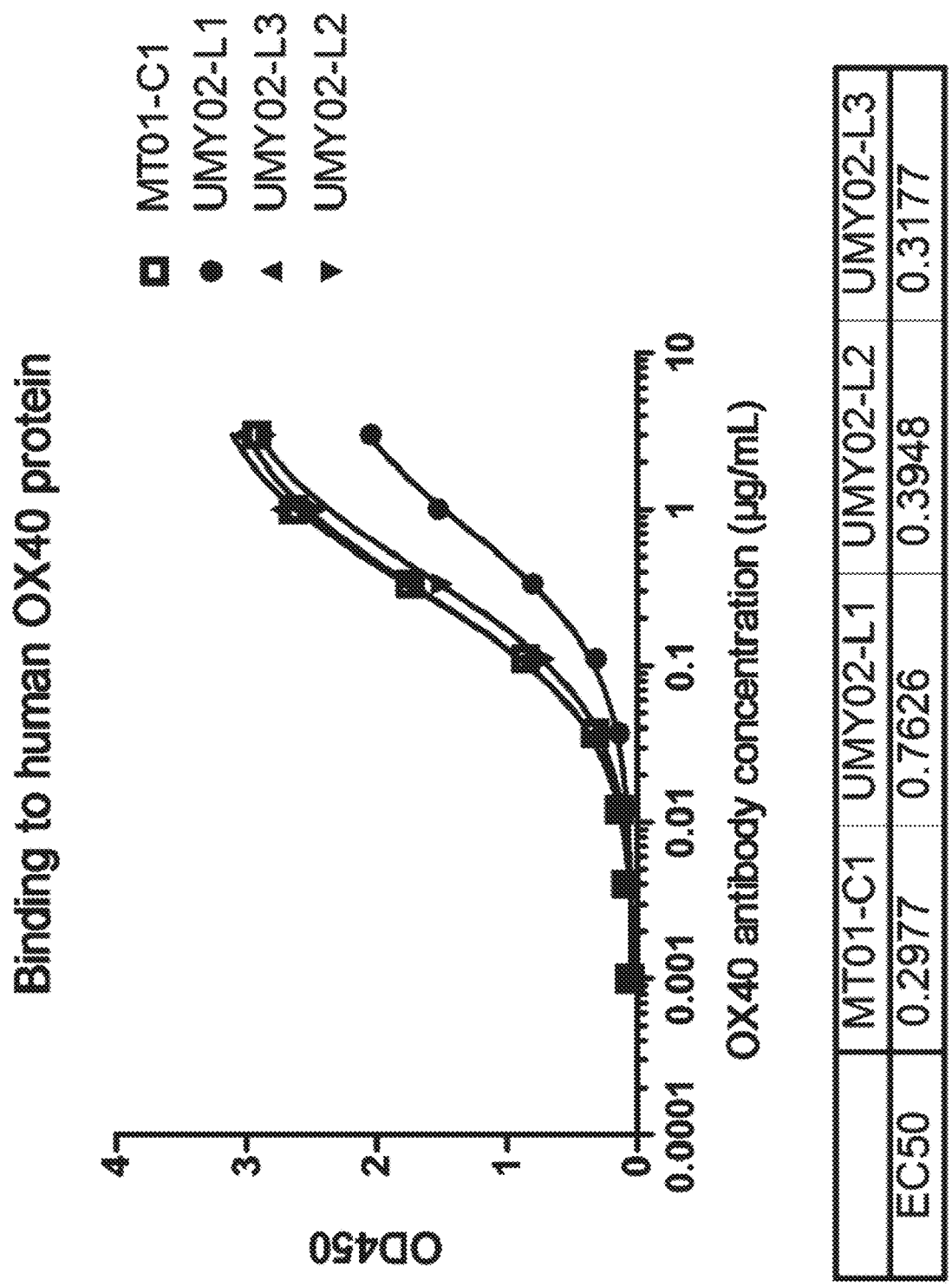
FIG. 2 shows the results of ELISA binding assay of the fusion proteins according to the present invention to human OX40 protein.

After testing, the results are shown in FIG. 2. The $EC_{50}$ of the fusion proteins UMY02-L1, UMY02-L2, and UMY02-L3 for ELISA binding were 0.7626, 0.3948, and 0.3177 μg/mL, respectively, all of which were equivalent to $EC_{50}$ (0.2977 μg/mL) of the OX40 antibody MT01-C1 (FIG. 2).

Example 3: Binding to Human, Cynomolgus Monkey and Mouse OX40 (FACS)

Figure 3:
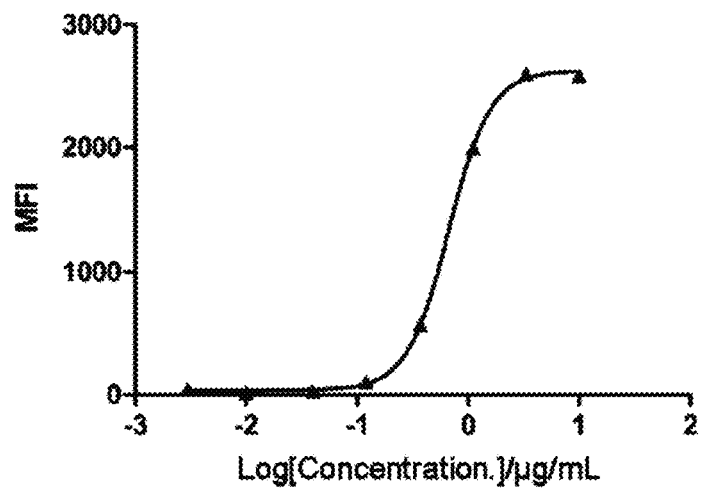
FIG. 3 shows the FACS assay results showing that the MT01-L1 antibody binds to both human and Cynomolgus monkey OX40, but not to mouse OX40.
Figure 3:
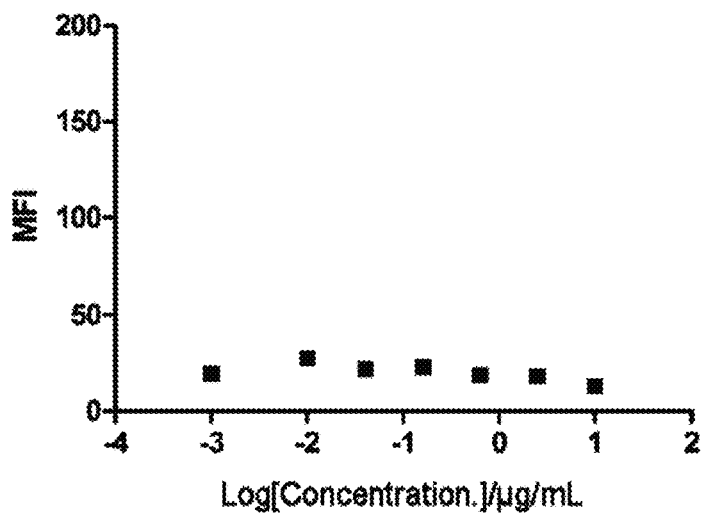
Figure 3:
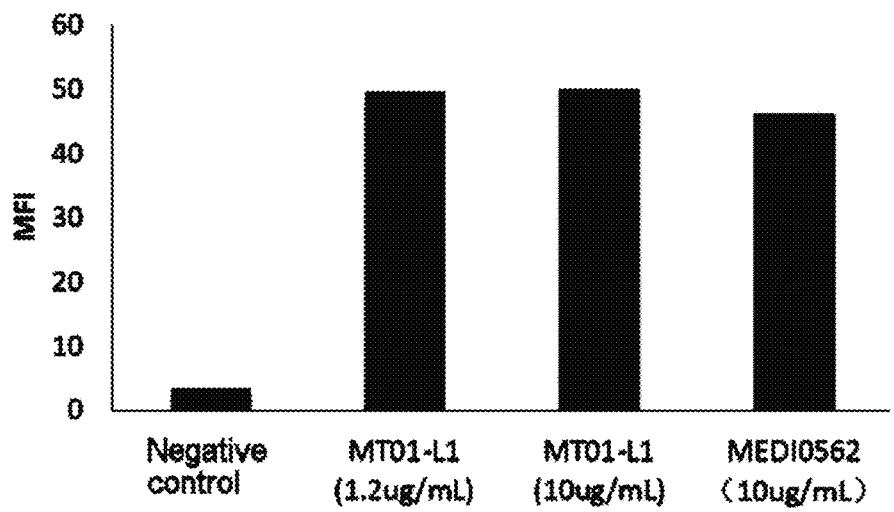

CHO cells were transfected with an expression plasmid encoding human, cynomolgus or mouse OX40 protein and cultured for 48 h. The solutions of the OX40 antibody MT01-L1 having a concentration gradient were prepared with PBS, each of which being a working solution of 10× final concentration. CHO-hOX40 cells were harvested, washed once with PBS, followed by counting and diluting to 2×10⁶/ml cell suspension; 10 μL the OX40 antibody MT01-L1 working solutions were added to 100 μL the cell suspension, respectively, followed by incubating at 4° C. for 30 min in the dark; after washing twice with PBS, a secondary antibody was added, followed by incubating at 4° C. for 30 min in the dark; after washing once with PBS, the resultants were suspended in 400 μL FACS buffer and tested on the machine. As shown in FIG. 3, the results show that MT01-L1 bound to human OX40 (hsOX40) with an $EC_{50}$ of 0.66 μg/mL.

Similarly, the binding of the antibody to CHO cells expressing mouse OX40 was tested, and it was found that MT01-L1 did not bind to mouse OX40 (msOX40; FIG. 3).

Similarly, the binding of the antibody to CHO cells expressing cynomolgus monkey OX40 was tested, and it was found that MT01-L1 bound to cynomolgus monkey OX40 (cyOX40) significantly (FIG. 3).

Example 4: Daudi Cell Proliferation Inhibition Assay

Figure 4:
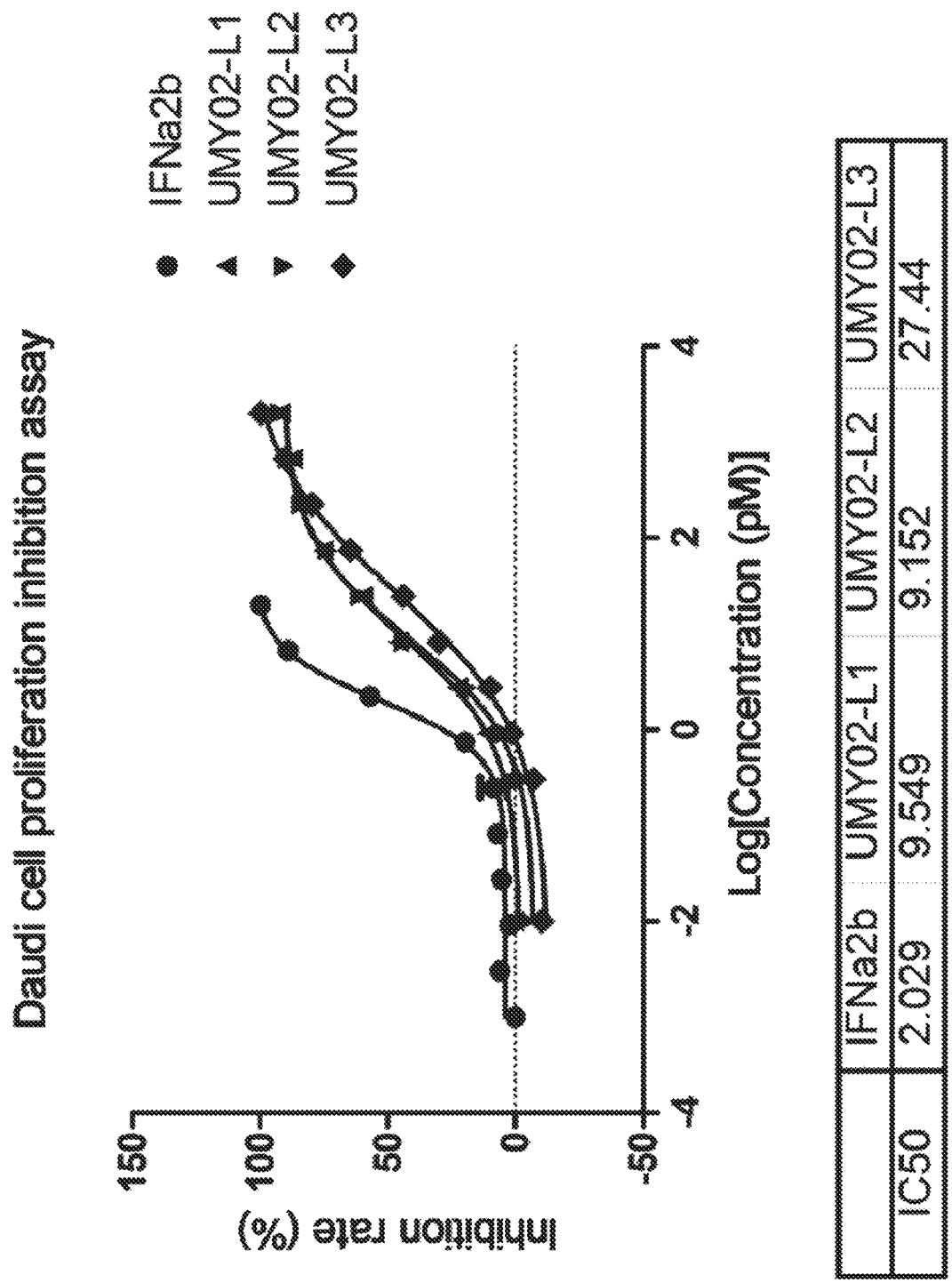
FIG. 4 shows the proliferation inhibitory effects of the fusion proteins according to the present invention on Daudi cells.

Interferon receptors are highly expressed on Daudi cells (ATCC), so interferon has a biological activity on the cells. Daudi cells were plated into a 96-well plate at 20,000 cells/90 μL/well; the samples to be tested were prepared into 10× working solutions by being diluted according to the concentration gradient, and added into the 96-well plate at 10 μL/well and placed in a 37° C. incubator, respectively; after 72 h, the OD450 values were determined by adding CCK8 and the proliferation inhibition rate was calculated for the cells in each well. This inhibition rate reflects the activity of interferon in the samples. The experimental results show that the proliferation inhibitory activities (ICso) of the fusion proteins UMY02-L1, UMY02-L2 and UMY02-L3 on Daudi cells were 9.549, 9.152 and 27.44 pM, respectively (FIG. 4).

Example 5: FcR-Mediated OX40 Signaling Pathway Activation Assay

A cellular assay system was constructed for detecting OX40 activators. Specifically, cell strains stably transfected by "Jurkat-OX40-NFκB-luciferase reporter gene (Luc)" were constructed, which could activate the expression of NFκB-luciferase reporter gene when the OX40 activating antibody was mixed with the stably transfected cell strains and HEK293 cells overexpressing FcR.

The solutions of the fusion proteins having a concentration gradient were prepared with PBS on ice, each of which being a working solution of 2× final concentration. Jurkat-NFκB-luc-OX40 cells and HEK293 cells overexpressing FcR were harvested, centrifuged, then resuspended in the culture medium, and plated into a 384-well plate. The fusion protein working solutions and a proper amount of cell suspension were added into the 384-well plate. After 5 h of incubation, One-Glo™ (Promega) detection reagent was added, and after uniform mixing the fluorescence signals were detected by Pherastar autofocus fluorescence microplate reader.

Figure 5:
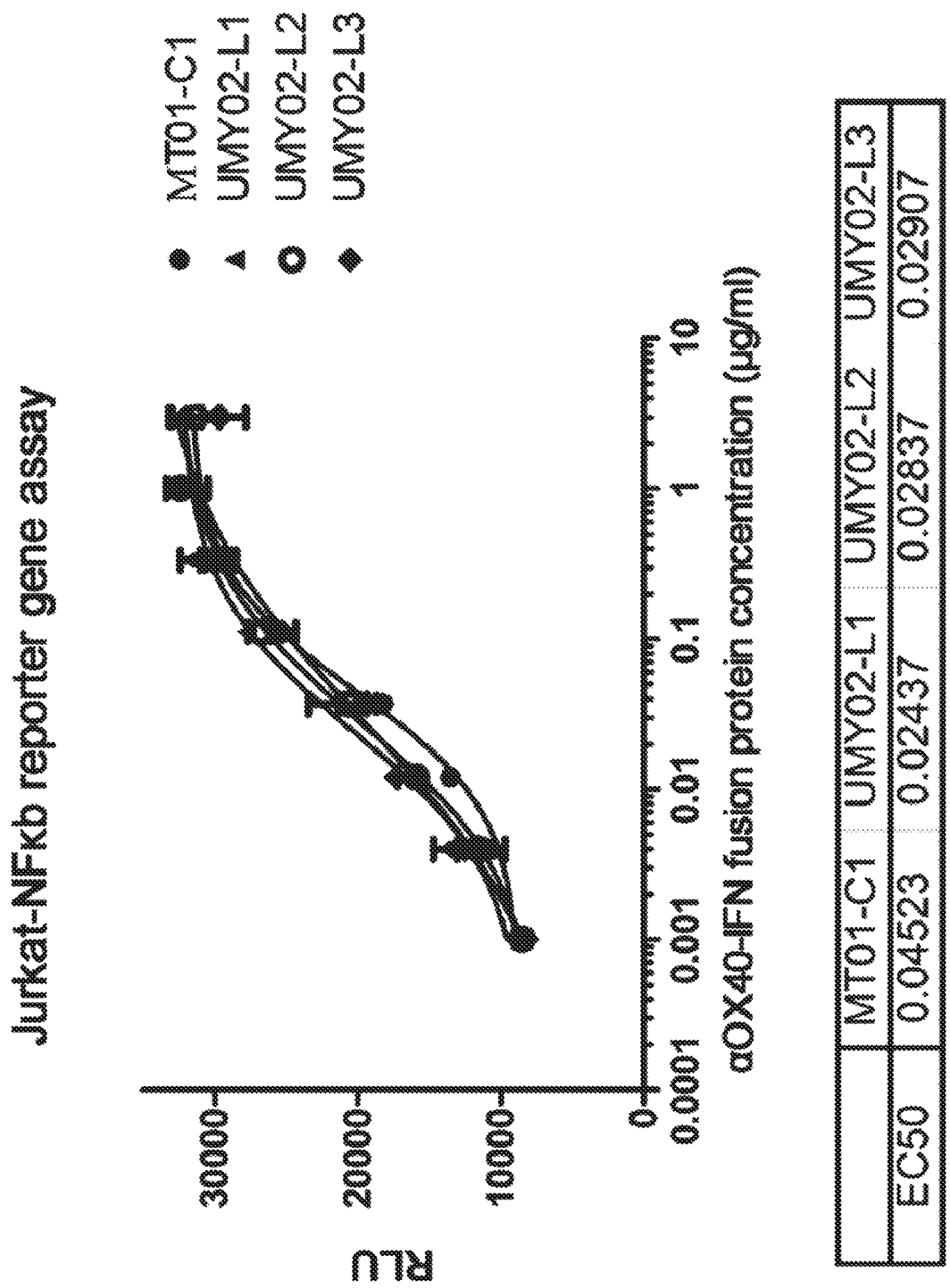
FIG. 5 shows that the OX-40 antibody/IFNα-2b fusion proteins according to the present disclosure activate the activity of NF-κB signaling pathway in Jurkat cells.

As shown in FIG. 5, the OX40 antibody MT01-C1 and the fusion proteins UMY02-L1, UMY02-L2 and UMY02-L3 were detected to activate NFκB-luciferase reporter with the $EC_{50}$ of 0.04523, 0.02437, 0.02837 and 0.02907 ng/mL, respectively, in the above experimental system. The results show that FcR-mediated OX40 activation activities of UMY02-L1, UMY02-L2 and UMY02-L3 were stronger than that of MT01-C1.

Example 6: Interferon Receptor-Mediated OX40 Signaling Pathway Activation Assay

The cell strains transfected stably by "Jurkat-OX40-NFκB-luciferase reporter" were plated into a 384-well plate at 10,000/well. The solutions of the fusion protein having a concentration gradient and a control group solution were prepared with PBS on ice, each of which being a working solution of 2× final concentration. The fusion protein or the interferon working solution and a proper amount of cell suspension were added into the 384-well plate. After 5 h incubation, One-Glo™ (Promega) detection reagent was added, and after uniform mixing the fluorescence signals were detected by Pherastar autofocus fluorescence microplate Reader.

Figure 6A:
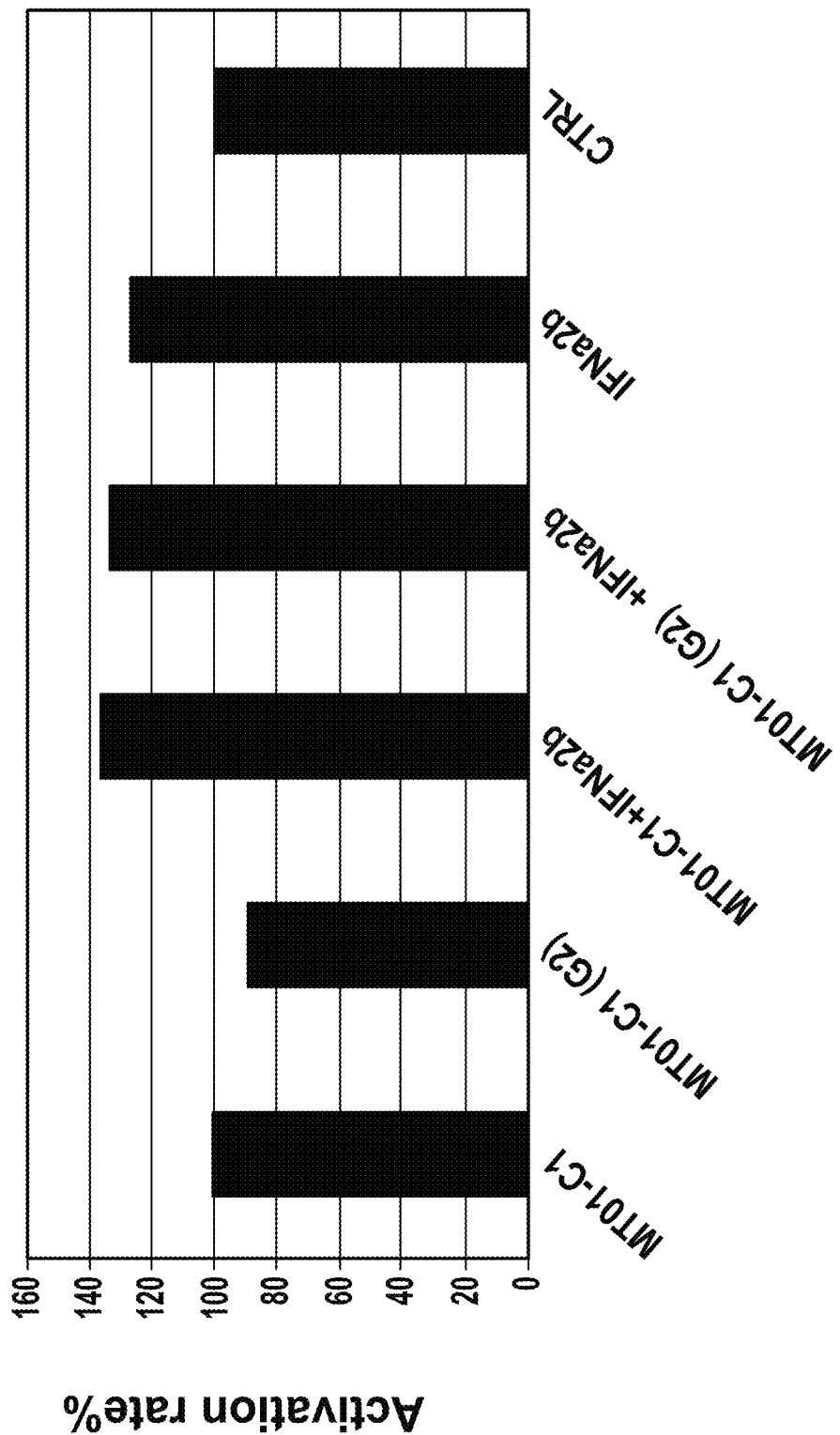
FIGS. 6A and 6B show that the OX-40 antibody/IFNα-2b fusion proteins according to the present disclosure can promote the activity of the MT01-C1 antibody for activating OX40 signaling pathway. A OX40 monoclonal antibody (mAb) (MT01-C1 or MT01-C1 (G2)) alone or the interferon molecule IFNα-2b has no or only a weak activation effect on the OX40 signaling pathway in Jurkat cells in this experimental system (FIG. 6A). However, the fusion proteins (UMY02-L1, UMY02-L2 and UMY02-L3) have a significant activation activity on the signaling pathway of OX40 under the same conditions (FIG. 6B)
Figure 6B:
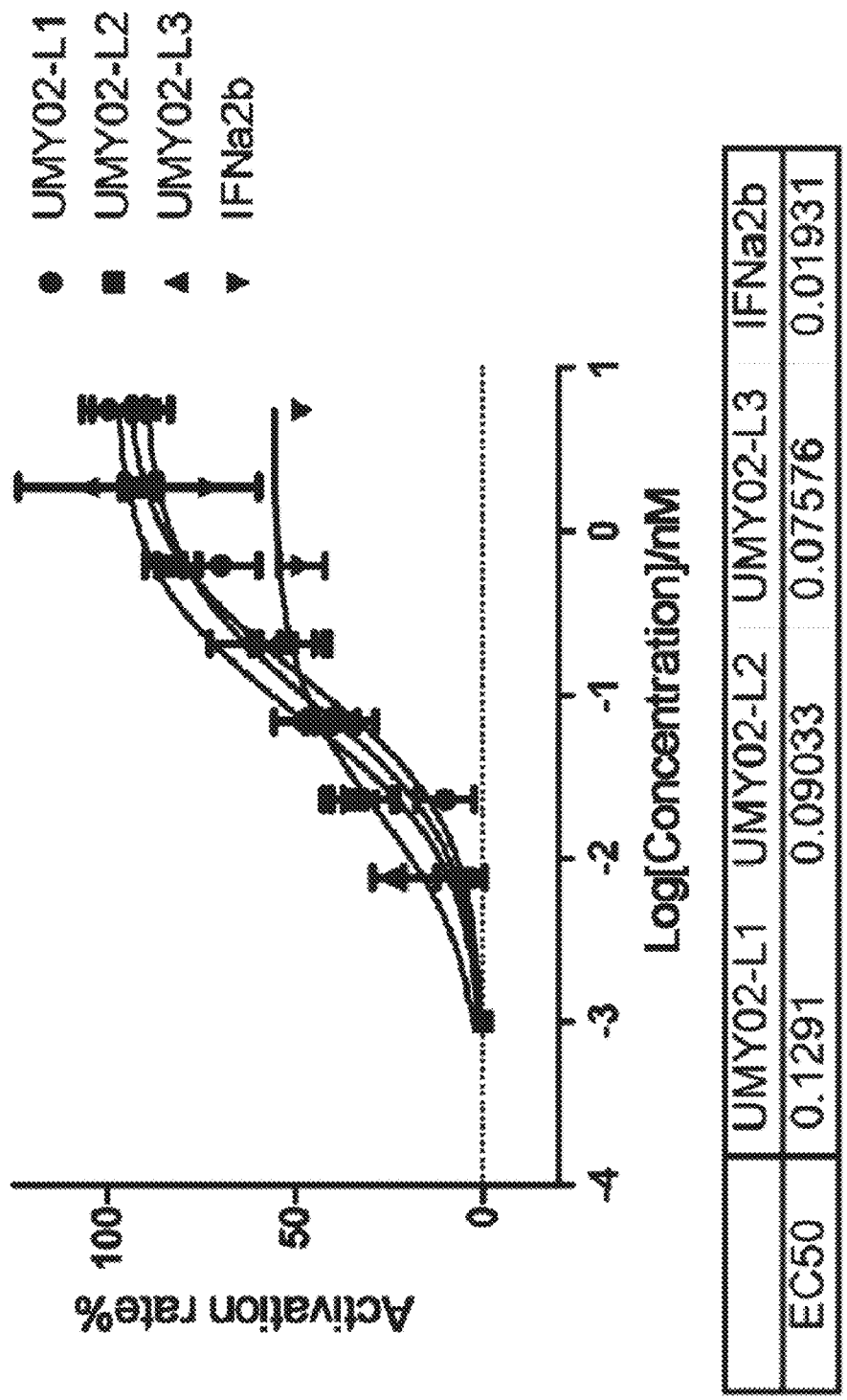

As shown in FIG. 6A, the final concentrations of all antibodies or the interferon in the assay were 10 nM. The OX40 antibody MT01-C1 or MT01-C1 (G2) did not show the activating effect on the OX40 signaling pathway in Jurkat cells, and addition of interferon IFNα-2b alone or simultaneous addition of the OX40 antibody MT01-C1 and IFNα-2b had an activation effect of less than 40% compared to the control group. However, when the fusion protein UMY02-L1, UMY02-L2 or UMY02-L3 was added, the OX40 signaling pathway in Jurkat cells was significantly activated, and the activation degree was significantly greater than that of the interferon group alone (FIG. 6B).

Example 7: Pharmacokinetics Assay in C57BL/6 Mice

Eighteen female C57BL/6 mice aged 6-8 weeks were divided into 3 groups, 6 for each group, and were injected intravenously with UMY02-L1, UMY02-L3, and MT01-C1 respectively. The dose administered was 5 mg/kg. For UMY02-L1 or UMY02-L3, the peripheral venous blood was collected from the animals before the administration and at 1, 2, 6, 24, 48, 72, 96, 174, 220 and 288 h after the administration; for MT01-C1, the peripheral venous blood was collected from the animals before the administration and at 1, 2, 6, 24, 48, 72, 96, 192 and 312 h after the administration; the serums were collected by centrifugation. The serums were collected from 3 animals at each time point, and the blood samples were collected alternately from 6 animals in each group at different time points.

A 96-well high affinity plate was coated with 1 μg/mL human OX40 protein solution at 100 μL/well and shaken overnight at 4° C. The next day, the plate was first washed 3 times with 300 μL PBST (Tween 20: 0.5% c), then blocked with 5% BSA/PBS at 100 μL/well for 1 h, and shaken at room temperature, followed by washing 4 times with 300 μL PBST. 100-fold diluted solutions of serum samples to be tested and control serum solutions with different concentrations were prepared by PBS, and then added to the 96-well plate at 100 μL/well; the plate was shaken for 1.5 h at room temperature, followed by washing 4 times with 300 μL PBST. For MT01-C1, a solution of secondary antibody donkey-anti-human IgG HRP (Jackson ImmunoResearch, Art. No. 709-035-149) was prepared and added into the 96-well plate at 100 μL/well, and the plate was shaken for 1 h at room temperature, followed by washing 4 times with 300 μL PBST. TMB was added at 100 μL/well to develop color for 20 min. 0.6N $H_2SO_4$ was added at 100 μL/well to stop the color development, and the OD values were determined at 450 nm. For UMY02-L1 and UMY02-L3, 0.5 μg/mL rabbit-anti-human IFN (Abcam, Art. No. ab222552) solution was prepared and added to the 96-well plate at 100 μL/well, and the plate was shaken for 1.5 h at room temperature, followed by washing 4 times with 300 μL PBST. A secondary antibody goat-anti-rabbit IgG HRP (GenScript Biotech Corp., Art. No. A00098) solution was prepared and added to the 96-well plate at 100 μL/well, and the plate was shaken for 1 h at room temperature, followed by washing 4 times with 300 μL PBST. 100 μL/well TMB was added to develop color for 20 min. 0.6N $H_2SO_4$ was added at 100 μL/well to stop the color development, and the OD values were determined at 450 nm. Logistic four-parameter fitting was conducted on the detection values of control solutions with different concentrations relative to the concentrations of control solutions to obtain a standard curve and a regression equation. The detected values of the samples to be tested were substituted into the equation for calculation to obtain the serum drug concentrations at different time points.

Figure 7A:
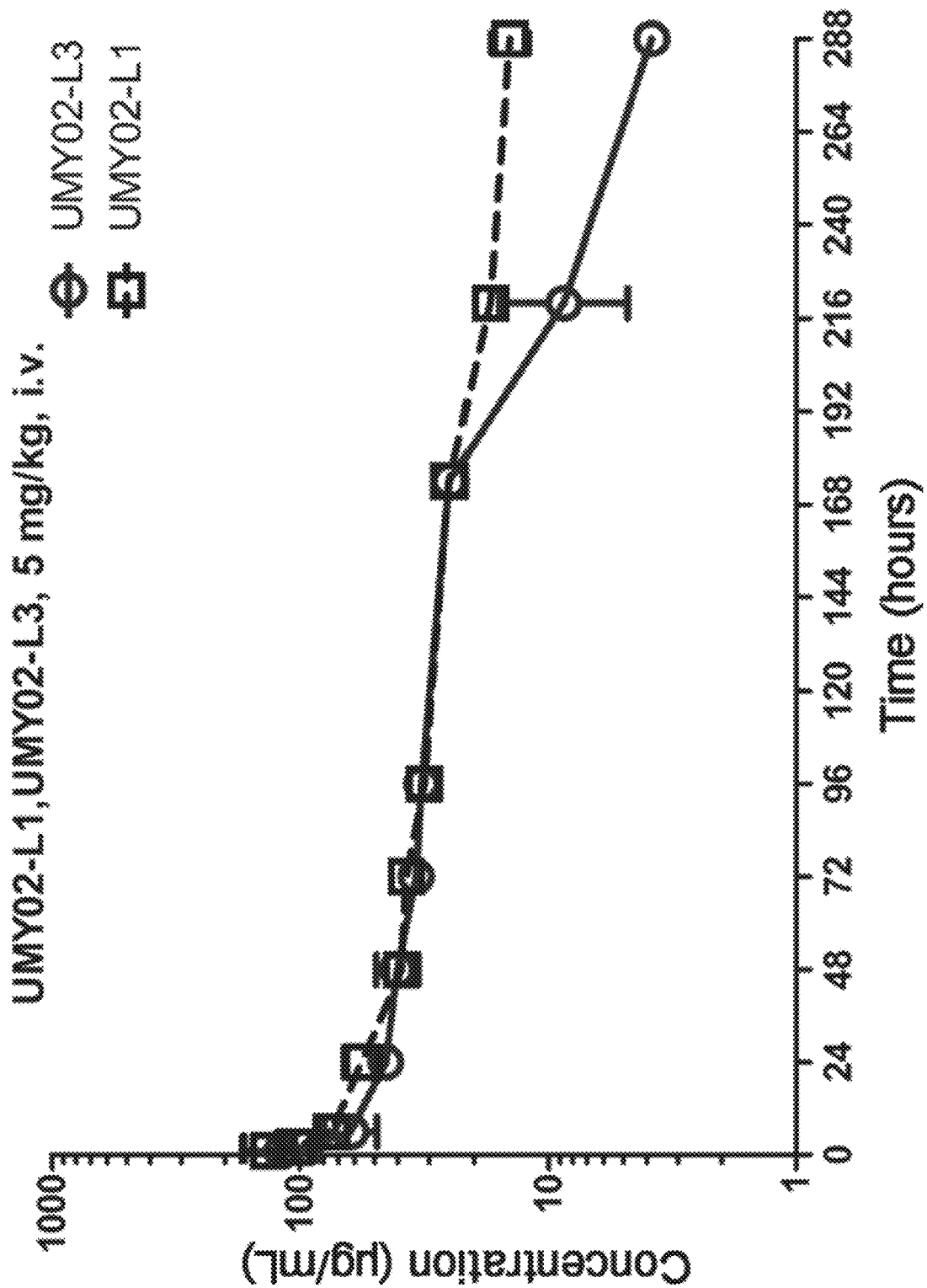
FIGS. 7A and 7B show the pharmacokinetic profiles of UMY02-L1 and UMY02-L3 on mice (FIG. 7A). For comparison.
Figure 7B:
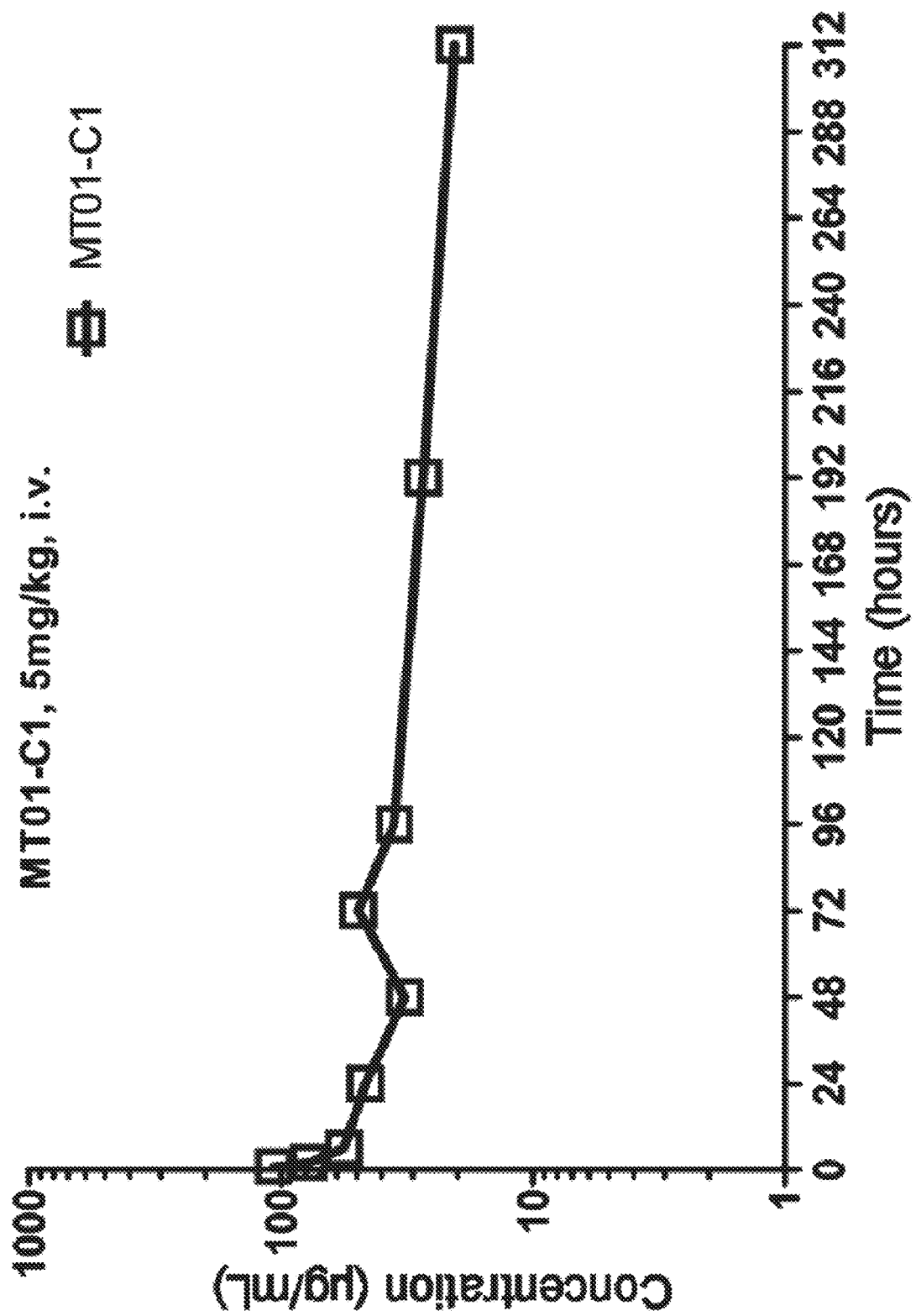
Figure 8:
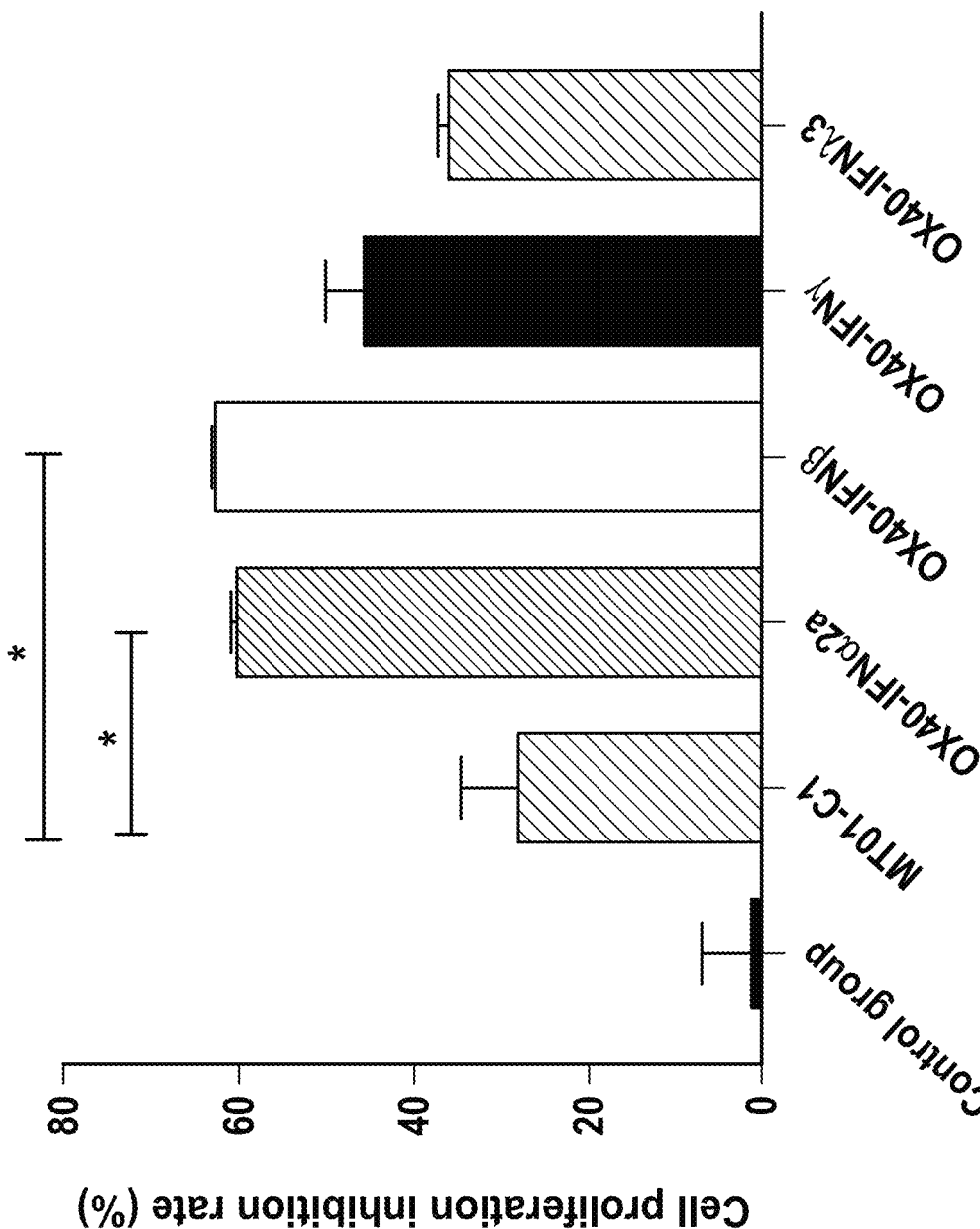
FIG. 8 shows the killing effects of the OX40 antibody/IFNα-2a fusion protein, OX40/IFNβ fusion protein, OX40/IFNγ fusion protein, and OX40/IFNγ3 fusion protein according to the present disclosure on tumor cells.
Figure 9:
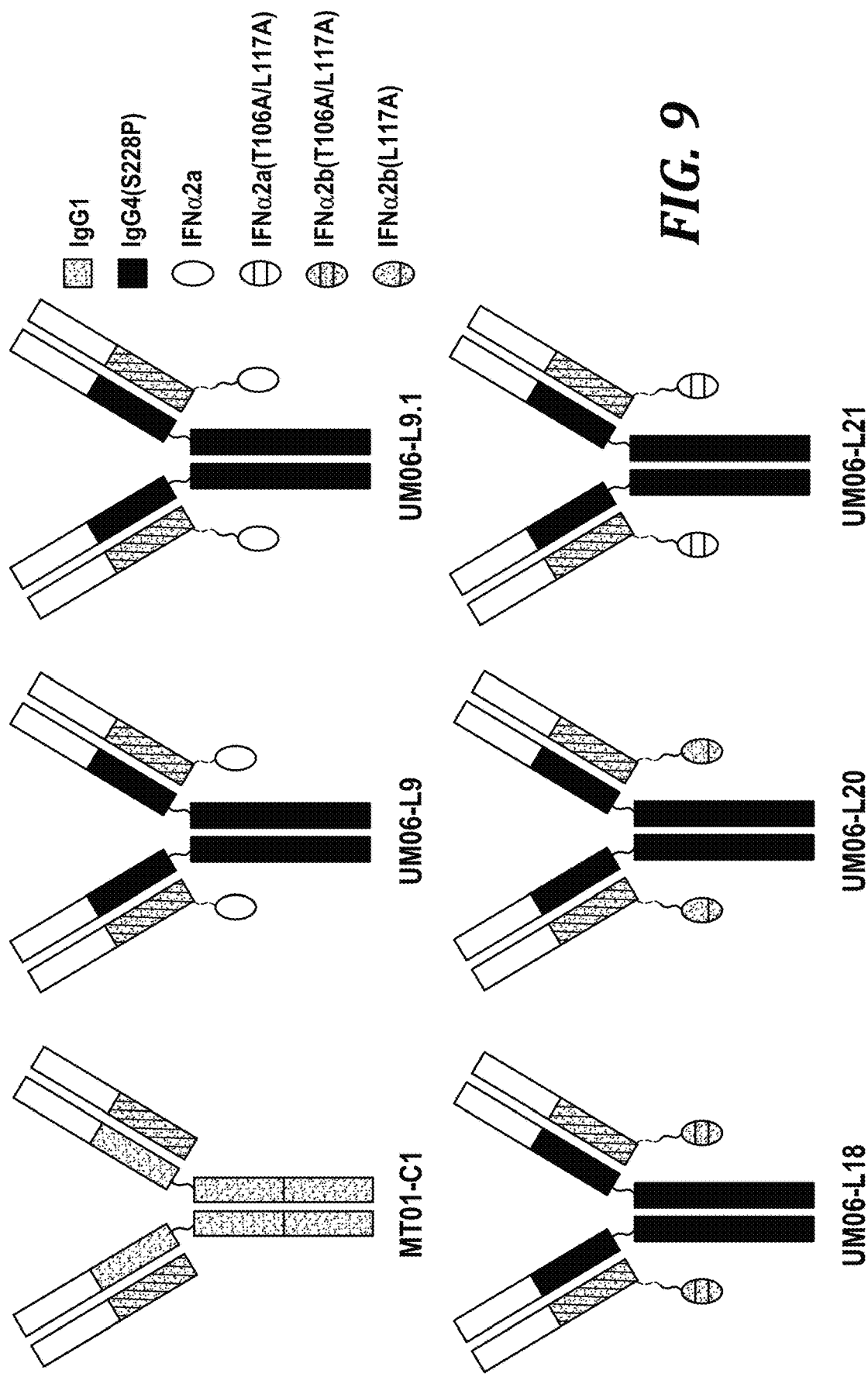
FIG. 9 shows the schematic diagram of structures of the OX40 antibody/IFNα-2a fusion proteins according to the present disclosure.

As shown in FIG. 7A and FIG. 7B, the mice in the experiment were injected with 5 mg/kg UMY02-L3 or UMY02-L1 intravenously. Seven (7) days after the administration, the serum drug concentration of UMY02-L3 was still above 10 μg/mL, and 12 days after the administration, the serum drug concentration of UMY02-L1 was still above 10 μg/mL, indicating the fusion proteins UMY02-L3 and UMY02-L1 have the pharmacokinetic characteristics similar to the antibody drug MT01-C1 in mice, and a much longer half-life than 2-3 h of IFNα-2b (see product manual for Intron A, Merck).

Example 8: Effect of Antibody Subtype and Peptide Linker Length on the Activity of Antibody Fusion Protein To investigate the effects of length of a peptide linker linking an OX40 activating antibody and interferon IFNα-2b, and antibody subtype on OX40 signaling pathway activating activity of the fusion proteins, the antibody fusion proteins with peptide linkers having different lengths and different antibody subtypes were constructed based on UMY02-L3 (see Table 2).

The heavy chains of the fusion proteins UMY02-L4, UMY02-L5 and UMY02-L6 are as shown in SEQ ID NO:14, and the light chain and the human interferon are as shown in SEQ ID NO:13, with the only difference in the number of peptide linker, as shown in Table 2 below.

The heavy chains of the fusion proteins UMY02-L7 and UMY02-L8 are as shown in SEQ ID NO:15, and the light chain and the human interferon are as shown in SEQ ID NO:13, with the only difference in the number of peptide linker, as shown in Table 2 below.

The effects of these antibody fusion proteins on Daudi cell proliferation were tested according to the method in Example 4, and as a result it was found that different peptide linker lengths have a significant effect on the interferon activity of the antibody fusion proteins, namely, the shorter the peptide linker length is, the lower the interferon activity is (see Table 2).

The activities of these fusion proteins for activating the OX40 signaling pathway were tested using the method in Example 5. As shown in Table 2, the OX40 antibody MT01-C1 and the fusion proteins of various antibodies were detected to be effective in activating the OX40 signaling pathway in Jurkat-OX40 cells.

TABLE 2

Effects of antibody subtype and linker length on interferon activity

| Name | Antibody subtype | Peptide linker | Daudi cell proliferation assay $IC_{50}$ (pM) | Daudi cell proliferation assay Relative activity | Activation activity of OX40 signaling pathway $EC_{50}$ (nM) | Activation activity of OX40 signaling pathway Relative activity |
|---|---|---|---|---|---|---|
| MT01-C1 | IgG1 | / | / | / | 0.178 | 1.00 |
| IFNα-2b | / | / | 0.7982 | 1.00 | | |
| UMY02-L3 | IgG1 | (GGGGS)$_3$ | 21.45 | 3.72E−02 | 0.179 | 0.99 |
| UMY02-L4 | IgG1 | Without a peptide linker | 855.3 | 9.33E−04 | 0.280 | 0.64 |
| UMY02-L5 | IgG1 | GGGGS | 86.75 | 9.20E−03 | 0.302 | 0.59 |
| UMY02-L6 | IgG1 | (GGGGS)$_2$ | 53.20 | 1.50E−02 | 0.309 | 0.58 |
| UMY02-L7 | IgG4 | GGGGS | 1263.00 | 6.32E−04 | 0.497 | 0.36 |
| UMY02-L8 | IgG4 | (GGGGS)$_2$ | 259.1 | 3.08E−03 | 0.358 | 0.50 |

Example 9: Fusion of OX40 Antibody to Different IFNα-2b Mutant Proteins

The OX40 activating antibody may also be fused to an interferon mutant. The specific activities of the mutant interferons are lower than those of wild-type interferons, so that the mutant interferons may act synergistically with the OX40 antibody at the same drug concentration, and meanwhile the toxic and side effects caused by excessive interferon activity are avoided.

In this example, a series of OX40 antibody-mutant interferon fusion proteins were constructed and expressed using the HEK 293 expression system (Table 3). In these antibody fusion proteins, the antibody subtype of OX40 was IgG4, while the IFNα-2b portion carried a T106A mutation to remove its glycosylation site.

The heavy chains of the fusion proteins UMY02-L13, UMY02-L14, UMY02-L15, UMY02-L16, UMY02-L17 and UMY02-L18 are as shown in SEQ ID NO:15, and the light chain and the human interferon are as shown in SEQ ID NO:13, only with the following differences:
1. The peptide linkers of UMY02-L13, UMY02-L14, UMY02-L15, UMY02-L16 and UMY02-L18 are (GGGGS)$_2$, and the peptide linker of UMY02-L17 is (GGGGS)$_3$;
2. The interferons of the fusion proteins UMY02-L13, UMY02-L14, UMY02-L15, UMY02-L16, UMY02-L17 and UMY02-L18 have the mutation as shown in Table 3 relative to SEQ ID NO:9.

Figure 10:
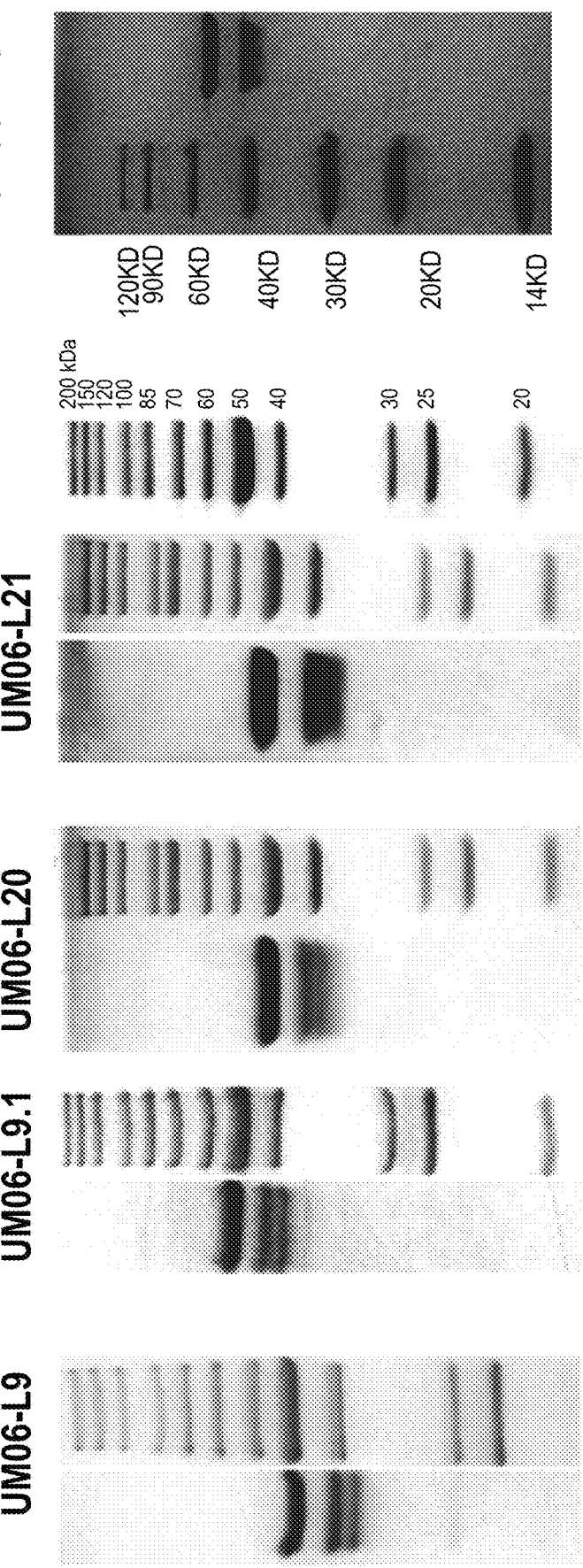
FIG. 10 shows the SDS-PAGE and HPLC profiles of the OX40 antibody/IFNα-2a fusion proteins according to the present disclosure.
Figure 10:
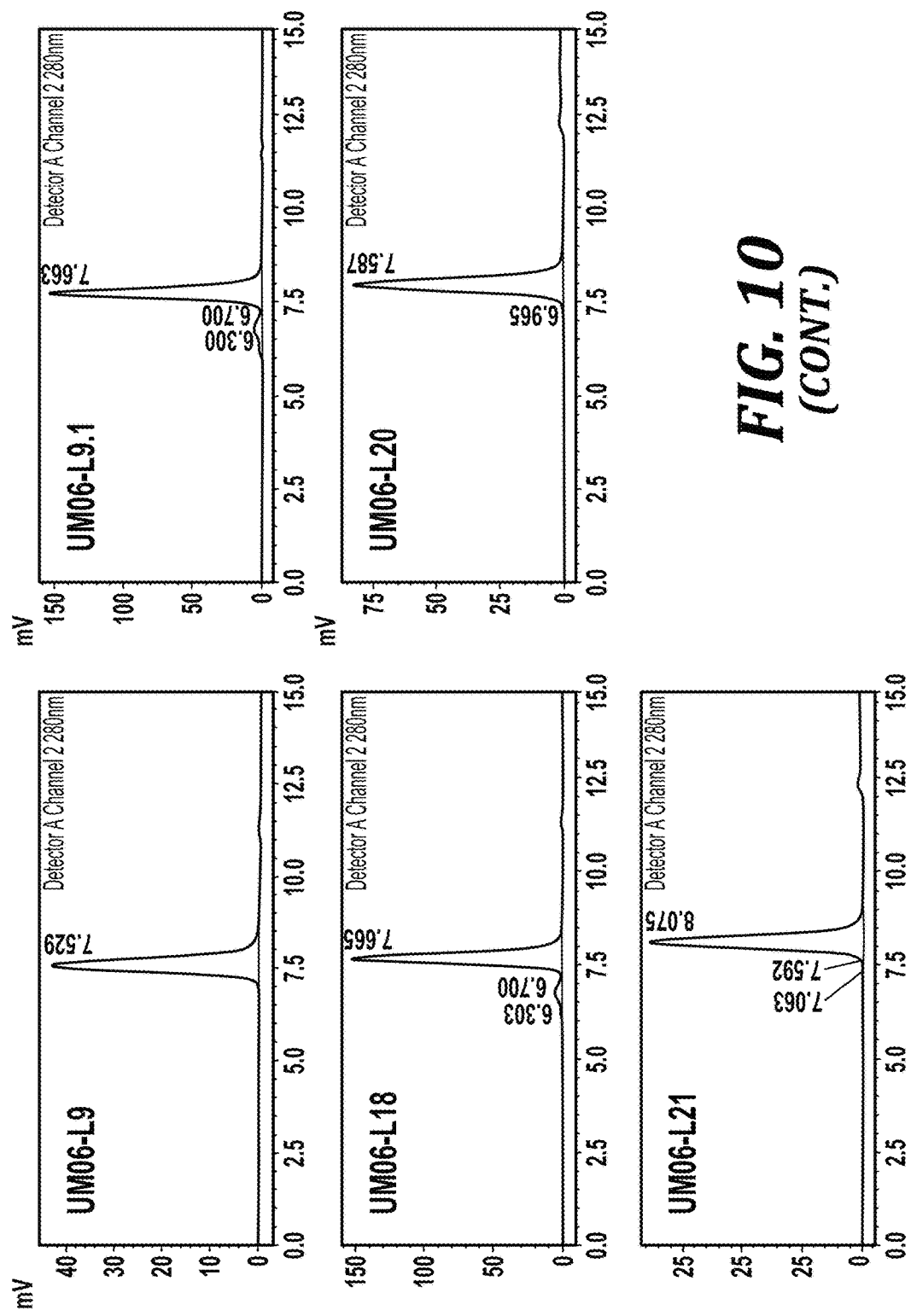

The effects of these antibody fusion proteins on Daudi cell proliferation were tested according to the method in Example 4, and as a result it was found that the interferon activities of the mutant antibody fusion proteins were significantly lower than that of the wild-type IFNα-2b (Table 3). Meanwhile, the activation effects of OX40 signaling pathway in Jurkat cells by these antibody fusion proteins were tested according to the method in Example 5, and the results show that the OX40 activation activities of these mutant antibody fusion proteins were substantially unchanged (Table 3). This result indicates that a suitable OX40 antibody-IFN fusion protein could be obtained by introducing a specific mutation into the interferon sequence, ensuring that the OX40 activating activity and the interferon activity are matched at an equal molar concentration, exert their functions synergistically in human body, and avoid a poor therapeutic effect or severe toxic and side effects caused by too high or low activity of one of them.

TABLE 3

Activities of mutated antibody fusion proteins

| | | Daudi cell proliferation assay | | Activation activity of OX40 signaling pathway | |
|---|---|---|---|---|---|
| | Interferon mutation[1] | $IC_{50}$ (pM) | Relative activity[2] | $EC_{50}$ (nM) | Relative activity[3] |
| MT01-C1 | / | / | / | 0.3251 | 1.00 |
| IFNα2b | wt | 0.683 | 1.00 | / | / |
| UMY02-L13 | T106A/A145D | 28589 | 2.39E−05 | 0.4972 | 0.65 |
| UMY02-L14 | T106A/R149A | 18110 | 3.77E−05 | 0.4634 | 0.70 |
| UMY02-L15 | T106A/R120A | 1892 | 3.61E−04 | / | / |
| UMY02-L16 | T106A/A145G | 2069 | 3.30E−04 | 0.5661 | 0.57 |
| UMY02-L17 | T106A/R149A | 16094 | 4.24E−05 | 0.4608 | 0.71 |
| UMY02-L18 | T106A/L117A | 3318 | 2.06E−04 | 0.5410 | 0.60 |

[1]The position number of mutated amino acid is indicated referring to the amino acid sequence of wild-type human interferon IFNα-2b, SEQ ID NO: 9.
[2]The activity of IFNα-2b is defined as 1.
[3]The activity of the OX40 mAb MT01-C1 is defined as 1.

Example 10 Killing Effects of the Fusion Proteins on Tumors Cell

Further, the heavy chain of the OX40 antibody was fused to different types of interferons to produce different fusion proteins, wherein the heavy chains of OX40-IFNα-2a, OX40-IFNβ, OX40-IFNγ, and OX40-IFNλ3 are as shown in SEQ ID NO:15; the light chain, the peptide linker and the interferon of the OX40-IFNα-2a are as shown in SEQ ID NO:16; the light chain, the peptide linker and the interferon of the OX40 IFNβ are as shown in SEQ ID NO:17; the light chain, the peptide linker and the interferon of the OX40-IFNγ are as shown in SEQ ID NO:18; and the light chain, the peptide linker and the interferon of OX40-IFNλ3 are as shown in SEQ ID NO:19.

The killing effects of these antibody fusion proteins on tumor cell were tested. Specifically, human-derived PBMCs and ovarian cancer SKOV3 cells were mixed and co-cultured at a ratio of 20:1, and stimulated with PBS (control), or the OX40 mAb MT01-C1 and the different antibody fusion proteins (OX40-IFNα-2a, OX40-IFNβ, OX40-IFNγ, OX40-IFNλ3) at a concentration of 0.1 nM, respectively; after 48 h of cultivation at 37° C., 5% $CO_2$, the cytotoxicities of PBMCs on SKOV3 cells were detected by CCK8 kit. The experimental results are shown in FIG. 8, showing that PBMCs had no an inhibitory effect on SKOV3 cell proliferation without stimulation; the inhibition rate of PBMCs on SKOV3 was about 28% under the stimulation by the OX40 mAb; however, under the stimulation of fusion proteins, the cytotoxicities of PBMC were stronger than that under the stimulation of the OX40 mAb, wherein the inhibition rates under the stimulation of the OX40 mAb MT01-C1-IFNα-2a and the OX40 mAb MT01-C1-IFNβ were significantly enhanced, i.e., 60% and 63%, respectively.

Example 11: Preparation of the Fusion Proteins Having an Anti-OX40 Antibody and Human Interferon α-2

This example illustrates the design and expression of several anti-OX40 antibody-human interferon fusion proteins. "MT01-C1" refers to a monoclonal antibody having the same VH (SEQ ID NO:7) and VL (SEQ ID NO:8) sequences as UM06-L9, UM06-L9.1, UM06-L18, UM06-L20 and UM06-L21, the heavy and light chain constant regions of which are human IgG4 (S228P) and κ chain, respectively.

The interferon IFNα-2 sequence is taken from the human interferon IFNα-2a (P01563), the amino acid sequence of which is as shown in SEQ ID NO:20; or the human interferon IFNα-2b, the amino acid sequence of which is as shown in SEQ ID NO:9.

The structural design of exemplary fusion proteins is as shown in FIG. 9, wherein "UM06-L9" refers to a fusion protein consisting of an OX40 antibody comprising the heavy chain as shown in SEQ ID NO:21 and the light chain as shown in SEQ ID NO:22, a peptide linker, and the human interferon IFNα-2a as shown in SEQ ID NO:20, wherein the human interferon IFNα-2a is linked to the carboxyl-terminus of the light chain of the OX40 antibody via a peptide linker GGGGS;

"UM06-L9.1" refers to a fusion protein consisting of an OX40 antibody comprising the heavy chain as shown in SEQ ID NO:21 and the light chain as shown in SEQ ID NO:23, a peptide linker, and the human interferon IFNα-2a as shown in SEQ ID NO:20, wherein the human interferon IFNα-2a is linked to the carboxyl-terminus of the light chain of the OX40 antibody via a peptide linker $(GGGGS)_2$;

"UM06-L21" refers to a fusion protein consisting of an OX40 antibody comprising the heavy chain as shown in SEQ ID NO:21 and the light chain as shown in SEQ ID NO:25, a peptide linker, and the human interferon IFNα-2a mutant (T106A/L117A) as shown in SEQ ID NO:24, wherein the human interferon IFNα-2a mutant is linked to the carboxyl-terminus of the light chain of the OX40 antibody via a peptide linker $(GGGGS)_2$;

"UM06-L18" refers to a fusion protein consisting of an OX40 antibody comprising the heavy chain as shown in SEQ ID NO:21 and the light chain as shown in SEQ ID NO:27, a peptide linker, and the human interferon IFNα-2b mutant (T106A/L117A) as shown in SEQ ID NO:26, wherein the human interferon IFNα-2b mutant is linked to the carboxyl-terminus of the light chain of the OX40 antibody via a peptide linker $(GGGGS)_2$;

"UM06-L20" refers to a fusion protein consisting of an OX40 antibody comprising the heavy chain as shown in SEQ ID NO:21 and the light chain as shown in SEQ ID NO:29, a peptide linker, and the human interferon IFNα-2b mutant (L117A) as shown in SEQ ID NO:28, wherein the human interferon IFNα-2b mutant is linked to the carboxyl-terminus of the light chain of the OX40 antibody via a peptide linker $(GGGGS)_2$.

The cDNA sequences encoding the heavy and light chains of the antibodies of the fusion proteins were cloned into the mammalian cell expression vector pcDNA 3.4, respectively. The heavy chain expression plasmids and light chain expression plasmids were transfected into HEK293 cells with Lipofectamine 2000™ transfection reagent (Invitrogen) at a molar ratio of 2:1 and cultured for 7 days at 37° C. and 5% carbon dioxide. The supernatants were collected, and the antibodies in the supernatants were purified by Protein A affinity chromatography. The purified antibodies were dialyzed against PBS solution and concentrated by lyophilization and stored at −20° C. The SDS-PAGE and HPLC profiles of the purified proteins are as shown in FIG. 10.

Example 12: ELISA Binding Assay

A 96-well high affinity plate was coated with 1 μg/mL human OX40 protein solution at 100 μL/well, and shaken overnight at 4° C. The next day, the plate was first washed 3 times with 300 μL PBST (Tween 20: 0.5% c), then blocked with 5% BSA/PBS at 100 μL/well for 2 h, and shaken at room temperature, followed by washing 3 times with 300 μL PBST. Gradient dilutions of the fusion protein samples were prepared in PBS, and then added to the 96-well plate at 100 μL/well; the plate was shaken for 1 h at room temperature, followed by washing 3 times with 300 μL PBST. A mouse-anti-human IgG HRP (GenScript Biotech Corp., Art. No. A01854) solution was prepared and added into the 96-well plate at 100 μL/well, and the plate was shaken for 1 h at room temperature, followed by washing 4 times with 300 μL PBST. TMB was added at 100 μL/well to develop color for 20 min. 0.6N $H_2SO_4$ was added at 100 μL/well to stop the color development, and the OD (optical density) values were determined at 450 nm.

Figure 11:
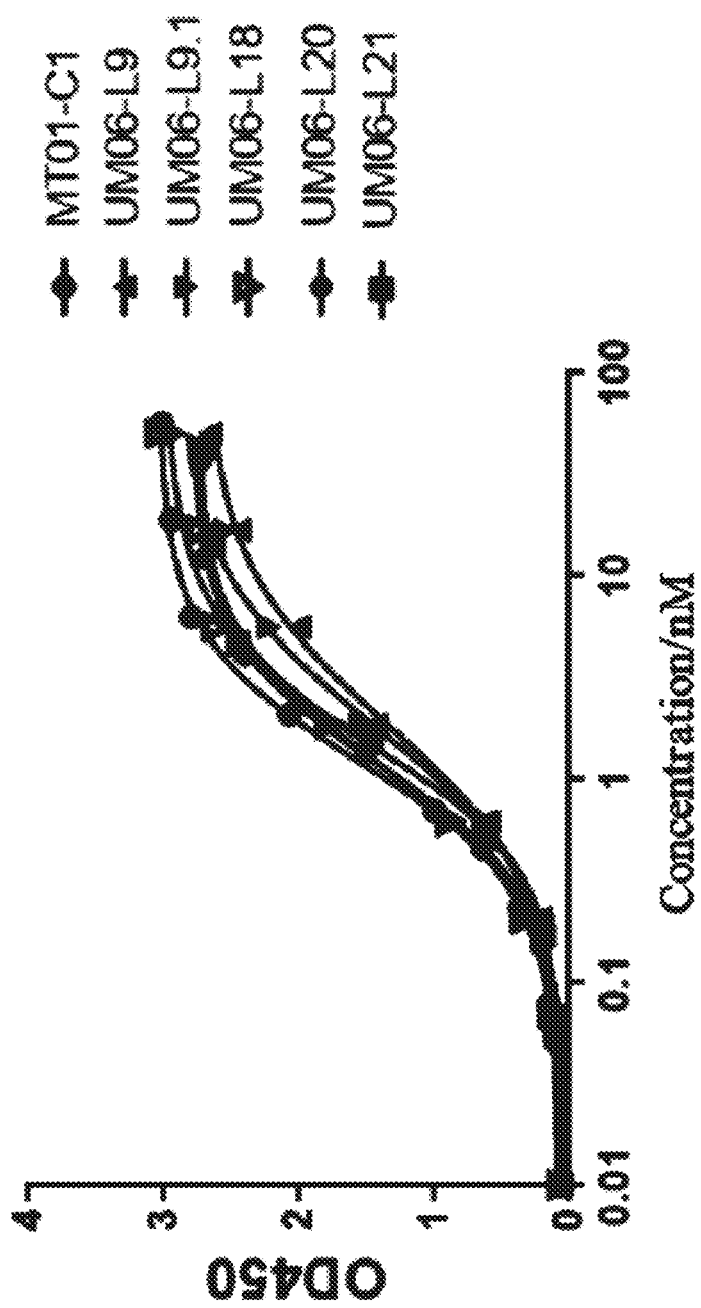
FIG. 11 shows the results of ELISA binding assay of the OX40 antibody/IFNα-2a fusion proteins according to the present disclosure to human OX40 protein.

After testing, the results are shown in FIG. 11, and the $EC_{50}$ of the fusion proteins UM06-L9, UM06-L9.1, UM06-L18, UM06-L20, and UM06-21 for ELISA binding were 1.880, 1.836, 1.347, 1.198, and 1.382 nM, respectively, all of which were substantially equivalent to $EC_{50}$ (1.214 nM) of the OX40 antibody MT01-C1 (FIG. 11).

Example 13: Daudi Cell Proliferation Inhibition Assay

Figure 12:
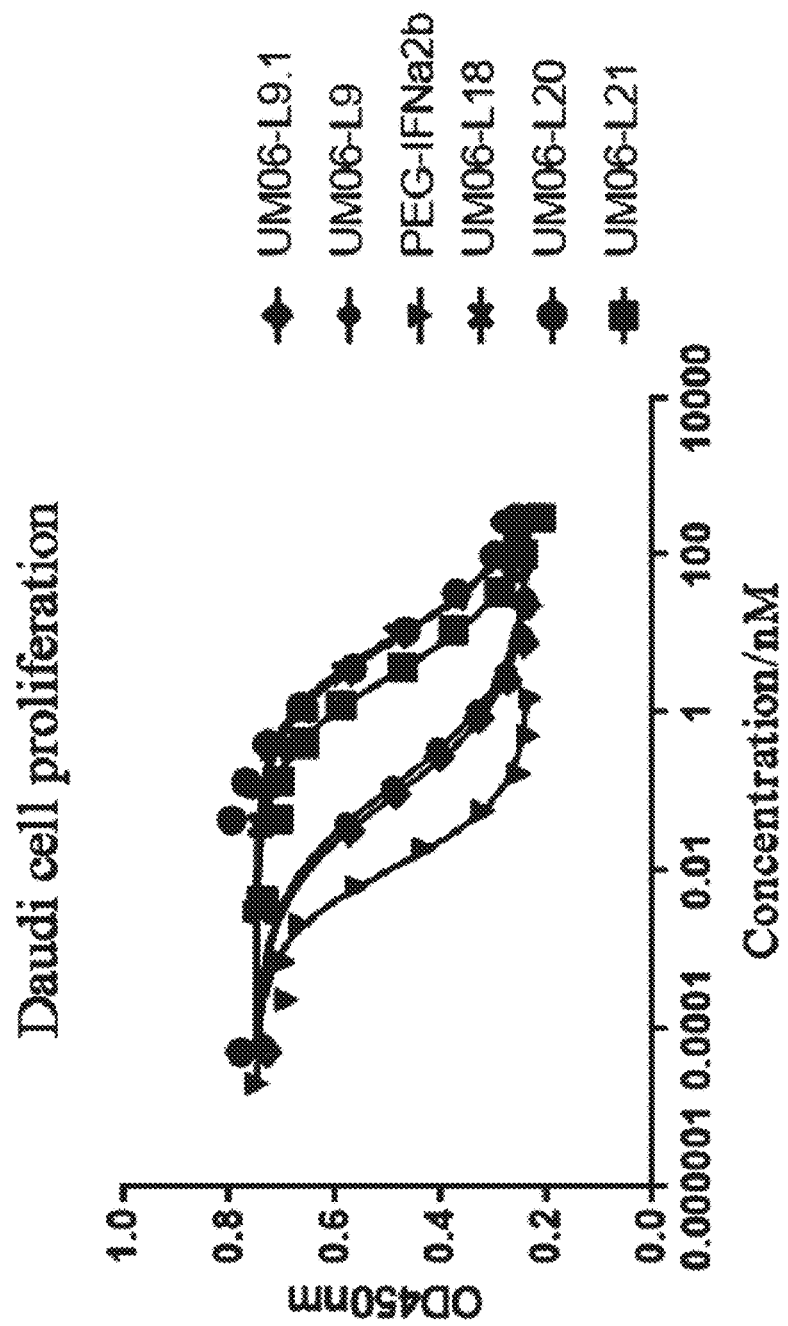
FIG. 12 shows the proliferation inhibitory effects of the OX40 antibody/IFNα-2a fusion proteins according to the present disclosure on Daudi cells.

Due to the strong physiological activity of cytokine IFNα-2, it is contemplated necessarily that the activity of interferon in the fusion protein is appropriately reduced when IFNα-2 is fused to the OX40 antibody. According to the clinical doses of OX40 therapeutic antibody and long-acting interferon (pegylated interferon), the activity of interferon in the fusion protein should be hundreds of times lower than that of long-acting interferon. The activity of human interferon may be characterized using Daudi cell proliferation assay. Interferon receptors are highly expressed on Daudi cells (ATCC), so interferon has a biological activity on the cells. Daudi cells were plated into a 96-well plate at 20,000 cells/90 μL/well; the samples to be tested were prepared into 10× working solutions by being diluted according to the concentration gradient, and added into the 96-well plate at 10 μL/well, and placed in a 37° C. incubator, respectively; after 72 h, the OD450 values were determined by adding CCK8 and the proliferation inhibition rate was calculated for the cells in each well. This inhibition rate reflects the activity of interferon in the samples. The results show that pegylated interferon α2 (Pegberon, Xiamen Amoytop Biotech, Batch No. 201811JS19), and the fusion proteins UM06-L9, UM06-L9.1, UM06-L18, UM06-L20 and UM06-L21 had a proliferation inhibitory activity on Daudi cells with the $IC_{50}$ of 10.64, 85.87, 92.06, 7886, 8556 and 2964 pM, respectively (FIG. 12).

Example 14: OX40 Signaling Pathway Activation Assay

A cellular assay system for detecting OX40 activators was constructed. Specifically, cell strains transfected stably by "HEK293-OX40-NFκB-luciferase reporter gene (Luc)" were constructed, which could activate the expression of NFκB-luciferase reporter gene when the OX40 activating antibody was mixed with the stably transfected cell strains and Raji cells expressing FcR.

The solutions of the fusion proteins having a concentration gradient were prepared with PBS on ice, each of which being a working solution of 2× final concentration. "HEK293-OX40-NFκB-Luc" cells and Raji cells were harvested, centrifuged, then re-suspended in the culture medium, and plated into a 384-well plate. The fusion protein working solutions and a proper amount of cell suspension were added into the 384-well plate. After 5 h of incubation, One-Glo™ (Promega) detection reagent was added, and after uniform mixing the fluorescence signals were detected by TECAN SPARK® 20M.

Figure 13A:
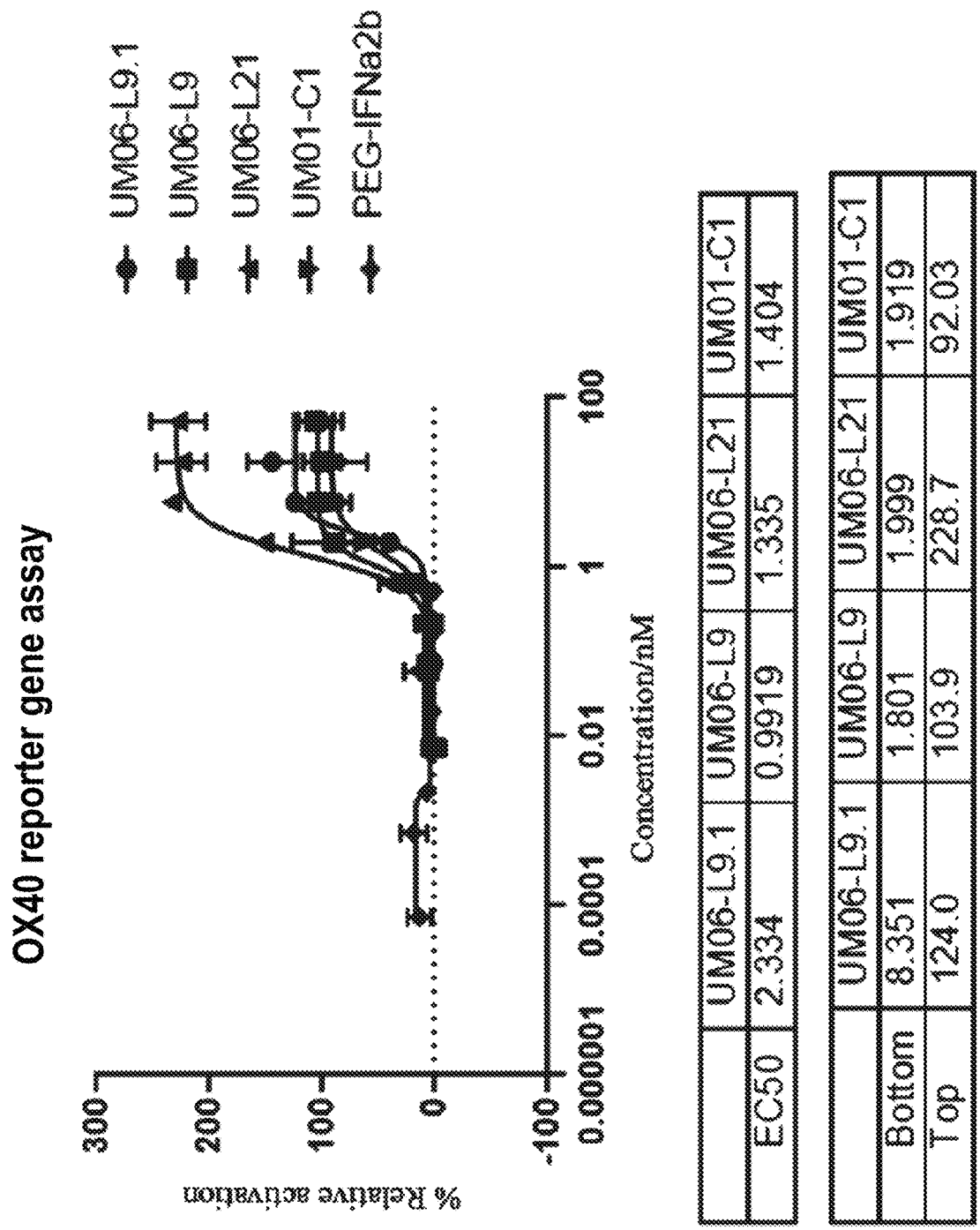
FIGS. 13A and 13B show that the OX40 antibody/IFNα-2a fusion proteins according to the present disclosure activate the activity of NF-κB signaling pathway in Jurkat cells.
Figure 13B:
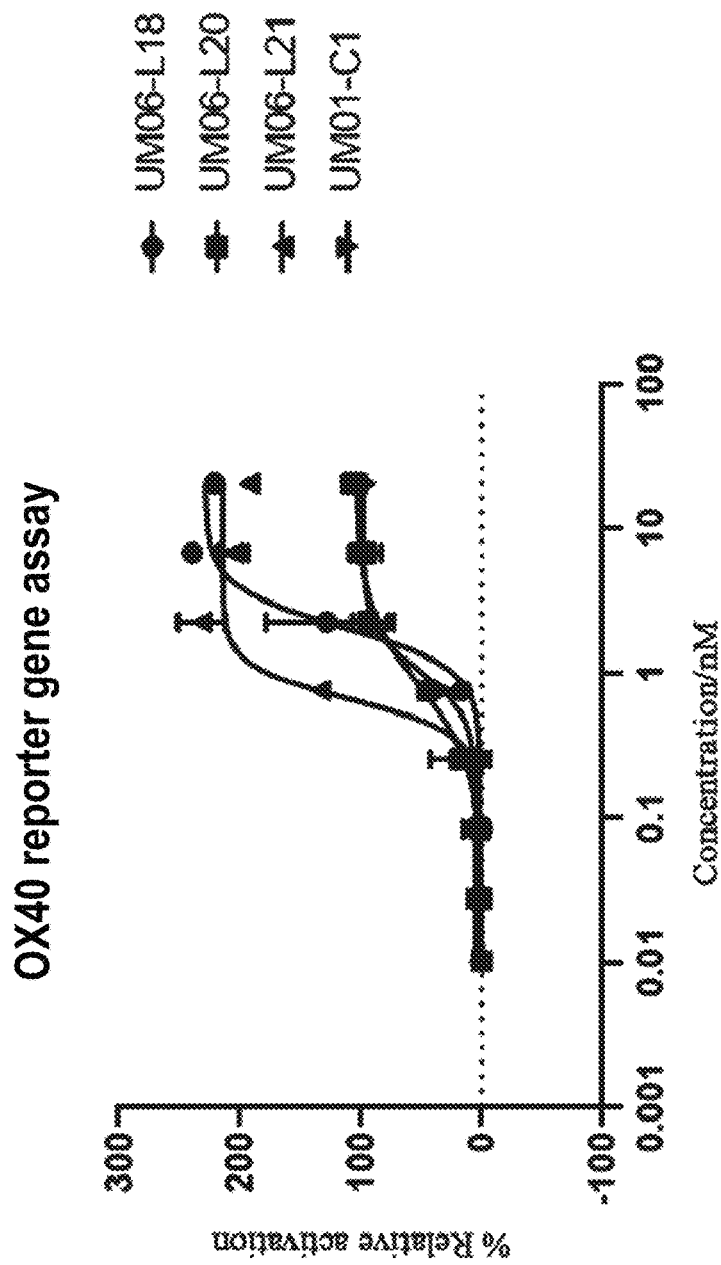

As shown in FIGS. 13A and 13B, the average value of signals from the detection wells without the added OX40 agonist was set to 0% activation, and in the detection wells added with different concentration gradients of the MT01-C1 mAb, the concentration group with the maximum average of activation signal was set to 100% activation, and the detected fluorescence signal values of other samples were normalized on the basis of this. As can be seen from the detection results in FIG. 13A, pegylated interferon α2 (Pegberon, Xiamen Amoytop Biotech, Batch No. 201811JS19) has no activation effect on HEK293-OX40-NFκB-Luc, indicating that the activity of interferon α2 in the fusion protein molecule has no interference on the OX40 activity detection system. The activities of the OX40 antibody MT01-C1, and the fusion proteins UM06-L9, UM06-L9.1, UM06-L18, UM06-L20 and UM06-L21 to activate NFκB-luciferase reporter gene in the above assay system were judged by $EC_{50}$, and there was no significant difference between various molecules. However, in view of the maximal activation fold of OX40 reporter gene, the activation folds of UM06-L18 and UM06-L21 were significantly larger than those of other molecules (FIG. 13B. In summary, UM06-L21 has a maximum efficacy and potency.

Example 15: Pharmacokinetics Assay in Balb/c Mice

Six female Balb/c mice aged 6-8 weeks were injected with UM06-L21 intravenously. The dose administered was 5 mg/kg. The peripheral venous blood was collected from the animals before the administration and at 1, 2, 6, 24, 48, 72, 96, 168, 240 and 336 h after the administration. Serums were collected from 3 animals at each time point, and the blood samples were collected alternately from 6 animals at different time points.

A 96-well high affinity plate was coated with 1 μg/mL human OX40 protein solution at 100 μL/well and shaken overnight at 4° C. The next day, the plate was first washed 3 times with 300 μL PBST (Tween 20: 0.5% c), then blocked with 5% BSA/PBS at 100 μL/well for 1 h, and shaken at room temperature, followed by washing 4 times with 300 μL PBST. 100-fold diluted solutions of serum samples to be tested and control serum solutions with different concentrations were prepared by PBS and then added to the 96-well plate at 100 μL/well; the plate was shaken for 1.5 h at room temperature, followed by washing 4 times with 300 μL PBST. 0.5 μg/mL rabbit-anti-human IFN (Abcam, Art. No. ab222552) solution was prepared and added into the 96-well plate at 100 μL/well, and the plate was shaken for 1.5 h at room temperature, followed by washing 4 times with 300 μL PBST. A secondary antibody goat-anti-rabbit IgG HRP (GenScript Biotech Corp., Art. No. A00098) solution was prepared and added into the 96-well plate at 100 μL/well, and the plate was shaken for 1 h at room temperature, followed by washing 4 times with 300 µL PBST. TMB was added at 100 µL/well to develop color for 20 min. 0.6N $H_2SO_4$ was added at 100 µL/well to stop the color development, and the OD (optical density) values were determined at 450 nm. Logistic four-parameter fitting was conducted on the detection values of the control solutions with different concentrations relative to the concentrations of the control solutions to obtain a standard curve and a regression equation. The detected values of the samples to be tested were substituted into the equation for calculation to obtain the serum drug concentrations at different time points.

Figure 14:
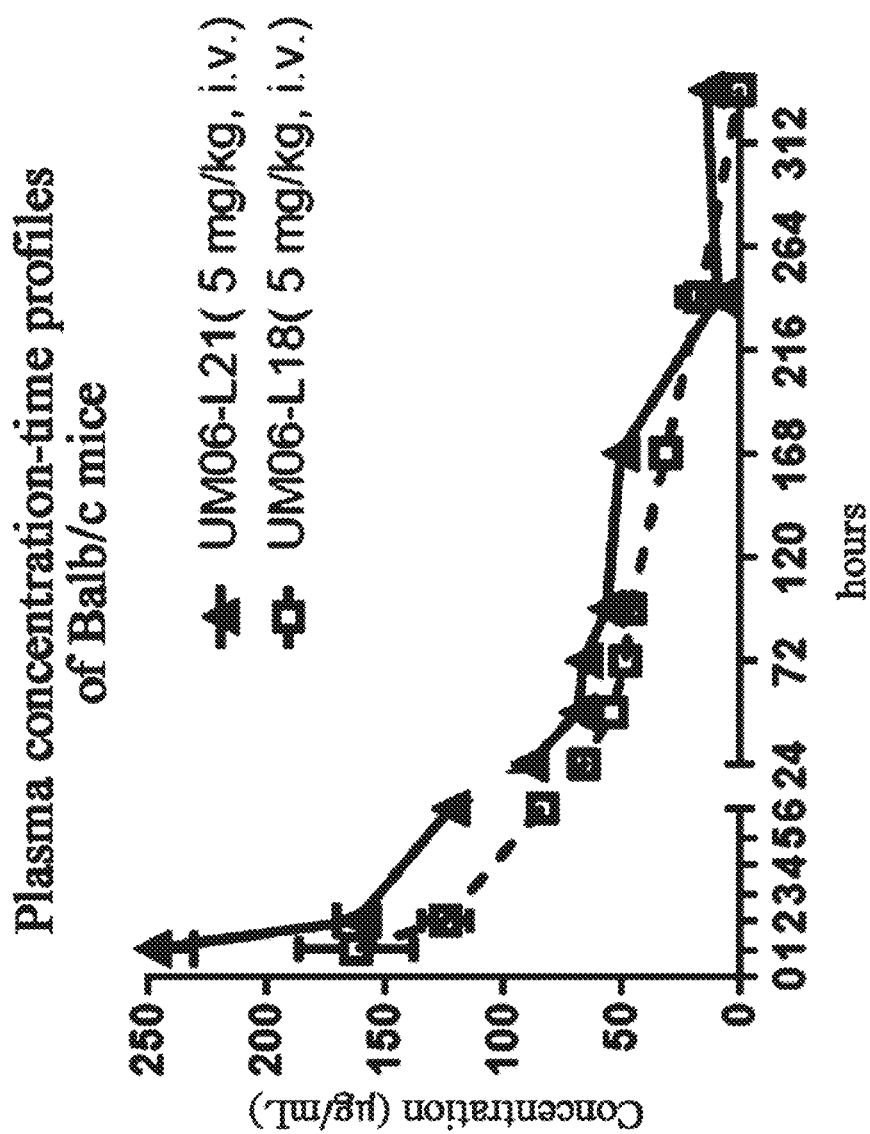
FIG. 14 shows the plasma concentration time profiles of the OX40 antibody/IFNα-2a fusion proteins UM06-L18 and UM06-L21 according to the present disclosure in mice.

As shown in FIG. 14, the mice in the experiment were injected intravenously with 5 mg/kg UM06-L18 and UM06-L21. 14 days after the administration of UM06-L21, the serum drug concentration was still above 10 µg/mL, but UM06-L18 could not be detected, indicating that the fusion protein UM06-L21 had better pharmacokinetic properties than UM06-L18 in the mouse model. The areas under the curve (AUC) for UM06-L21 and UM06-L18 were further calculated as 14469+/−3220 and 11062+/−1282 h·µg/mL, respectively. The AUC of UM06-L21 was significantly higher than that of UM06-L18 by t-test statistical analysis (P=0.025).

The above are merely the preferred examples of the present invention, which do not impose any limitation on the present invention. Any form of equivalent replacement or modification and the like performed by those skilled in the art on the technical solutions and technical contents disclosed by the present invention without departing from the scope of the technical solutions of the present invention belong to the contents that do not deviate from the technical solutions of the present invention and still fall within the protection scope of the present invention.

MAIN REFERENCES

1. Willoughby J, Griffiths J, Tews I, Cragg M S. OX40: Structure and function—What questions remain? *Mol. Immunol.* 2017; 83:13-22. doi: 10.1016/j.molimm.2017.01.006.
2. Imura A, Hori T, Imada K, Ishikawa T, Tanaka Y, Maeda M, Imamura S, Uchiyama T. The human OX40/gp34 system directly mediates adhesion of activated T cells to vascular endothelial cells. *J. Exp. Med.* 1996; 183: 2185-2195. doi:
3. Burgess J K, Carlin S, Pack R A, Arndt G M, Au W W, Johnson P R, Black J L, Hunt N H. Detection and characterization of OX40 ligand expression in human airway smooth muscle cells: a possible role in asthma? *J. Allergy Clin. Immunol.* 2004; 113:683-689. doi: 10.1016/j.jaci.2003.12.311.
4. Compaan D M, Hymowitz S G. The crystal structure of the costimulatory OX40-OX40L complex. *Structure* 2006; 14:1321-1330. doi: 10.1016/j.str.2006.06.015.
5. Song J, So T, Croft M. Activation of NF-kappaB1 by OX40 contributes to antigen-driven T cell expansion and survival. *J. Immunol.* 2008; 180:7240-7248. doi:
6. Croft M. Control of immunity by the TNFR-related molecule OX40 (CD134). *Annu. Rev. Immunol.* 2010; 28:57-78. doi: 10.1146/annurev-immunol-030409-101243.
7. Rogers P R, Song J, Gramaglia I, Killeen N, Croft M. OX40 promotes Bcl-xL and Bcl-2 expression and is essential for long-term survival of CD4 T cells. *Immunity* 2001; 15:445-455. doi:
8. Song J, So T, Cheng M, Tang X, Croft M. Sustained survivin expression from OX40 costimulatory signals drives T cell clonal expansion. Immunity 2005; 22:621-631. doi: 10.1016/j.immuni.2005.03.012.
9. So T, Song J, Sugie K, Altman A, Croft M. Signals from OX40 regulate nuclear factor of activated T cells cl and T cell helper 2 lineage commitment. *Proc. Natl. Acad. Sci. USA* 2006; 103:3740-3745. doi: 10.1073/pnas.0600205103.
10. Publicover J, Gaggar A, Jespersen J M, Halac U, Johnson A J, Goodsell A, Avanesyan L, Nishimura S L, Holdorf M, Mansfield K G, Judge J B, Koshti A, Croft M, et al. An OX40/OX40L interaction directs successful immunity to hepatitis B virus. *Sci. Transl. Med.* 2018; 10. doi: 10.1126/scitranslmed.aah5766.

The invention claimed is:

1. A fusion protein comprising:
   a) an antibody or antigen-binding fragment thereof that specifically binds to human OX40; and
   b) a human interferon;
   wherein the human interferon is linked to the carboxyl- or amino-terminus of the light or heavy chain of the antibody directly or via a peptide linker;
   wherein the antibody or antigen-binding fragment thereof that specifically binds to human OX40 comprises:
   an antibody heavy chain variable region comprising VH CDR1 having the amino acid sequence of SEQ ID NO:1, VH CDR2 having the amino acid sequence of SEQ ID NO:2, and VH CDR3 having the amino acid sequence of SEQ ID NO:3; and
   an antibody light chain variable region comprising VL CDR1 having the amino acid sequence of SEQ ID NO:4, VL CDR2 having the amino acid sequence of SEQ ID NO:5, and VL CDR3 having the amino acid sequence of SEQ ID NO:6.

2. The fusion protein according to claim 1, wherein the heavy chain variable region comprises the amino acid sequence as shown in SEQ ID NO:7, and the light chain variable region comprises the amino acid sequence as shown in SEQ ID NO:8.

3. The fusion protein according to claim 1, wherein the antibody or antigen-binding fragment thereof that specifically binds to human OX40 is scFv, a scFv dimer, BsFv, dsFv, dsFv$_2$, dsFv-dsFv', a Fv fragment, Fab, Fab', F(ab')$_2$, or a ds diabody.

4. The fusion protein according to claim 1, wherein the antibody further comprises a constant region of immunoglobulin; preferably, the constant region is a constant region of human IgG1, IgG2 or IgG4.

5. The fusion protein according to claim 1, wherein the human interferon is human interferon type I.

6. The fusion protein according to claim 5, wherein the human interferon is human interferon IFNα-2b.

7. The fusion protein according to claim 6, wherein the human interferon is IFNα-2b having the amino acid sequence as shown in SEQ ID NO:9.

8. The fusion protein according to claim 6, wherein the human interferon is an IFNα-2b mutant, which has one or more mutations comprising T106A, R149A, A145G, A145D, R120A, or L117A relative to the amino acid sequence as shown in SEQ ID NO:9;
wherein the IFNα-2b mutant has one or more double mutations comprising T106A/A145D, T106A/R149A, T106A/A145G, T106A/R120A, or T106A/L117A relative to the amino acid sequence as shown in SEQ ID NO:9.

9. The fusion protein according to claim 1, wherein the peptide linker is selected from the group consisting of (G)n, KESGSVSSEQLAQFRSLD (SEQ ID NO:30), EGKSSGSGSESKST (SEQ ID NO:31), GSAGSAAGSGEF (SEQ ID NO:32), (GGGGS)n (SEQ ID NO:33) and (GGSGG)n (SEQ ID NO:34); wherein n is an integer between 0 and 5.

10. The fusion protein according to claim 1, wherein the fusion protein is one or more of UMY02-L1, UMY02-L2, UMY02-L3, UMY02-L4, UMY02-L5, UMY02-L6, UMY02-L7, UMY02-L8, UMY02-L13, UMY02-L14, UMY02-L15, UMY02-L16, UMY02-L17, UMY02-L18, UM06-L9, UM06-L9.1, UM06-L18, UM06-L20 or UM06-L21.

11. An isolated polynucleotide encoding the fusion protein according to claim 1.

12. A vector comprising the isolated polynucleotide according to claim 11.

13. A host cell comprising the vector according to claim 12.

14. A pharmaceutical composition comprising the fusion protein according to claim 1 and a pharmaceutically acceptable carrier.

15. The fusion protein according to claim 9, wherein the peptide linker is (GGGGS)$_n$ (SEQ ID NO:33).

16. The fusion protein according to claim 9, wherein n is an integer between 1 and 3.

* * * * *